United States Patent
Thorne

(10) Patent No.: US 11,065,286 B2
(45) Date of Patent: Jul. 20, 2021

(54) HIGH MOBILITY GROUP BOX I MUTANT

(71) Applicant: Stephen H. Thorne, Pittsburgh, PA (US)

(72) Inventor: Stephen H. Thorne, Pittsburgh, PA (US)

(*) Notice: Subject to any disclaimer, the term of this patent is extended or adjusted under 35 U.S.C. 154(b) by 0 days.

(21) Appl. No.: 16/335,515

(22) PCT Filed: Sep. 21, 2017

(86) PCT No.: PCT/US2017/052746
§ 371 (c)(1),
(2) Date: Mar. 21, 2019

(87) PCT Pub. No.: WO2018/057755
PCT Pub. Date: Mar. 29, 2018

(65) Prior Publication Data
US 2019/0209629 A1    Jul. 11, 2019

Related U.S. Application Data

(60) Provisional application No. 62/397,523, filed on Sep. 21, 2016.

(51) Int. Cl.
| | |
|---|---|
| *A61K 35/768* | (2015.01) |
| *A61K 45/06* | (2006.01) |
| *A61K 31/7088* | (2006.01) |
| *A61P 35/00* | (2006.01) |
| *C07K 14/47* | (2006.01) |

(52) U.S. Cl.
CPC ........ *A61K 35/768* (2013.01); *A61K 31/7088* (2013.01); *A61K 45/06* (2013.01); *A61P 35/00* (2018.01); *C07K 14/4702* (2013.01); *C12N 2710/24132* (2013.01); *Y02A 50/30* (2018.01)

(58) Field of Classification Search
None
See application file for complete search history.

(56) References Cited

U.S. PATENT DOCUMENTS

| | | |
|---|---|---|
| 2005/0152903 A1 | 7/2005 | Newman et al. |
| 2006/0111287 A1* | 5/2006 | Bianchi .................. A61P 35/00 530/387.3 |
| 2009/0285860 A1 | 11/2009 | Martuza et al. |
| 2013/0183348 A1 | 7/2013 | Taniguchi et al. |
| 2016/0235793 A1* | 8/2016 | Thorne ................ A61K 35/768 |

FOREIGN PATENT DOCUMENTS

| | | |
|---|---|---|
| EP | 2703487 A1 | 3/2014 |
| WO | WO-2004014314 A2 | 2/2004 |
| WO | WO-2012142529 A2 | 10/2012 |
| WO | WO-2013038066 A1 | 3/2013 |

OTHER PUBLICATIONS

B Huang et al: "Synergistic anti-tumor effects between oncolytic vaccinia virus and paclitaxel are mediated by the IFN response and HMGB1", Gene Therapy, vol. 18, No. 2, Aug. 26, 2010(Aug. 26, 2010), pp. 164-172, XP055201120,ISSN: 0969-7128, DOI:10.1038/gt.2010.121.
D. Tang et al.: "Endogenous HMGB1regulates autophagy", Journal of Experimental Medicine, vol. 464, No. 7285, Sep. 6, 2010 (Sep. 6, 2010), pp. 104-892, XP055080019, ISSN:1476-4687, DOI: 10.1038/nature08780. 0.
R. Kang et al:"HMGB1 in Cancer: Good ,Bad, or Both?", Clinical Cancer Research, vol. 19, No. 15, May 30, 2013 (May 30, 2013), pp. 4046-4057, XP055690795, US, ISSN: 1078-0432, DOI:10.1158/1078-0432.CCR-13-0495.
Supplementary European Search Report and Written Opinion dated May 12, 2020 for Application No. EP 17853903.7, (9 pages).
Altschul, S F et al. "Gapped BLAST and PSI-BLAST: a new generation of protein database search programs." Nucleic acids research vol. 25,17 (1997): 3389-402. doi:10.1093/nar/25.17.3389.
Rojas, Juan J et al. "Manipulating TLR Signaling Increases the Anti-tumor T Cell Response Induced by Viral Cancer Therapies." Cell reports vol. 15,2 (2016): 264-73. doi:10.1016/j.celrep.2016.03.017.
Samuel Karlin et al., "Applications and statistics for multiple high-scoring segments in molecular sequences", Proc. Natl. Acad. Sci. USA, vol. 90, 5873-5877, Jun. 1993.

* cited by examiner

*Primary Examiner* — Channing S Mahatan
(74) *Attorney, Agent, or Firm* — Greenberg Traurig, LLP

(57) ABSTRACT

Provided herein are oncolytic vaccinia viruses which have been modified to contain an exogenous nucleic acid that codes for a variant HMGB1 protein. Such vaccinia viruses modified to contain nucleic acid encoding variant HMGB1 and that express a variant HMGB1 or a fragment thereof can achieve a synergistic effect in combination with chemotherapy. Methods of using oncolytic vaccinia viruses modified to contain an exogenous nucleic acid that codes for a variant HMGB1 protein, in the treatment of various cancers, are also provided.

23 Claims, 19 Drawing Sheets

Specification includes a Sequence Listing.

Figure 1
a
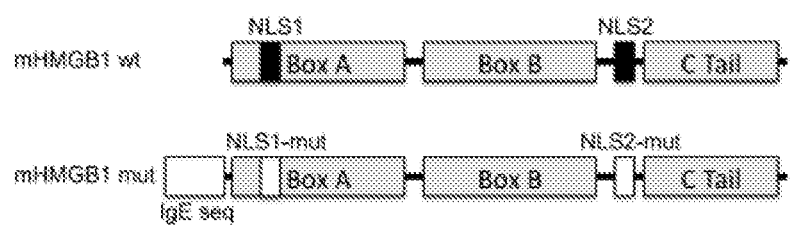
b
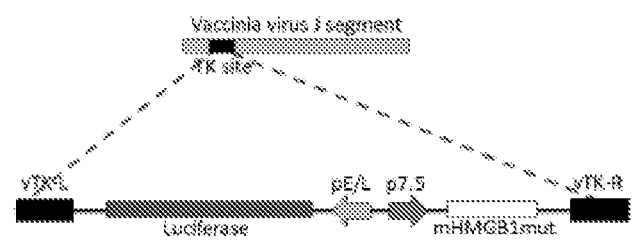
c
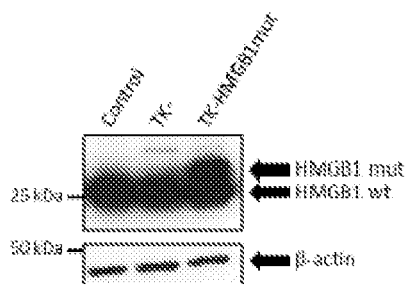

Cont'd. FIGURE 1
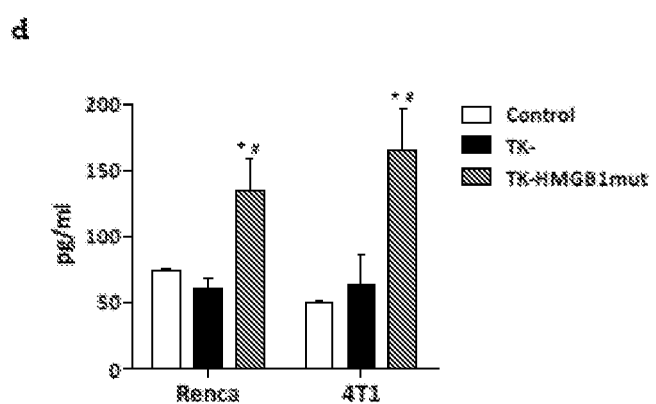

Figure 2
a
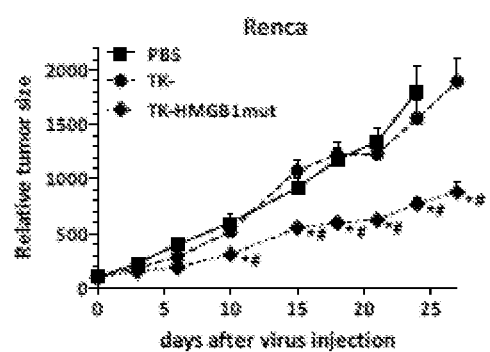
b
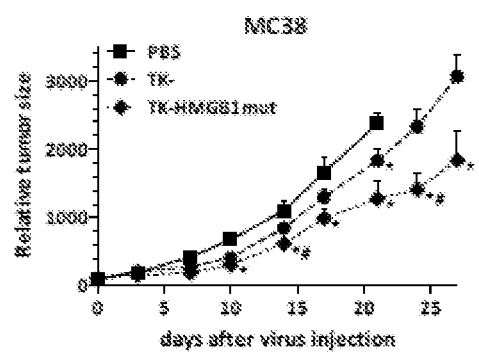

Figure 3
a
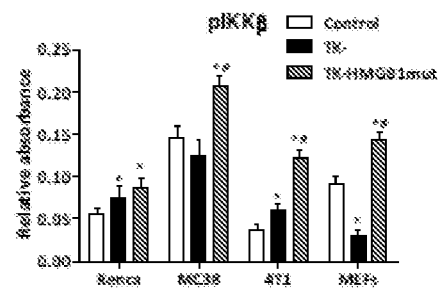
b
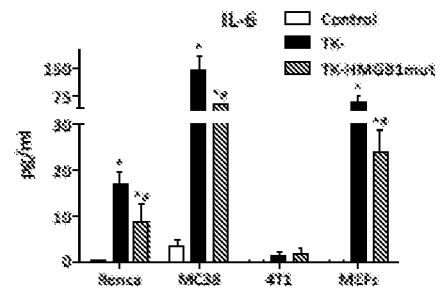

Figure 3 – cont'd.
c
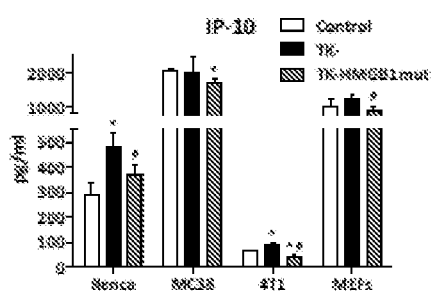
d
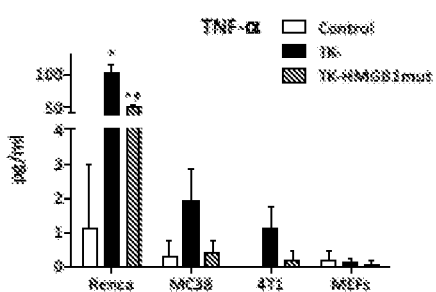

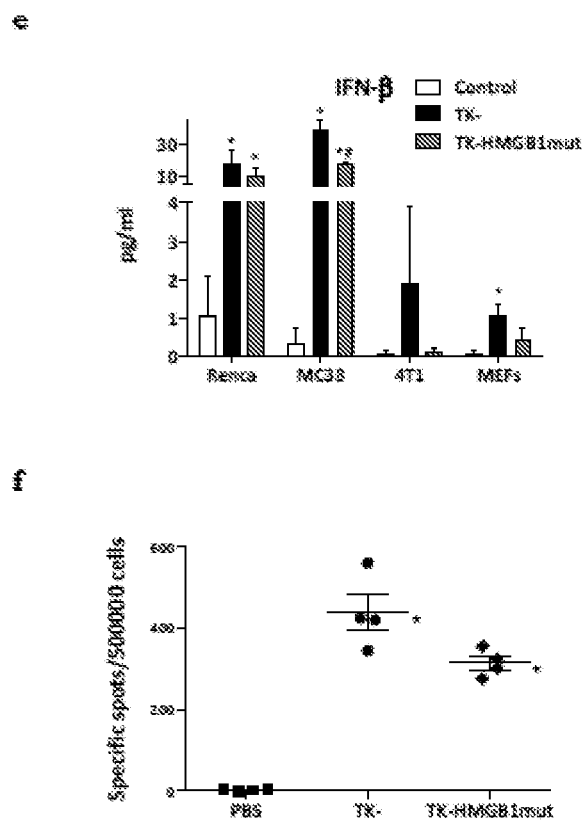
Figure 3 – cont'd.

Figure 3 – cont'd.
g
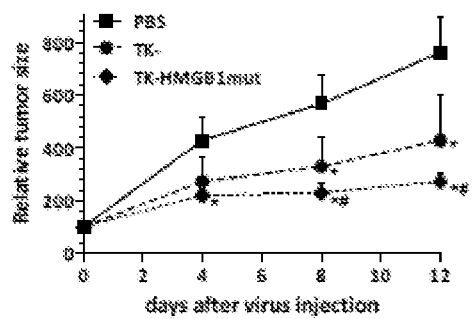

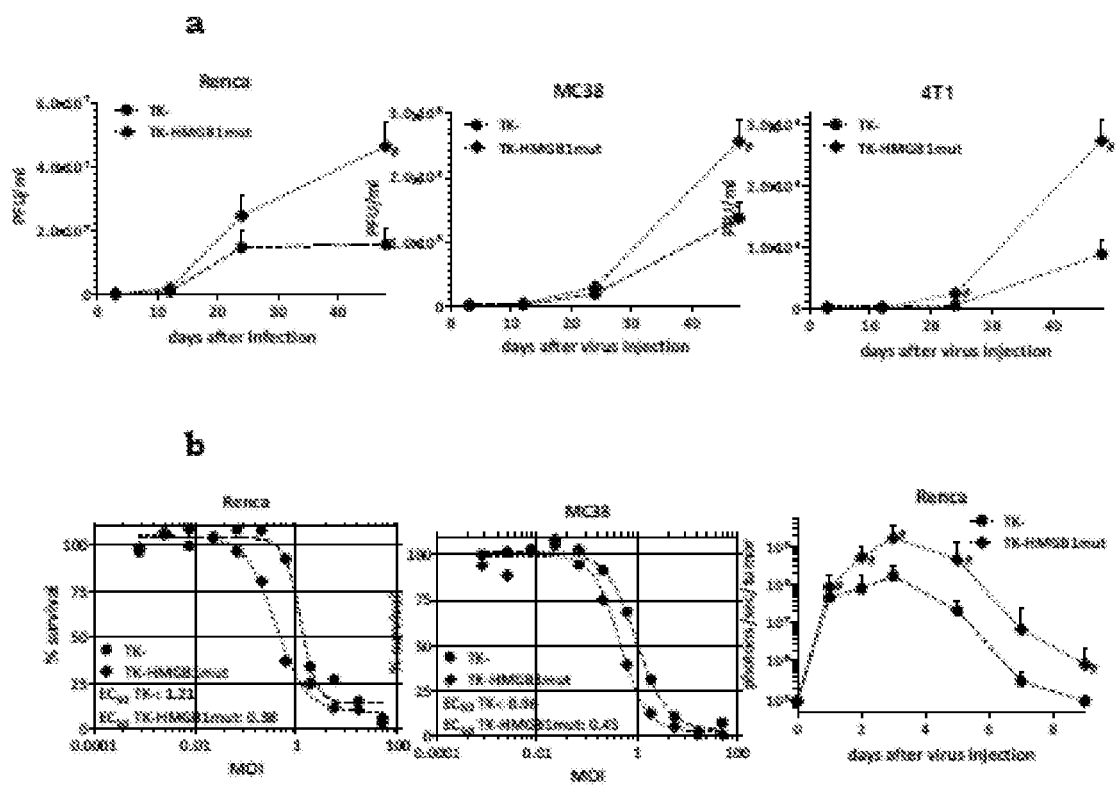

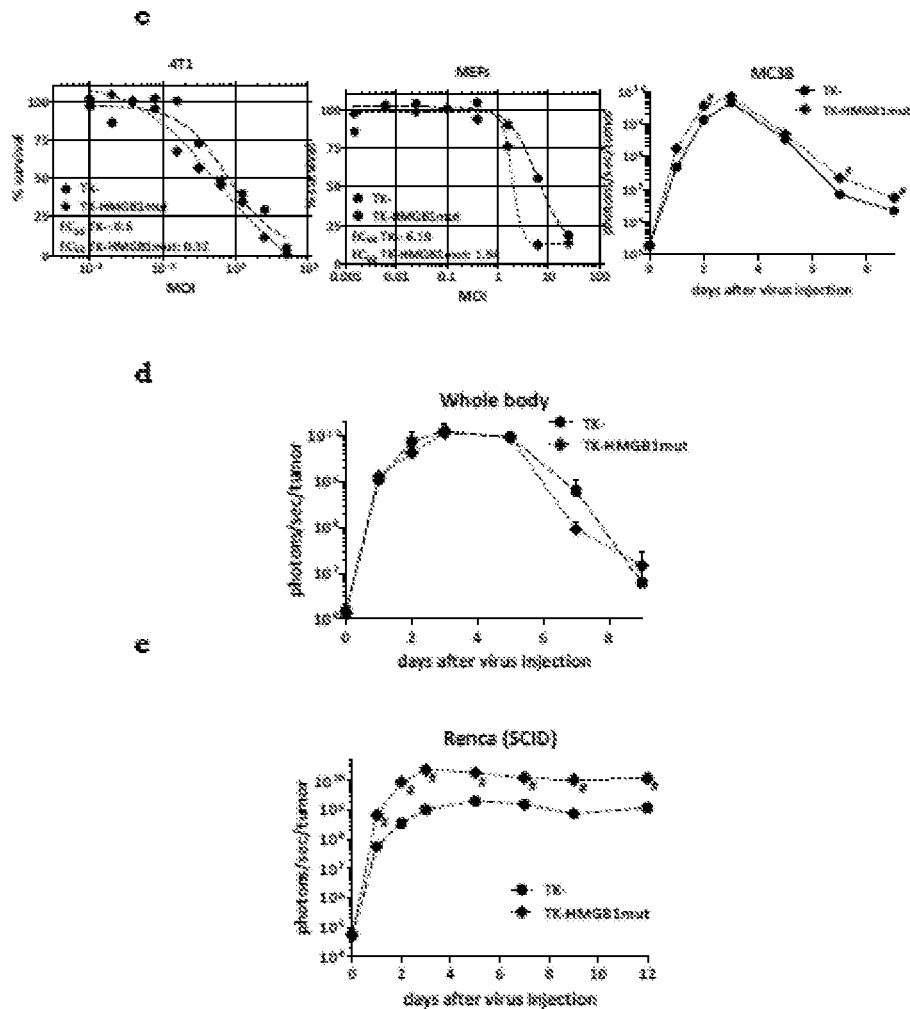
Figure 4-cont'd.

Figure 5
a
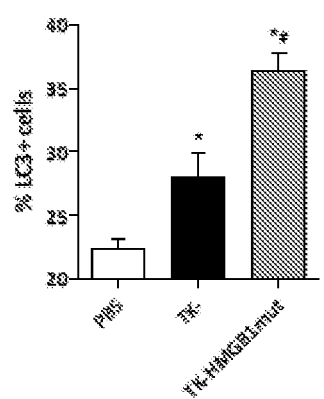
b
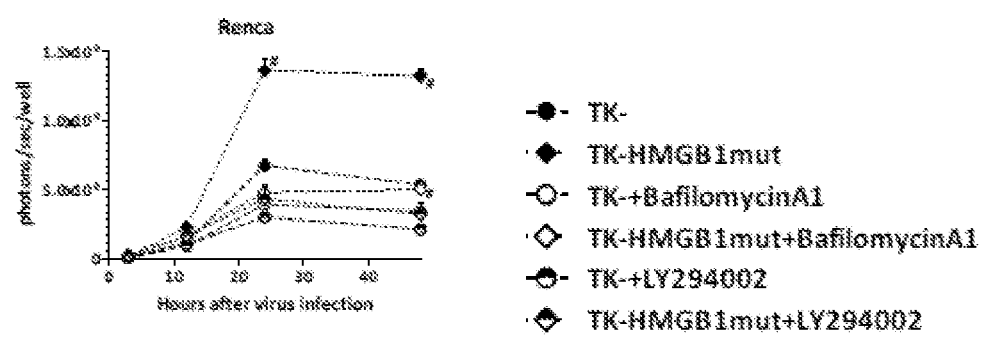

Figure 5b – cont'd.
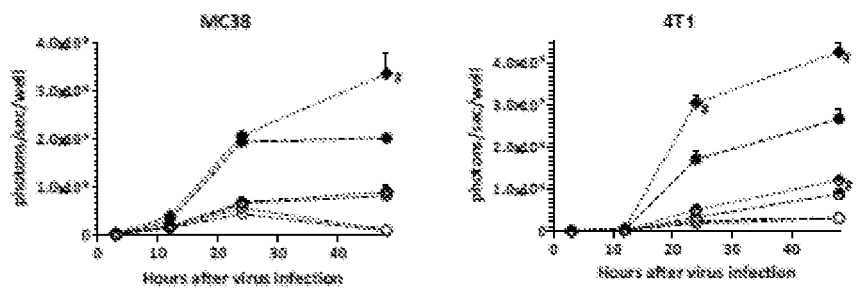

Figure 6
a
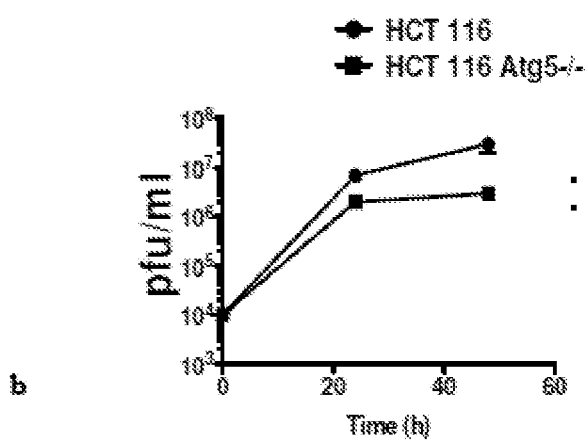
b
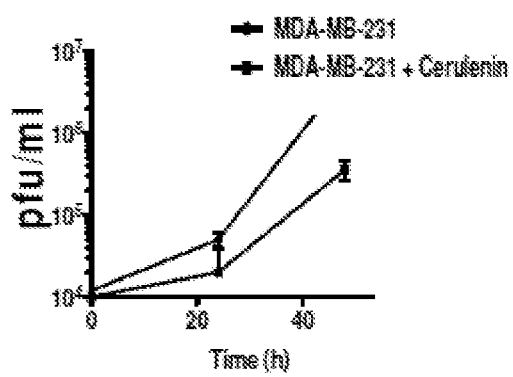

Figure 6 – cont'd.
c
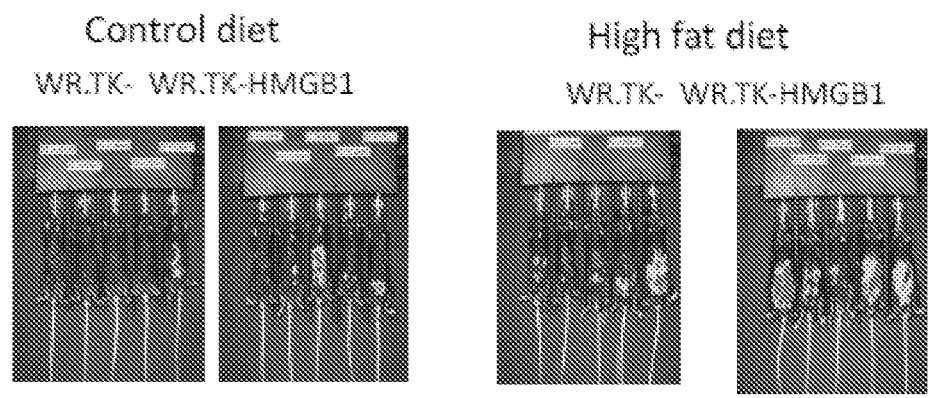
d
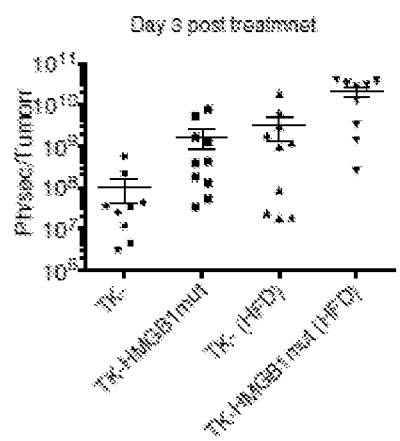

Figure 7
a
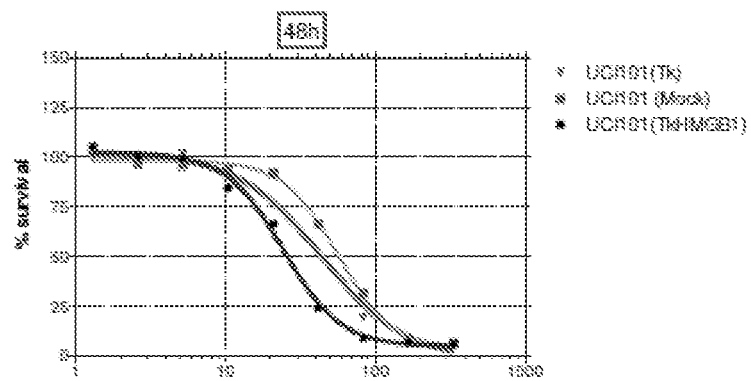
b
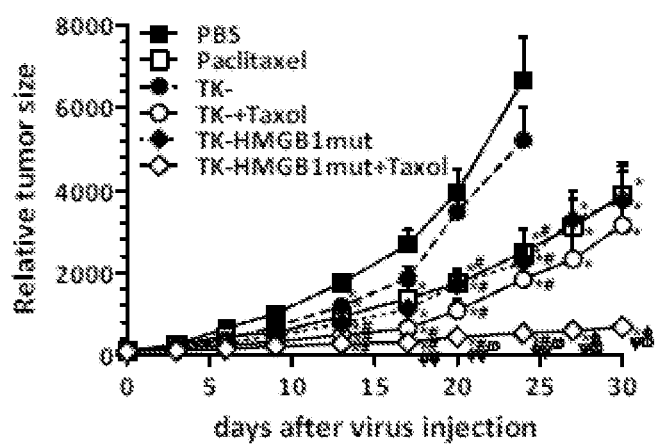

Fig 8 (A) Viral gene expression (BLI) from strains also expressing MMP8 or PH20 and (B) data quantified for

SEQUENCE LISTING

```
<160> NUMBER OF SEQ ID NOS: 25

<210> SEQ ID NO 1
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (706)..(714)
<223> OTHER INFORMATION: a, c, t, g, unknown or other

<400> SEQUENCE: 1
ctcgagatgg actggacatg gattctcttt ctagtggccg cagccacaag ggtccactcc      60
atgggcaaag gagatcctaa aaagccgaga ggcaaaatgt cctcatatgc attctttgtg     120
caaacttgcc gggaggagca caagaagaag cacccggatg ctgcagtcaa cttcgctgag     180
ttcgcaaaga agtgcgctga gaggtggaag accatggcag ctaaagaaaa ggggaaattt     240
gaagatatgg caaaggctga caaggctcgt tatgaaagag aaatgaaaac ctacatcccc     300
```

-continued

```
cccaaggggg agaccaaaaa gaagttcaag gaccccaatg cacccaagag gcctccttcg       360
gccttcttct tgttctgttc tgagtaccgc cccaaaatca aggcgagca tcctggctta        420 tccattggtg atgttgcaaa gaaactagga gagatgtgga acaacactgc agcagatgac       480
aagcagccct atgagaagaa agctgccaag ctgaaggaga gtatgagaa ggatattgct        540 gcctacagag ctaaaggaaa acctgatgca gcgaaaaagg gggtggtcaa ggctgaaaag       600
gcgaagaaaa agaaggaaga ggaagatgat gaggaggatg aagaggatga ggaagaggag       660
gaagaagagg aagacgaaga tgaagaagaa gatgatgatg atgaannnnn nnnn            714
```

```
<210> SEQ ID NO 2
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ctcgagatgg actggacatg gattctcttt ctagtggccg cagccacaag ggtccactcc       60
atgggcaaag gagatcctaa aaagccgaga ggcaaaatgt cctcatatgc attctttgtg      120
caaacttgcc gggaggagca caagaagaag caccccggatg ctgcagtcaa cttcgctgag    180
ttcgca                                                                186
```

```
<210> SEQ ID NO 3
<211> LENGTH: 498
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (490)..(498)
<223> OTHER INFORMATION: a, c, t, g, unknown or other

<400> SEQUENCE: 3
gcagctaaag aaaagggaa atttgaagat atggcaaagg ctgacaaggc tcgttatgaa        60
agagaaatga aaacctacat ccccccccaaa ggggagacca aaagaagtt caaggacccc      120 aatgcaccca agaggcctcc ttcggccttc ttcttgttct gttctgagta ccgccccaaa      180
atcaaaggcg agcatcctgg cttatccatt ggtgatgttg caagaaact aggagagatg      240 tggaacaaca ctgcagcaga tgacaagcag ccctatgaga gaaagctgc caagctgaag      300 gagaagtatg agaaggatat tgctgcctac agagctaaag gaaaacctga tgcagcgaaa    360 aaggggggtgg tcaaggctga aaaggcgaag aaaagaagg aagaggaaga tgatgaggag    420
gatgaagagg atgaggaaga ggaggaagaa gaggaagacg aagatgaaga agaagatgat    480
gatgatgaan nnnnnnnn                                                   498
```

```
<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Glu Met Asp Trp Thr Trp Ile Leu Phe Leu Val Ala Ala Ala Thr
```

```
                1               5                  10                  15
            Arg Val His Ser Met Gly Lys Gly Asp Pro Lys Lys Pro Arg Gly Lys
                            20                  25                  30
            Met Ser Ser Tyr Ala Phe Phe Val Gln Thr Cys Arg Glu Glu His Lys
                            35                  40                  45
            Lys Lys His Pro Asp Ala Ala Val Asn Phe Ala Glu Phe Ala Lys Lys
                    50                  55                  60
            Cys Ala Glu Arg Trp Lys Thr Met Ala Ala Lys Glu Lys Gly Lys Phe
            65                  70                  75                  80
            Glu Asp Met Ala Lys Ala Asp Lys Ala Arg Tyr Glu Arg Glu Met Lys
                            85                  90                  95
            Thr Tyr Ile Pro Pro Lys Gly Glu Thr Lys Lys Glu Lys Asp Pro
                        100                 105                 110
            Asn Ala Pro Lys Arg Pro Pro Ser Ala Phe Phe Leu Phe Cys Ser Glu
                        115                 120                 125
            Tyr Arg Pro Lys Ile Lys Gly Glu His Pro Gly Leu Ser Ile Gly Asp
                    130                 135                 140
            Val Ala Lys Lys Leu Gly Glu Met Trp Asn Asn Thr Ala Ala Asp Asp
            145                 150                 155                 160
            Lys Gln Pro Tyr Glu Lys Lys Ala Ala Lys Leu Lys Glu Lys Tyr Glu
                            165                 170                 175
            Lys Asp Ile Ala Ala Tyr Arg Ala Lys Gly Lys Pro Asp Ala Ala Lys
                        180                 185                 190
            Lys Gly Val Val Lys Ala Glu Lys Ala Lys Lys Lys Glu Glu Glu
                    195                 200                 205
            Asp Asp Glu Glu Asp Glu Glu Asp Glu Glu Glu Glu Glu Glu Glu Glu
                210                 215                 220
            Asp Glu Asp Glu Glu Asp Asp Asp Glu Glu Ala Ser
            225                 230                 235

<210> SEQ ID NO 5
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Glu Met Asp Trp Thr Trp Ile Leu Phe Leu Val Ala Ala Ala Thr
1               5                   10                  15
Arg Val His Ser Met Gly Lys Gly Asp Pro Lys Lys Pro Arg Gly Lys
                20                  25                  30
Met Ser Ser Tyr Ala Phe Phe Val Gln Thr Cys Arg Glu Glu His Lys
            35                  40                  45
Lys Lys His Pro Asp Ala Ala Val Asn Phe Ala Glu Phe Ala
        50                  55                  60

<210> SEQ ID NO 6
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Ala Lys Glu Lys Gly Lys Phe Glu Asp Met Ala Lys Ala Asp Lys
```

```
1               5                   10                  15
Ala Arg Tyr Glu Arg Glu Met Lys Thr Tyr Ile Pro Pro Lys Gly Glu
            20                  25                  30

Thr Lys Lys Phe Lys Asp Pro Asn Ala Pro Lys Arg Pro Pro Ser
        35                  40                  45

Ala Phe Phe Leu Phe Cys Ser Glu Tyr Arg Pro Lys Ile Lys Gly Glu
        50                  55                  60

His Pro Gly Leu Ser Ile Gly Asp Val Ala Lys Lys Leu Gly Glu Met
65                  70                  75                  80

Trp Asn Asn Thr Ala Ala Asp Asp Lys Gln Pro Tyr Glu Lys Lys Ala
                85                  90                  95

Ala Lys Leu Lys Glu Lys Tyr Glu Lys Asp Ile Ala Ala Tyr Arg Ala
            100                 105                 110

Lys Gly Lys Pro Asp Ala Ala Lys Lys Gly Val Val Lys Ala Glu Lys
            115                 120                 125

Ala Lys Lys Lys Lys Glu Glu Glu Asp Asp Glu Glu Asp Glu Glu Asp
        130                 135                 140

Glu Glu Glu Glu Glu Glu Glu Asp Glu Asp Glu Glu Asp Asp
145                 150                 155                 160

Asp Asp Glu Ala Ser
            165

<210> SEQ ID NO 7
<211> LENGTH: 60
<212> TYPE: DNA
<213> ORGANISM: Homo sapiens

<400> SEQUENCE: 7
tttaaagatc cgaacgcgcc gaaacgcccg ccgagcgcgt ttttctgtt ttgcagcgaa    60

<210> SEQ ID NO 8
<211> LENGTH: 20
<212> TYPE: PRT
<213> ORGANISM: Homo sapiens

<400> SEQUENCE: 8

Phe Lys Asp Pro Asn Ala Pro Lys Arg Pro Pro Ser Ala Phe Phe Leu
1               5                   10                  15

Phe Cys Ser Glu
            20

<210> SEQ ID NO 9
<211> LENGTH: 102
<212> TYPE: DNA
<213> ORGANISM: Homo sapiens

<400> SEQUENCE: 9
aaactgaaag aaaaatatga aaagatatt gcggcgtatc gcgcgaaagg caaaccggat    60
gcggcgaaaa aaggcgtggt gaaagcggaa aaaagcaaaa aa                     102

<210> SEQ ID NO 10
<211> LENGTH: 34
<212> TYPE: PRT
<213> ORGANISM: Homo sapiens

<400> SEQUENCE: 10

Lys Leu Lys Glu Lys Tyr Glu Lys Asp Ile Ala Ala Tyr Arg Ala Lys
1               5                   10                  15
```

Gly Lys Pro Asp Ala Ala Lys Lys Gly Val Val Lys Ala Glu Lys Ser
            20                  25                  30

Lys Lys

<210> SEQ ID NO 11
<211> LENGTH: 1341
<212> TYPE: DNA
<213> ORGANISM: Homo sapiens

<400> SEQUENCE: 11

```
ctgaactttc gcgcgccgcc ggtgattccg aacgtgccgt ttctgtgggc gtggaacgcg      60
ccgagcgaat tttgcctggg caaatttgat gaaccgctgg atatgagcct gtttagcttt     120
attggcagcc cgcgcattaa cgcgaccggc cagggcgtga ccatttttta tgtggatcgc     180
ctgggctatt atccgtatat tgatagcatt accggcgtga ccgtgaacgg cggcattccg     240
cagaaaatta gcctgcagga tcatctggat aaagcgaaaa agatattac cttttatatg      300
ccggtggata acctgggcat ggcggtgatt gattgggaag aatggcgccc gacctgggcg     360
cgcaactgga aaccgaaaga tgtgtataaa accgcagca ttgaactggt gcagcagcag      420
aacgtgcagc tgagcctgac cgaagcgacc gaaaaagcga acaggaatt tgaaaaagcg      480
ggcaaagatt ttctggtgga accattaaa ctgggcaaac tgctgcgccc gaaccatctg      540
tggggctatt atctgtttcc ggattgctat aaccatcatt ataaaaaacc gggctataac     600
ggcagctgct ttaacgtgga aattaaacgc aacgatgatc tgagctggct gtggaacgaa     660
agcaccgcgc tgtatccgag catttatctg aacacccagc agagcccggt ggcggcgacc     720
ctgtatgtgc gcaaccgcgt gcgcgaagcg attcgcgtga gcaaaattcc ggatgcgaaa     780
agcccgctgc cggtgtttgc gtataccccgc attgtgttta ccgatcaggt gctgaaattt     840
ctgagccagg atgaactggt gtatacccttt ggcgaaaccg tggcgctggg cgcgagcggc     900
attgtgattt ggggcaccct gagcattatg cgcagcatga aaagctgcct gctgctggat     960
aactatatgg aaaccattct gaacccgtat attattaacg tgaccctggc ggcgaaaatg    1020
tgcagccagg tgctgtgcca ggaacagggc gtgtgcattc gcaaaaactg aacagcagc     1080
gattatctgc atctgaaccc ggataacttt gcgattcagc tggaaaaagg cggcaaagaa    1140
accgtgcgcg gcaaaccgac cctggaagat ctggaacagt ttagcgaaaa atttattgc     1200
agctgctata gcaccctgag ctgcaaagaa aaagcggatg tgaaagatac cgatgcggtg    1260
gatgtgtgca ttgcggatgg cgtgtgcatt gatgcgtttc tgaaaccgcc gatggaaacc    1320
gaagaaccgc agattttta t                                               1341
```

<210> SEQ ID NO 12
<211> LENGTH: 447
<212> TYPE: PRT
<213> ORGANISM: Homo sapiens

<400> SEQUENCE: 12

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
 65                  70                  75                  80

Gln Lys Ile Ser Leu Gln Asp His Leu Asp Lys Ala Lys Lys Asp Ile
             85                  90                  95

Thr Phe Tyr Met Pro Val Asp Asn Leu Gly Met Ala Val Ile Asp Trp
        100                 105                 110

Glu Glu Trp Arg Pro Thr Trp Ala Arg Asn Trp Lys Pro Lys Asp Val
    115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Glu Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr
    435                 440                 445

<210> SEQ ID NO 13
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
ctcgagatgg actggacatg gattctcttt ctagtggccg cagccacaag ggtccactcc    60
atgggcaaag gagatcctaa aaagccgaga ggcaaaatgt cctcatatgc attctttgtg   120
caaacttgcc gggaggagca caagaagaag cacccggatg ctgcagtcaa cttcgctgag   180
ttcgcaaaga agtgcgctga gaggtggaag accatggcag ctaaagaaaa ggggaaattt   240
gaagatatgg caaaggctga caaggctcgt tatgaaagag aaatgaaaac ctacatcccc   300
cccaaagggg agaccaaaaa gaagttcaag gaccccaatg cacccaagag gcctccttcg   360
gccttcttct tgttctgttc tgagtaccgc cccaaaatca aggcgagca tcctggctta    420 tccattggtg atgttgcaaa gaaactagga gagatgtgga acaacactgc agcagatgac   480
aagcagccct atgagaagaa agctgccaag ctgaaggaga agtatgagaa ggatattgct   540
gcctacagag ctaaaggaaa acctgatgca gcgaaaaagg gggtggtcaa ggctgaaaag   600
gcgaagaaaa agaaggaaga ggaagatgat gaggaggatg aagaggatga ggaagaggag   660
gaagaagagg aagacgaaga tgaagaagaa gatgatgatg atgaa              705

<210> SEQ ID NO 14
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (706)..(708)
<223> OTHER INFORMATION: a, c, t, g, unknown or other

<400> SEQUENCE: 14
ctcgagatgg actggacatg gattctcttt ctagtggccg cagccacaag ggtccactcc    60
atgggcaaag gagatcctaa aaagccgaga ggcaaaatgt cctcatatgc attctttgtg   120
caaacttgcc gggaggagca caagaagaag cacccggatg ctgcagtcaa cttcgctgag   180
ttcgcaaaga agtgcgctga gaggtggaag accatggcag ctaaagaaaa ggggaaattt   240
gaagatatgg caaaggctga caaggctcgt tatgaaagag aaatgaaaac ctacatcccc   300
cccaaagggg agaccaaaaa gaagttcaag gaccccaatg cacccaagag gcctccttcg   360
gccttcttct tgttctgttc tgagtaccgc cccaaaatca aggcgagca tcctggctta    420 tccattggtg atgttgcaaa gaaactagga gagatgtgga acaacactgc agcagatgac   480
aagcagccct atgagaagaa agctgccaag ctgaaggaga agtatgagaa ggatattgct   540
gcctacagag ctaaaggaaa acctgatgca gcgaaaaagg gggtggtcaa ggctgaaaag   600
gcgaagaaaa agaaggaaga ggaagatgat gaggaggatg aagaggatga ggaagaggag   660
gaagaagagg aagacgaaga tgaagaagaa gatgatgatg atgaannngc tagc         714

<210> SEQ ID NO 15
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Glu Met Asp Trp Thr Trp Ile Leu Phe Leu Val Ala Ala Ala Thr

```
            1               5                   10                  15
Arg Val His Ser Met Gly Lys Gly Asp Pro Lys Lys Pro Arg Gly Lys
            20                  25                  30

Met Ser Ser Tyr Ala Phe Phe Val Gln Thr Cys Arg Glu Glu His Lys
            35                  40                  45

Lys Lys His Pro Asp Ala Ala Val Asn Phe Ala Glu Phe Ala Lys Lys
            50                  55                  60

Cys Ala Glu Arg Trp Lys Thr Met Ala Ala Lys Glu Lys Gly Lys Phe
65                  70                  75                  80

Glu Asp Met Ala Lys Ala Asp Lys Ala Arg Tyr Glu Arg Glu Met Lys
                85                  90                  95

Thr Tyr Ile Pro Pro Lys Gly Glu Thr Lys Lys Lys Glu Lys Asp Pro
                100                 105                 110

Asn Ala Pro Lys Arg Pro Pro Ser Ala Phe Phe Leu Phe Cys Ser Glu
                115                 120                 125

Tyr Arg Pro Lys Ile Lys Gly Glu His Pro Gly Leu Ser Ile Gly Asp
                130                 135                 140

Val Ala Lys Lys Leu Gly Glu Met Trp Asn Asn Thr Ala Ala Asp Asp
145                 150                 155                 160

Lys Gln Pro Tyr Glu Lys Lys Ala Ala Lys Leu Lys Glu Lys Tyr Glu
                165                 170                 175

Lys Asp Ile Ala Ala Tyr Arg Ala Lys Gly Lys Pro Asp Ala Ala Lys
                180                 185                 190

Lys Gly Val Val Lys Ala Glu Lys Ala Lys Lys Lys Glu Glu Glu
                195                 200                 205

Asp Asp Glu Glu Asp Glu Asp Glu Glu Glu Glu Glu Glu Glu
            210                 215                 220

Asp Glu Asp Glu Glu Asp Asp Asp Glu
225                 230                 235

<210> SEQ ID NO 16
<211> LENGTH: 215
<212> TYPE: PRT
<213> ORGANISM: Homo sapiens

<400> SEQUENCE: 16

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
            50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
            130                 135                 140
```

```
Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
            165                 170                 175

Lys Ala Glu Lys Ser Lys Lys Lys Glu Glu Glu Asp Glu Glu
                180                 185                 190

Asp Glu Glu Asp Glu Glu Glu Glu Asp Glu Glu Asp Glu Asp Glu
        195                 200                 205

Glu Glu Asp Asp Asp Asp Glu
        210                 215
```

```
<210> SEQ ID NO 17
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (236)..(236)
<223> OTHER INFORMATION: Any amino acid

<400> SEQUENCE: 17

Leu Glu Met Asp Trp Thr Trp Ile Leu Phe Leu Val Ala Ala Ala Thr
1               5                   10                  15

Arg Val His Ser Met Gly Lys Gly Asp Pro Lys Lys Pro Arg Gly Lys
            20                  25                  30

Met Ser Ser Tyr Ala Phe Phe Val Gln Thr Cys Arg Glu Glu His Lys
        35                  40                  45

Lys Lys His Pro Asp Ala Ala Val Asn Phe Ala Glu Phe Ala Lys Lys
    50                  55                  60

Cys Ala Glu Arg Trp Lys Thr Met Ala Ala Lys Glu Lys Gly Lys Phe
65                  70                  75                  80

Glu Asp Met Ala Lys Ala Asp Lys Ala Arg Tyr Glu Arg Glu Met Lys
                85                  90                  95

Thr Tyr Ile Pro Pro Lys Gly Glu Thr Lys Lys Lys Glu Lys Asp Pro
            100                 105                 110

Asn Ala Pro Lys Arg Pro Pro Ser Ala Phe Phe Leu Phe Cys Ser Glu
        115                 120                 125

Tyr Arg Pro Lys Ile Lys Gly Glu His Pro Gly Leu Ser Ile Gly Asp
    130                 135                 140

Val Ala Lys Lys Leu Gly Glu Met Trp Asn Asn Thr Ala Ala Asp Asp
145                 150                 155                 160

Lys Gln Pro Tyr Glu Lys Lys Ala Ala Lys Leu Lys Glu Lys Tyr Glu
                165                 170                 175

Lys Asp Ile Ala Ala Tyr Arg Ala Lys Gly Lys Pro Asp Ala Ala Lys
            180                 185                 190

Lys Gly Val Val Lys Ala Glu Lys Ala Lys Lys Lys Glu Glu Glu Glu
        195                 200                 205

Asp Asp Glu Glu Asp Glu Glu Asp Glu Glu Glu Glu Glu Glu Glu Glu
    210                 215                 220

Asp Glu Asp Glu Glu Glu Asp Asp Asp Glu Xaa Ala Ser
225                 230                 235
```

```
<210> SEQ ID NO 18
<211> LENGTH: 428
<212> TYPE: PRT
```

-continued

<213> ORGANISM: Homo sapiens

<400> SEQUENCE: 18

```
Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly His Phe Pro Pro
        115                 120                 125

Pro Thr Ile Gln Leu Leu Cys Leu Val Ser Gly Tyr Thr Pro Gly Thr
    130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
    290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
        355                 360                 365

Ala Arg His Ser Thr Thr Gln Pro Arg Lys Thr Lys Gly Ser Gly Phe
    370                 375                 380

Phe Val Phe Ser Arg Leu Glu Val Thr Arg Ala Glu Trp Glu Gln Lys
385                 390                 395                 400
```

Asp Glu Phe Ile Cys Arg Ala Val His Glu Ala Ala Ser Pro Ser Gln
            405                 410                 415

Thr Val Gln Arg Ala Val Ser Val Asn Pro Gly Lys
            420                 425

<210> SEQ ID NO 19
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
ctcgagatgg actggacatg gattctcttt ctagtggccg cagccacaag ggtccactcc      60
atgggcaaag gagatcctaa aaagccgaga ggcaaaatgt cctcatatgc attctttgtg     120
caaacttgcc gggaggagca agaagaag cacccggatg ctgcagtcaa cttcgctgag     180
ttcgcaaaga agtgcgctga gaggtggaag accatggcag ctaaagaaaa ggggaaattt     240
gaagatatgg caaaggctga caaggctcgt tatgaaagag aaatgaaaac ctacatcccc     300
cccaaagggg agaccaaaaa gaagttcaag acccccaatg cacccaagag gcctccttcg     360
gccttcttct tgttctgttc tgagtaccgc cccaaaatca aggcgagca tcctggctta     420 tccattggtg atgttgcaaa gaaactagga gagatgtgga acaacactgc agcagatgac     480
aagcagccct atgagaagaa agctgccaag ctgaaggaga agtatgagaa ggatattgct     540
gcctacagag ctaaaggaaa acctgatgca gcgaaaaagg gggtggtcaa ggctgaaaag     600
gcgaagaaaa agaaggaaga ggaagatgat gaggaggatg aagaggatga ggaagaggag     660
gaagaagagg aagacgaaga tgaagaagaa gatgatgatg atgaagaagc tagc           714

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Lys Lys His Pro Asp Ala Ala Val Asn Phe Ala Glu Phe Ala Lys
1               5                   10                  15

Lys Cys Ala Glu Arg Trp Lys Thr Met Ala Ala
            20                  25

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Lys Ala Lys Lys Lys Lys
1               5

<210> SEQ ID NO 22
<211> LENGTH: 215
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 22

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ala Val Asn Phe Ala Glu Phe Ala Lys Lys Cys Ala Glu Arg
        35                  40                  45

Trp Lys Thr Met Ala Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Glu Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ala Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

Glu Glu Asp Asp Asp Asp Glu
    210                 215

<210> SEQ ID NO 23
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (216)..(216)
<223> OTHER INFORMATION: Any amino acid

<400> SEQUENCE: 23

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ala Val Asn Phe Ala Glu Phe Ala Lys Lys Cys Ala Glu Arg
        35                  40                  45

Trp Lys Thr Met Ala Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Glu Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ala Lys Lys Lys Glu Glu Glu Asp Asp Glu Glu
                180                 185                 190

Asp Glu Glu Asp Glu Glu Glu Glu Glu Glu Asp Glu Asp Glu
        195                 200                 205

Glu Glu Asp Asp Asp Asp Glu Xaa Ala Ser
        210                 215

<210> SEQ ID NO 24
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Trp Thr Trp Ile Leu Phe Leu Val Ala Ala Thr Arg Val
1               5                   10                  15

His Ser Met Gly Lys Gly Asp Pro Lys Lys Pro Arg Gly Lys Met Ser
                20                  25                  30

Ser Tyr Ala Phe Phe Val Gln Thr Cys Arg Glu Glu His Lys Lys Lys
            35                  40                  45

His Pro Asp Ala Ala Val Asn Phe Ala Glu Phe Ala Lys Lys Cys Ala
        50                  55                  60

Glu Arg Trp Lys Thr Met Ala Ala Lys Glu Lys Gly Lys Phe Glu Asp
65                  70                  75                  80

Met Ala Lys Ala Asp Lys Ala Arg Tyr Glu Arg Glu Met Lys Thr Tyr
                85                  90                  95

Ile Pro Pro Lys Gly Glu Thr Lys Lys Lys Phe Lys Asp Pro Asn Ala
                100                 105                 110

Pro Lys Arg Pro Pro Ser Ala Phe Phe Leu Phe Cys Ser Glu Tyr Arg
            115                 120                 125

Pro Lys Ile Lys Gly Glu His Pro Gly Leu Ser Ile Gly Asp Val Ala
        130                 135                 140

Lys Lys Leu Gly Glu Met Trp Asn Asn Thr Ala Ala Asp Asp Lys Gln
145                 150                 155                 160

Pro Tyr Glu Lys Lys Ala Ala Lys Leu Lys Glu Lys Tyr Glu Lys Asp
                165                 170                 175

Ile Ala Ala Tyr Arg Ala Lys Gly Lys Pro Asp Ala Ala Lys Lys Gly
                180                 185                 190

Val Val Lys Ala Glu Lys Ala Lys Lys Lys Glu Glu Glu Asp Asp
            195                 200                 205

Glu Glu Asp Glu Glu Asp Glu Glu Glu Glu Glu Glu Asp Glu
        210                 215                 220

Asp Glu Glu Glu Asp Asp Asp Asp Glu
225                 230

```
<210> SEQ ID NO 25
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (234)..(234)
<223> OTHER INFORMATION: Any amino acid

<400> SEQUENCE: 25

Met Asp Trp Thr Trp Ile Leu Phe Leu Val Ala Ala Thr Arg Val
1               5                   10                  15

His Ser Met Gly Lys Gly Asp Pro Lys Lys Pro Arg Gly Lys Met Ser
            20                  25                  30

Ser Tyr Ala Phe Phe Val Gln Thr Cys Arg Glu Glu His Lys Lys Lys
        35                  40                  45

His Pro Asp Ala Ala Val Asn Phe Ala Glu Phe Ala Lys Lys Cys Ala
    50                  55                  60

Glu Arg Trp Lys Thr Met Ala Ala Lys Gly Lys Gly Lys Phe Glu Asp
65                  70                  75                  80

Met Ala Lys Ala Asp Lys Ala Arg Tyr Glu Arg Glu Met Lys Thr Tyr
                85                  90                  95

Ile Pro Pro Lys Gly Glu Thr Lys Lys Lys Glu Lys Asp Pro Asn Ala
            100                 105                 110

Pro Lys Arg Pro Pro Ser Ala Phe Phe Leu Phe Cys Ser Glu Tyr Arg
        115                 120                 125

Pro Lys Ile Lys Gly Glu His Pro Gly Leu Ser Ile Gly Asp Val Ala
    130                 135                 140

Lys Lys Leu Gly Glu Met Trp Asn Asn Thr Ala Ala Asp Asp Lys Gln
145                 150                 155                 160

Pro Tyr Glu Lys Lys Ala Ala Lys Leu Lys Glu Lys Tyr Glu Lys Asp
                165                 170                 175

Ile Ala Ala Tyr Arg Ala Lys Gly Lys Pro Asp Ala Ala Lys Lys Gly
            180                 185                 190

Val Val Lys Ala Glu Lys Ala Lys Lys Lys Glu Glu Glu Asp Asp
        195                 200                 205

Glu Glu Asp Glu Glu Asp Glu Glu Glu Glu Glu Glu Glu Asp Glu
    210                 215                 220

Asp Glu Glu Glu Asp Asp Asp Glu Xaa Ala Ser
225                 230                 235
```

HIGH MOBILITY GROUP BOX I MUTANT

GRANT INFORMATION

This disclosure was made with government support under CA140215 awarded by the National Institutes of Health. The government has certain rights in the disclosure.

INCORPORATION BY REFERENCE

All publications, patents, patent applications, and NCBI accession numbers mentioned in this specification are herein incorporated by reference to the same extent as if each individual publication, patent, or patent application was specifically and individually indicated to be incorporated by reference, and as if set forth in their entireties. In the event of a conflict between a term as used herein and the term as defined in the incorporated reference, the definition of this disclosure controls.

CROSS-REFERENCE

This application claims the benefit of U.S. Provisional Application No. 62/397,523 filed Sep. 21, 2016, which is incorporated by reference herein in its entirety.

SUMMARY

One embodiment provides an oncolytic vaccinia virus comprising an exogenous nucleic acid that codes for a variant HMGB1, wherein the exogenous nucleic acid comprises a nucleotide sequence that is at least about 80% homologous to SEQ ID NO: 13, or a fragment thereof. In some embodiments, the exogenous nucleic acid that codes for the variant HMGB1, wherein the exogenous nucleic acid comprises a nucleotide sequence that is at least about 85%, at least about 90%, at least about 95%, at least about 96%, at least about 97%, at least about 98%, at least about 99%, or 100% homologous to SEQ ID NO: 13, or a fragment thereof. In some embodiments, the oncolytic vaccinia virus comprising the exogenous nucleic acid that codes for the variant HMGB1, wherein the variant HMGB1 comprises an amino acid sequence that is at least about 85%, at least about 90%, at least about 95%, at least about 96%, at least about 97%, at least about 98%, at least about 99%, or 100% homologous to SEQ ID NO: 15, or a fragment thereof. In some embodiments, the oncolytic vaccinia virus comprising the exogenous nucleic acid that codes for the variant HMGB1, wherein the variant HMGB1 comprises at least one of residues 21-74, 109-128, and 170-203 of SEQ ID NO: 15. In some embodiments, the oncolytic vaccinia virus the exogenous nucleic acid that codes for the variant HMGB1, wherein the variant HMGB1 comprises residues 21-74, 109-128, and 170-203 of SEQ ID NO: 15. In some embodiments, the oncolytic vaccinia virus comprising the exogenous nucleic acid that codes for the variant HMGB1, wherein the variant HMGB1 does not comprise residues 1-20 of SEQ ID NO: 15.

One embodiment provides an oncolytic vaccinia virus comprising an exogenous nucleic acid that codes for a variant HMGB1, wherein the variant HMGB1 comprises a mutation in its first (NLS1), the second nuclear localization signal (NLS2), or any combinations thereof. In some embodiments, the oncolytic vaccinia virus comprising the exogenous nucleic acid that codes for the variant HMGB1, wherein the variant HMGB1 further comprises a mutation in boxA, boxB, or any combinations thereof. In some embodiments, the oncolytic vaccinia virus comprising the exogenous nucleic acid that codes for the variant HMGB1, wherein the variant HMGB1 comprises an amino acid sequence at least about 85%, at least about 90%, at least about 95%, at least about 96%, at least about 97%, at least about 98%, at least about 99%, or 100% homologous to SEQ ID NO: 15, or a fragment thereof. In some embodiments, the oncolytic vaccinia virus comprising the exogenous nucleic acid that codes for the variant HMGB1, wherein the HMGB1 variant comprises cysteine residues at positions 43 and 65 of SEQ ID NO: 15. In some embodiments, the oncolytic vaccinia virus comprising the exogenous nucleic acid that codes for the variant HMGB1, wherein the HMGB1 variant comprises at least one of residues 21-74, 109-128, and 170-203 of SEQ ID NO: 15. In some embodiments, the oncolytic vaccinia virus comprising the exogenous nucleic acid that codes for the variant HMGB1, wherein said HMGB1 variant comprises residues 21-74, and 109-128 or 170-203 of SEQ ID NO: 15. In some embodiments, the oncolytic vaccinia virus comprising the exogenous nucleic acid that codes for the variant HMGB1, wherein the variant HMGB1 does not comprise residues 1-20 of SEQ ID NO: 15. In some embodiments, the oncolytic vaccinia virus comprising the exogenous nucleic acid sequence that codes for the variant HMGB1, wherein said nucleic acid sequence is at least about 80%, at least about 85%, at least about 90%, at least about 95%, at least about 96%, at least about 97%, at least about 98%, at least about 99%, or 100% to SEQ ID NO: 13, or a fragment thereof. In some embodiments, the oncolytic vaccinia virus comprising an exogenous nucleic acid sequence that codes for an antibody or an antigen binding fragment thereof operably linked to the exogenous nucleic acid sequence that codes for the variant HMGB1. In some embodiments, the oncolytic vaccinia virus further comprising an exogenous nucleic acid sequence that codes for a hyaluronidase operably linked to the exogenous nucleic acid sequence that codes for the variant HMGB1. In some embodiments, the oncolytic vaccinia virus comprising the exogenous nucleic acid that codes for the variant HMGB1 comprising the mutation in NLS1, wherein the mutation in NLS1 promotes cytoplasmic re-location of the variant HMGB1. In some embodiments, the oncolytic vaccinia virus comprising the exogenous nucleic acid that codes for the variant HMGB1 comprising the mutation in NLS2, wherein the mutation in NLS2 promotes cytoplasmic re-location of the variant HMGB1. In some embodiments, the oncolytic vaccinia virus comprising the exogenous nucleic acid that codes for the variant HMGB1 comprising the mutations in NLS1 and NLS2, wherein the mutations in NLS1 and NLS2 promote cytoplasmic re-location of the variant HMGB1.

One embodiment provides an oncolytic vaccinia virus comprising an exogenous nucleic acid that codes for a variant HMGB1, wherein the variant HMGB1 is less than or equal to 95% homologous to human HMGB1 (SEQ ID NO: 16). In some embodiments, the oncolytic vaccinia virus comprising the exogenous nucleic acid that codes for the variant HMGB1, wherein the variant HMGB1 comprises at least one of residues 1-85, 89-108, and 150-183 of SEQ ID NO: 16. In some embodiments, the variant HMGB1 comprises residues 1-85 of SEQ ID NO: 16. In some embodiments, the oncolytic vaccinia virus comprising the exogenous nucleic acid that codes for the variant HMGB1, wherein the variant HMGB1 comprises residues 89-108 of SEQ ID NO: 16. In some embodiments, the oncolytic vaccinia virus comprising the exogenous nucleic acid that codes for the variant HMGB1, wherein the variant HMGB1 comprises residues 150-183 of SEQ ID NO: 16. In some embodiments, the oncolytic vaccinia virus comprising the exogenous nucleic acid that codes for the variant HMGB1, wherein the variant HMGB1 comprises residues 1-85, 89-108, and 150-183 of SEQ ID NO: 16. In some embodiments, the oncolytic vaccinia virus comprising the exogenous nucleic acid that codes for the variant HMGB1 wherein the variant HMGB1 comprises mutations at one or more of residues 35, 42, 89, 181, 189, and 202 of SEQ ID NO: 16. In some embodiments, the oncolytic vaccinia virus comprising the exogenous nucleic acid that codes for the variant HMGB1 wherein the variant HMGB1 comprises mutations at residues 35, 42, 89, 181, 189, and 202 of SEQ ID NO: 16.

One embodiment provides an oncolytic vaccinia virus comprising an exogenous nucleic acid that codes for a variant HMGB1, wherein the variant HMGB1 comprises residues 23, 45, 89-108, and 150-183 of SEQ ID NO: 16, and wherein the variant HMGB1 comprises an amino acid sequence that is less than or equal to 95% homologous to SEQ ID NO: 16. In some embodiments, the oncolytic vaccinia virus comprising the exogenous nucleic acid that codes for the variant HMGB1, wherein the variant HMGB1 comprises residues 23-45, 89-108, 150-183 of SEQ ID NO: 16. In some embodiments, the variant HMGB1 comprises mutations at one or more of residues 35, 42, 89, 181, 189, and 202 of SEQ ID NO: 16. In some embodiments, the variant HMGB1 comprises mutations at residues 35, 42, 89, 181, 189, and 202 of SEQ ID NO: 16.

One embodiment provides an oncolytic vaccinia virus comprising an exogenous nucleic acid that codes for a variant HMGB1, wherein the exogenous nucleic acid comprises a nucleotide sequence that is at least about 80% homologous to SEQ ID NO: 14, or a fragment thereof. In some embodiments, the oncolytic vaccinia virus comprising the exogenous nucleic acid that codes for the variant HMGB1, wherein the exogenous nucleic acid comprises a nucleotide sequence that is at least about 85%, at least about 90%, at least about 95%, at least about 96%, at least about 97%, at least about 98%, at least about 99%, or 100% homologous to SEQ ID NO: 14, or the fragment thereof. In some embodiments, the oncolytic vaccinia virus comprising the exogenous nucleic acid that codes for the variant HMGB1, wherein the variant HMGB1 comprises an amino acid sequence that is at least about 85%, at least about 90%, at least about 95%, at least about 96%, at least about 97%, at least about 98%, at least about 99%, or 100% homologous to SEQ ID NO: 17, or a fragment thereof. In some embodiments, the oncolytic vaccinia virus comprising the exogenous nucleic acid that codes for the variant HMGB1, wherein the variant HMGB1 comprises at least one of residues 21-74, 109-128, and 170-203 of SEQ ID NO: 17. In some embodiments, the oncolytic vaccinia virus comprising the exogenous nucleic acid that codes for the variant HMGB1, wherein the variant HMGB1 comprises residues 21-74, 109-128, and 170-203 of SEQ ID NO: 17. In some embodiments, the oncolytic vaccinia virus comprising the exogenous nucleic acid that codes for the variant HMGB1, wherein the variant HMGB1 does not comprise residues 1-20 of SEQ ID NO: 17.

One embodiment provides an oncolytic vaccinia virus comprising an exogenous nucleic acid that codes for a variant HMGB1, wherein the exogenous nucleic acid comprises a nucleotide sequence that is at least about 80% homologous to SEQ ID NO: 19, or a fragment thereof. In some embodiments, the oncolytic vaccinia virus comprising the exogenous nucleic acid that codes for the variant HMGB1, wherein the exogenous nucleic acid comprises a nucleotide sequence that is at least about 85%, at least about 90%, at least about 95%, at least about 96%, at least about 97%, at least about 98%, at least about 99%, or 100% homologous to SEQ ID NO: 14, or the fragment thereof. In some embodiments, the oncolytic vaccinia virus comprising the exogenous nucleic acid that codes for the variant HMGB1, wherein the variant HMGB1 comprises an amino acid sequence that is at least about 85%, at least about 90%, at least about 95%, at least about 96%, at least about 97%, at least about 98%, at least about 99%, or 100% homologous to SEQ ID NO: 17, or a fragment thereof. In some embodiments, the oncolytic vaccinia virus comprising the exogenous nucleic acid that codes for the variant HMGB1; wherein the variant HMGB1 comprises at least one of residues 21-74, 109-128, and 170-203 of SEQ ID NO: 17. In some embodiments, the oncolytic vaccinia virus comprising the exogenous nucleic acid that codes for the variant HMGB1, wherein the variant HMGB1 comprises residues 21-74, 109-128, and 170-203 of SEQ ID NO: 17. In some embodiments, the oncolytic vaccinia virus comprising the exogenous nucleic acid that codes for the variant HMGB1, wherein the variant HMGB1 does not comprise residues 1-20 of SEQ ID NO: 17. In some embodiments, the oncolytic vaccinia virus comprising the exogenous nucleic acid that codes for the variant HMGB1 comprising the mutation in NLS2, wherein the mutation in NLS2 promotes cytoplasmic re-location of the variant HMGB1. In some embodiments, the oncolytic vaccinia virus comprising the mutations in NLS1 and NLS2, wherein the mutations in NLS1 and NLS2 promotes cytoplasmic re-location of the variant HMGB1. In some embodiments, the variant HMGB1 expressed from the vaccinia virus is secreted into the cytoplasm. In some embodiments, expression of the variant HMGB1 from the vaccinia virus enhances cellular autophagy, compared to an otherwise identical vaccinia virus that lacks the exogenous nucleic acid coding for the variant HMGB1. In some embodiments, expression of the variant HMGB1 enhances tumor-specific replication of the vaccinia virus, compared to an otherwise identical vaccinia virus that lacks the exogenous nucleic acid coding for the variant HMGB1. In some embodiments, expression of the variant HMGB1 enhances cytotoxic immune response against a tumor cell infected by the vaccinia virus, compared to an otherwise identical vaccinia virus that lacks the exogenous nucleic acid coding for the variant HMGB1. In some embodiments, expression of the variant HMGB1 induces cytotoxic immune response against a tumor cell in the vicinity of a tumor cell infected by the vaccinia virus, wherein the tumor cell in the vicinity is not infected by the vaccinia virus. In some embodiments, the vaccinia virus comprises one or more deletions in its genome. In some embodiments, the oncolytic vaccinia virus comprising the exogenous nucleic acid that codes for the variant HMGB1, wherein the vaccinia virus comprises a thymidine kinase gene deletion and the exogenous nucleic acid is inserted into the thymidine kinase gene locus. In some embodiments, the oncolytic vaccinia virus comprising the exogenous nucleic acid that codes for the variant HMGB1, wherein the vaccinia virus comprises deletions of one or more virulence genes. In some embodiments, the oncolytic vaccinia virus is an extracellular enveloped virus (EEV). In some embodiments, the oncolytic vaccinia virus further expresses a hyaluronidase enzyme. In some embodiments, vaccinia virus expresses the hyaluronidase enzyme, and wherein the hyaluronidase enzyme increases the spread of the vaccinia virus in a tumor microenvironment, compared to the spread of an otherwise identical vaccinia virus that does not comprise the exogenous nucleic acid coding for the hyaluronidase enzyme operable linked to the exogenous nucleic acid coding for the variant HMGB1. In some embodiments, the vaccinia virus expresses the hyaluronidase enzyme, and wherein the hyaluronidase enzyme increases the spread of the vaccinia virus in a tumor microenvironment. In some embodiments, the oncolytic vaccinia virus the vaccinia virus further expresses a protein that stabilizes the variant HMGB1 in circulation. In some embodiments, the protein that stabilizes the variant HMGB1 in circulation is an immunoglobulin or a domain thereof. In some embodiments, the oncolytic vaccinia virus the immunoglobulin is IgE. In some embodiments, the immunoglobulin domain is an Fc domain. In some embodiments, the oncolytic vaccinia virus comprising the exogenous nucleic acid sequence that codes for the variant HMGB1, wherein the further exogenous nucleic acid sequence coding for the IgE is fused upstream to the variant HMGB1 coding sequence. In some embodiments, the oncolytic vaccinia virus further expresses an efflux pump blocker. In some embodiments, the oncolytic vaccinia virus further expresses a chemotherapy sensitizer. In some embodiments, the oncolytic vaccinia virus the virus comprises a modification that enhances sensitization to chemotherapy. In some embodiments, the oncolytic vaccinia virus comprises a modification that attracts chimeric antigen receptor T cells. In some embodiments, the oncolytic vaccinia virus enhances efficacy of a CAR T cell based therapy.

One embodiment provides an isolated polynucleotide that codes for a variant HMGB1, wherein the polynucleotide comprises a sequence that is at least 85% homologous to SEQ ID NO: 13, or a fragment thereof. In some embodiments, the polynucleotide codes for a variant HMGB1, wherein the variant HMGB1 comprises an amino acid sequence that is at least about 85%, at least about 90%, at least about 95%, at least about 96%, at least about 97%, at least about 98%, at least about 99%, or 100% homologous to SEQ ID NO: 15, or a fragment thereof. In some embodiments, the oncolytic vaccinia virus the variant HMGB1, wherein the variant HMGB1 comprises a mutation in its first (NLS1) or second nuclear localization signal (NLS2). In some embodiments, the variant HMGB1 further comprises a mutation in boxA or boxB. In some embodiments, the oncolytic vaccinia virus the variant HMGB1 further comprises mutations in boxA or boxB. In some embodiments, the variant HMGB1 comprises cysteine residues at positions 43 and 65 of SEQ ID NO: 15. In some embodiments, the variant HMGB1 comprises at least one of residues 21-74, 109-128, and 170-183 of SEQ ID NO: 15. In some embodiments, said HMGB1 variant comprises residues 21-105, 108-182, and 183-205 of SEQ ID NO: 15.

One embodiment provides a pharmaceutical composition comprising an oncolytic vaccinia virus as described in this disclosure or an isolated polynucleotide as described in this disclosure, a solubilizing agent, and an excipient. In some embodiments, the excipient comprises one or more of a buffering agent, a stabilizer, an antioxidant, a binder, a diluent, a dispersing agent, a rate controlling agent, a lubricant, a glidant, a disintegrant, a plasticizer, a preservative, or any combination thereof. In some embodiments, the excipient comprises disodium hydrogen phosphate dihydrate, sodium dihydrogen phosphate dihydrate, sodium chloride, myo-inositol, sorbitol, or any combination thereof. In some embodiments, the pharmaceutical composition does not comprise a preservative. In some embodiments, the pharmaceutical composition further comprises one or more of a preservative, a diluent, and a carrier. In some embodiments, the pharmaceutical composition further comprises an additional active ingredient or a salt thereof. In some embodiments, the solubilizing agent is sterile water. In some embodiments, the pharmaceutical composition further comprises an additional active ingredient, wherein the additional active ingredient is a further oncolytic virus.

One embodiment provides a process for producing an oncolytic vaccinia virus as described herein, the process comprising: (i) generating a modified vaccinia virus DNA vector by operably linking a vaccinia virus base nucleic acid sequence to the exogenous nucleic acid sequence in this disclosure; (ii) transfecting mammalian cells with the modified vaccinia virus DNA vector; (iii) culturing the mammalian cells in conditions suitable for viral replication; and (iv) harvesting the viral particles. In some embodiments, the mammalian cells comprise HeLa cells, 293 cells, or Vero cells. In some embodiments, the exogenous nucleic acid, as described in this disclosure, in the modified vaccinia virus DNA vector promotes a population of viral particles predominantly containing extracellular enveloped viruses (EEV). In some embodiments, the exogenous nucleic acid, as described in this disclosure, in the modified vaccinia virus DNA vector results in a higher titer in at least one of HeLa cells and 293 cells, compared to an otherwise identical vaccinia virus DNA vector which does not comprise the exogenous nucleic acid according to this disclosure.

One embodiment provides a method of treating a cancer, comprising administering to a subject a therapeutically effective amount of an oncolytic vaccinia virus as described in this disclosure or a pharmaceutical composition according to this disclosure. In some embodiments, the method comprises administration of the therapeutically effective amount of an oncolytic vaccinia virus as described in this disclosure or a pharmaceutical composition as described in this disclosure, wherein the cancer is a solid tumor, a leukemia, or a lymphoma. One embodiment provides a method of treating a tumor, comprising administering to a subject a therapeutically effective amount of an oncolytic vaccinia virus as described in this disclosure or a pharmaceutical composition as described in this disclosure. In some embodiments, the method comprises administration of the therapeutically effective amount of an oncolytic vaccinia virus as described in this disclosure or a pharmaceutical composition as described in this disclosure, wherein the tumor is a solid tumor, a leukemia, or a lymphoma. In some embodiments, the method comprises administering to the subject in need thereof the a therapeutically effective amount of an oncolytic vaccinia virus as described in this disclosure or a pharmaceutical composition as described in this disclosure.

One embodiment provides a method of treating a tumor comprising high bioavailability of fatty acids, comprising administering an oncolytic vaccinia virus as described in this disclosure or a pharmaceutical composition as described in this disclosure, wherein the vaccinia virus demonstrates increased tumor selective replication in the tumor comprising the high bioavailability of free fatty acids. One embodiment provides a method of treating an obese cancer patient, comprising administering an oncolytic vaccinia virus as described in this disclosure or a pharmaceutical composition according to as described in this disclosure, wherein the vaccinia virus demonstrates increased tumor selective replication in the obese cancer patient. In some embodiments, the increased tumor selective replication is relative to a tumor selective replication of an otherwise identical vaccinia virus that does not comprise the exogenous nucleic acid sequence coding for the variant HMGB1. In some embodiments, the increased tumor selective replication is relative to the tumor selective replication of the vaccinia virus in a non-obese cancer patient. In some embodiments, the vaccinia virus produces an increased proportion of EEV in the obese cancer patient. In some embodiments, the increased proportion of EEV in the obese cancer patient is relative to the proportion of EEV produced by an otherwise identical vaccinia virus that does not comprise the exogenous nucleic acid sequence coding for the variant HMGB1. In some embodiments, the increased proportion of EEV in the obese cancer patient is relative to the proportion of EEV produced by the vaccinia virus in a non-obese cancer patient.

One embodiment provides a method of reducing a likelihood of cancer relapse after chemotherapy, comprising administering an oncolytic vaccinia virus as described in this disclosure, or a pharmaceutical formulation as described in this disclosure.

One embodiment provides a method of treatment, comprising administering an oncolytic vaccinia virus as described in this disclosure, or a pharmaceutical formulation as described in this disclosure to a subject who has failed a prior treatment comprising an immunotherapy.

One embodiment provides a method of treatment, comprising administering an oncolytic vaccinia virus as described in this disclosure, or a pharmaceutical formulation as described in this disclosure to a subject who has relapse of cancer after chemotherapy.

One embodiment provides a method of treatment, comprising administering an oncolytic vaccinia virus as described in this disclosure, or a pharmaceutical formulation as described in this disclosure to a subject who has a peritoneal cancer. In some embodiments, the subject is obese. In some embodiments, the method comprises administration of an oncolytic vaccinia virus or a pharmaceutical formulation as described herein, wherein the method further comprises administration of a further therapy. In some embodiments, the method comprises administration of the further therapy in combination with an oncolytic vaccinia virus or a pharmaceutical formulation as described herein, wherein the further therapy comprises chemotherapy, radiation, oncolytic viral therapy with an additional virus, treatment with immunomodulatory proteins, a CAR T cellular therapy, an anti-cancer agent, or any combinations thereof. In some embodiments, the further therapy comprises chemotherapy. In some embodiments, the combination of administration of an oncolytic vaccinia virus as described herein or a pharmaceutical formulation as described herein, and chemotherapy, results in a synergistic effect, compared to a combination of the chemotherapy and an otherwise identical vaccinia virus that does not comprise the exogenous nucleic acid that codes for a variant HMGB1 as described herein. In some embodiments, the chemotherapy in combination with an oncolytic vaccinia virus or a pharmaceutical formulation as described herein is administered at a lower dose than a chemotherapy in combination with an otherwise identical vaccinia virus that does not comprise the exogenous nucleic acid that codes for a variant HMGB1 as described herein. In some embodiments, the method comprises administration of the further therapy, wherein the further therapy is administered concurrently or sequentially. In some embodiments, the method comprises sequential administration of the further therapy, wherein the further therapy is administered prior to administering an oncolytic vaccinia virus as described in this disclosure, or a pharmaceutical composition as described in this disclosure. In some embodiments, the method comprises sequential administration of the further therapy, wherein the further therapy is administered after administering an oncolytic vaccinia virus as described in this disclosure, or a pharmaceutical composition as described in this disclosure. One embodiment provides a method of producing a toxic effect in cancer cells, the method comprising administering to a population of cancer cells a therapeutically effective amount of an oncolytic vaccinia virus, as described in this disclosure, or a pharmaceutical composition as described in this disclosure. In some embodiments, the method comprises the administration of the therapeutically effective amount of an oncolytic vaccinia virus as described in this disclosure, or a pharmaceutical composition as described in this disclosure, wherein not every cancer cell in the population of cancer cells is infected with the oncolytic vaccinia virus. In some embodiments, the growth of a non-infected cancer cell is inhibited without direct infection of the oncolytic vaccinia virus. In some embodiments, the cytotoxic immune response in a non-infected cancer cell is induced without direct infection by the oncolytic vaccinia virus. One embodiment provides a method for drug delivery comprising introducing into a tumor of a subject an oncolytic vaccinia vector as described in this disclosure, or a pharmaceutical formulation as described in this disclosure. In some embodiments, the drug comprises a nanoparticle conjugated to a tumor receptor ligand. One embodiment provides a method for treating cancer in a subject, comprising administering cells infected with an oncolytic vaccinia virus as described in this disclosure. In some embodiments, the method increases efficacy of oncolytic vaccinia virus based cancer therapy. In some embodiments, the method comprises administration of an oncolytic vaccinia virus as described in this disclosure or a pharmaceutical composition as described in this disclosure, wherein the oncolytic vaccinia virus or the pharmaceutical composition is administered at a dosage that comprises about $10^6$ PFU/mL to about $10^{10}$ PFU/mL of the oncolytic vaccinia virus. In some embodiments, the method comprises administration of an oncolytic vaccinia virus according to this disclosure or a pharmaceutical composition as described in this disclosure, wherein the oncolytic vaccinia virus or the pharmaceutical composition is administered at a dosage that comprises about $5\times10^9$ PFU/mL of the oncolytic vaccinia virus. In some embodiments, the method comprises the administration of the oncolytic vaccinia virus according to this disclosure or a pharmaceutical composition as described in this disclosure, wherein the oncolytic vaccinia virus or the pharmaceutical composition is administered, independently, in an initial dose for a first period of time, an intermediate dose for a second period of time, and a high dose for a third period of time. In some embodiments, the method comprises administration of the initial, the intermediate, and the high dose, independently, wherein the initial dose is lower than the intermediate dose and the intermediate dose is lower than the high dose. In some embodiments, the first, second, and third periods of time are each from about 1 week to about 3 weeks. In some embodiments, the method comprises administering the oncolytic vaccinia virus as described in this disclosure, or the pharmaceutical composition as described in this disclosure, wherein the oncolytic vaccinia virus and the pharmaceutical composition independently comprises a liquid dosage form that is administered at a volume of about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL. In some embodiments, the method comprises administering the oncolytic vaccinia virus as described in this disclosure, or the pharmaceutical composition as described in this disclosure, wherein the oncolytic vaccinia virus or the pharmaceutical composition is administered in a liquid dosage form, a solid dosage form, an inhalable dosage form, an intranasal dosage form, in a liposomal formulation, a dosage form comprising nanoparticles, a dosage form comprising microparticles, a polymeric dosage form, or any combinations thereof. In some embodiments, the method comprises administering the oncolytic vaccinia virus as described in this disclosure, or the pharmaceutical composition as described in this disclosure, wherein the oncolytic vaccinia virus or the pharmaceutical composition is administered for a duration of about 1 week, about 2 week, about 3 weeks, about 4 weeks, about 6 weeks, about 7 weeks, about 8 weeks, about 9 weeks, about 10, weeks, or about 12 weeks. In some embodiments, the method comprises administering the oncolytic vaccinia virus as described in this disclosure, or the pharmaceutical composition as described in this disclosure, wherein the oncolytic vaccinia virus or the pharmaceutical composition is administered once daily, twice daily, once every week, once every two weeks, or once every three weeks. In some embodiments, the method comprises administering the oncolytic vaccinia virus as described in this disclosure, or the pharmaceutical composition as described in this disclosure, wherein the oncolytic vaccinia virus or the pharmaceutical composition is administered intravenously, intraperitoneally, or by an intratumoral injection. In some embodiments, the method comprises administering the oncolytic vaccinia virus as described in this disclosure, or the pharmaceutical composition as described in this disclosure, wherein the vaccinia virus or the pharmaceutical formulation is administered as a bolus injection or a slow infusion. In some embodiments, the method comprises administering the oncolytic vaccinia virus as described in this disclosure, or the pharmaceutical composition as described in this disclosure, wherein the administration of the oncolytic vaccinia virus or the pharmaceutical composition results in a first peak viral load after about 1 hour to about 3 days and a second peak viral load after about 3 days to about 10 days from administration of a first dose. In some embodiments, the method comprises administration of the further therapy, wherein the further therapy is administered for a duration of about 1 week, about 2 week, about 3 weeks, about 4 weeks, about 6 weeks, about 7 weeks, about 8 weeks, about 9 weeks, about 10, weeks, or about 12 weeks. In some embodiments, the method comprises administration of the further therapy, wherein the further therapy is administered once daily, once every week, once every two weeks, or once every three weeks. In some embodiments, the method comprises administration of the further therapy, wherein the further therapy is administered in a liquid dosage form, a solid dosage form, an inhalable dosage form, an intranasal dosage form, in a liposomal formulation, a dosage form comprising nanoparticles, a dosage form comprising microparticles, a polymeric dosage form, or any combinations thereof. In some embodiments, the method comprises administration of the further therapy, wherein the further therapy is administered orally, intravenously, by an intratumoral injection, or by radiation. In some embodiments, the method comprises administration of the oncolytic vaccinia virus as described in this disclosure, or the pharmaceutical composition as described in this disclosure to a subject in need thereof, wherein the subject is human. In some embodiments, the method comprises administration of the oncolytic vaccinia virus as described in this disclosure, or the pharmaceutical composition as described in this disclosure to the subject in need thereof, wherein prior to administration of the oncolytic vaccinia virus or the pharmaceutical composition the subject has been diagnosed with a cancer or a tumor. In some embodiments, the method comprises the administration of the oncolytic vaccinia virus as described in this disclosure, or the pharmaceutical composition as described in this disclosure to the subject in need thereof, wherein prior to administration of the oncolytic vaccinia virus or the pharmaceutical composition the subject is diagnosed with a cancer or a tumor, and wherein the subject is obese. In some embodiments, the method comprises administration of the oncolytic vaccinia virus as described in this disclosure, or the pharmaceutical composition as described in this disclosure to the subject in need thereof in combination with the further therapy, wherein prior to administration of the oncolytic vaccinia virus or the pharmaceutical composition or the further therapy the subject has been diagnosed with a cancer or a tumor. In some embodiments, the method comprises administration of the oncolytic vaccinia virus as described in this disclosure, or the pharmaceutical composition as described in this disclosure to the subject in need thereof in combination with the further therapy, wherein prior to administration of the oncolytic vaccinia virus or the pharmaceutical composition the subject is diagnosed with a cancer or a tumor, and wherein the subject is obese. In some embodiments, the subject is administered a ketogenic diet prior to, concurrently, or following administration of the oncolytic vaccinia virus as described in this disclosure, or the pharmaceutical composition as described in this disclosure. In some embodiments, the subject is on short term fasting prior to, concurrently, or following administration of the oncolytic vaccinia virus as described in this disclosure, or the pharmaceutical composition as described in this disclosure.

One embodiment provides a modified virus comprising an exogenous nucleic acid that codes for a variant HMGB1, wherein the exogenous nucleic acid comprises a nucleotide sequence that is at least about 80% homologous to SEQ ID NO: 13, or a fragment thereof. One embodiment provides a modified virus comprising an exogenous nucleic acid that codes for a variant HMGB1, wherein the variant HMGB1 comprises a mutation in its first nuclear localization signal (NLS1), second nuclear localization signal (NLS2), or any combinations thereof. One embodiment provides a modified virus comprising an exogenous nucleic acid that codes for a variant HMGB1, wherein the variant HMGB1 is less than or equal to 95% homologous to human HMGB1 (SEQ ID NO: 16). One embodiment provides a modified virus comprising an exogenous nucleic acid that codes for a variant HMGB1, wherein the variant HMGB1 comprises at least one of residues 23, 45, 89-108, and 150-183 of SEQ ID NO: 16, and wherein the variant HMGB1 comprises an amino acid sequence that is less than or equal to 95% homologous to SEQ ID NO: 16. One embodiment provides a modified virus comprising an exogenous nucleic acid that codes for a variant HMGB1, wherein the exogenous nucleic acid comprises a nucleotide sequence that is at least about 80% homologous to SEQ ID NO: 14, or a fragment thereof. One embodiment provides a modified virus comprising an exogenous nucleic acid that codes for a variant HMGB1, wherein the exogenous nucleic acid comprises a nucleotide sequence that is at least about 80% homologous to SEQ ID NO: 19, or a fragment thereof. In some embodiments, the modified virus comprises Herpes Simplex Virus (HSV), Adenovirus, Polio virus, VSV, Coxsackievirus, Reovirus, Lentivirus, Adeno-associated virus (AAV), Measles virus, Maraba virus, Newcastle disease (NDV), Seneca valley virus, Mengovirus, or Myxomavir.

In some embodiments, the oncolytic vaccinia virus comprises a NLS1 and a NLS2, wherein NLS1 comprises SEQ ID NO: 20 and NLS2 comprise SEQ ID NO: 21.

BRIEF DESCRIPTION OF THE DRAWINGS

The novel features of the disclosure are set forth with particularity in the appended claims. A better understanding of the features and advantages of this disclosure will be obtained by reference to the following detailed description that sets forth illustrative embodiments, in which the principles of this disclosure are utilized, and the accompanying drawings of which.

FIG. 1 shows the structure and expression of an exemplary variant HMGB1 according to this disclosure. FIG. 1 (a) is an illustration of an exemplary variant HMGB1 protein (mHMGB1mut) with mutations in the first nuclear localization signal (NLS1) region located in Box A, and in the second nuclear localization signal (NLS2) region between Box B and the acid C-tail; and an IgE sequence attached to the 5' end of the protein, as compared to a HMGB1 wildtype protein (mHMGB1 wt). FIG. 1 (b) is an illustration of the genome of a vaccinia virus comprising a coding sequence for the variant HMGB1 protein (mHMGB1mut).

FIG. 1 (c) is an image of a gel electrophoresis showing the difference in molecular weight between HMGB1 wildtype and HMGB1mut and demonstrating expression of HMGB1mut from a strain of vaccinia virus. FIG. 1 (d) is a graph showing the amount of HMGB protein secreted after infection of the indicated cells (Renca and 4T1) with a negative control, TK (control oncolytic vaccinia virus with a deletion in the viral thymidine kinase gene) or TK-HMGB1mut (oncolytic vaccinia virus with a deletion in the viral thymine kinase gene and insertion of a coding sequence for expression of the exemplary variant HMGB1, HMGB1mut).

FIG. 2 shows effect of treatment with vaccinia virus containing the exemplary variant HMGB1 (HMGB1 mut) on tumor growth. FIGS. 2 (a) and (b) are graphs showing the relative tumor size in mice bearing Renca or MC38 tumors, after being injected with PBS, TK (control oncolytic vaccinia virus with a deletion in the viral thymidine kinase gene), or TK-HMGB1mut (oncolytic vaccinia virus with a deletion in the viral thymine kinase gene and insertion of a coding sequence for expression of the exemplary variant HMGB, HMGB1mut).

FIG. 3 shows the effect of treatment with vaccinia virus containing the exemplary variant HMGB1 (HMGB1mut) on the cellular immune response in four different cell lines, including Renca, MC38, 4T1, and mouse embryonic fibroblasts (MEFs), and on tumor growth in mice. Shown are levels of (a) phospho-inhibitor of nuclear factor kappa-B kinase subunit beta (pIKKb); (b) interleukin 6 (IL-6); (c) interferon gamma-induced protein 10 (IP-10); (d) tumor necrosis factor alpha (TNF-α); and (e) interferon beta (IFN-γ) in cell lines treated with control (PBS), TK (control oncolytic vaccinia virus with a deletion in the viral thymidine kinase gene), or TK-HMGB1mut (oncolytic vaccinia virus with a deletion in the viral thymine kinase gene and insertion of a coding sequence for expression of the exemplary variant HMGB, HMGB mut). FIG. 3 (f) is a graph showing the cellular immune response to vaccinia virus evaluated by IFN-γ ELISpot assay in mice bearing tumors and treated with PBS, TK, or TK-HMGB1mut. FIG. 3 (g) is a graph showing the relative tumor size in mice bearing implanted tumors after treatment with PBS, TK, or TK-HMGB1.

FIG. 4 shows the effect of treatment with vaccinia virus containing the exemplary variant HMGB1 (HMGB1mut) on viral replication and tumor cell survival rate in cell lines and tumor-bearing mice. FIG. 4 (a) contains graphs showing increased viral replication in Renca, MC38, and 4T1 cells with TK-HMGB1mut expression compared with TK expression from vaccinia virus. FIG. 4 (b) includes graphs illustrating the survival rate of Renca and MC38 cells following treatment with TK or TK-HMGB1mut. FIG. 4 (c) shows viral gene expression in mice bearing Renca cell-derived tumors treated with TK or TK-HMGB1mut. FIG. 4 (d) contains graphs illustrating the survival rate of 4T1 cells and MEFs following treatment with TK or TK-HMGB mut. FIG. 4 (e) shows viral gene expression in mice bearing MC38 cell-derived tumors treated with TK or TK-HMGB1mut. FIG. 4 (f) illustrates viral replication in vivo in the whole body and (g) in the tumor of an immune-deficient mouse treated with TK or TK-HMGB1mut.

FIG. 5 shows the effect of treatment with vaccinia virus containing the exemplary variant HMGB1 (HMGB1mut) on autophagy and viral replication in cell lines. Light chain 3 (LC3) is a soluble protein used as a marker of autophagy. FIG. 5 (a) is a graph showing the percentage of LC3+ cells in a cell line treated with PBS, TK, or TK-HMGB1mut. FIG. 5 (b) contains graphs showing viral replication in Renca, MC38, and 4T1 cell lines treated with TK or TK-HMGB1mut alone or in combination with inhibitors of autophagic vacuole maturation, including bafilomycin A or LY294002.

FIG. 6 shows the effects of Atg5 knockdown and fatty acids on viral replication in cell lines and tumor-bearing mice. FIG. 6 (a) is a graph showing viral replication as a function of time in HCT 116 cells transfected without or with siRNA targeting Atg5. FIG. 6 (b) is a graph showing viral replication as a function of time in MDA-MB-231 cells treated without or with cerulenin, a fatty acid inhibitor. FIG. 6 (c) are bioluminescent images showing viral gene expression from tumors implanted into the peritoneal cavity for TK or TK-HMGB mut expression in mice fed a control diet or a high-fat diet. FIG. 6 (d) is a graph quantifying viral gene expression from tumors implanted into the peritoneal cavity for TK or TK-HMGB1mut expression at day 3 post treatment in mice fed a control diet or a high-fat diet (HFD).

FIG. 7 shows the effects of PBS, TK, or TK-HMGB1mut alone or in combination with the chemotherapeutic agent paclitaxel (Taxol®) on tumor cell survival rate and tumor growth. FIG. 7 (a) is a graph showing the survival rate of tumor cells after exposure to paclitaxel after being fed media taken from UCI-101 cells treated with PBS, TK, or TK-HMGB1mut. FIG. 7 (b) shows relative tumor size as a function of time in mice treated with the indicated combinations of paclitaxel, TK, and TK-HMGB1mut.

FIG. 8 (a) contains bioluminescent images representing viral gene expression from tumors in mice treated with a vaccinia strain (WR) or strains also expressing MMP8 or PH2O. FIG. 8 (b) shows quantification of bioluminescent imaging data (n=5) for treatment with vaccinia strain only (WR TK-only), vaccinia strain and MMP8 expression (WR TK-mmp8), or vaccinia strain and PH2O expression (WR TK-ph20). Expression of PH20 resulted in increased viral spread.

DETAILED DESCRIPTION

Figure 8:
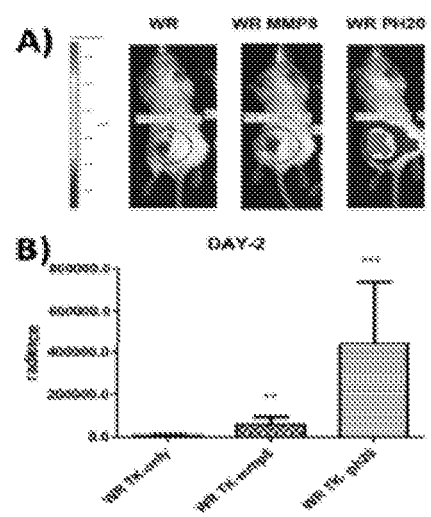
FIG. 8 shows the effect of a vaccinia strain alone or in combination with matrix metalloproteinase-8 (MMP8) expression or expression of the hyaluronidase PH2O.

While preferred embodiments of this disclosure have been shown and described herein, it will be obvious to those skilled in the art that such embodiments are provided by way of example only. Numerous variations, changes, and substitutions will now occur to those skilled in the art without departing from this disclosure. It should be understood that various alternatives to the embodiments of this disclosure described herein may be employed in practicing the disclosure. It is intended that the following claims define the scope of the disclosure and that methods and structures within the scope of these claims and their equivalents be covered thereby.

Certain Definitions

The terminology used herein is for the purpose of describing particular cases only and is not intended to be limiting. As used herein, the singular forms "a", "an" and "the" can include the plural forms as well, unless the context clearly indicates otherwise. Furthermore, to the extent that the terms "contains," "containing," "including", "includes," "having," "has", "with", or variants thereof are used in either the detailed description and/or the claims, such terms are intended to be inclusive in a manner similar to the term "comprising."

The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value, such as +10% of the value modified by the term "about".

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker). In some embodiments, patients, subjects, or individuals can be under the supervision of a health care worker.

The terms "heterologous nucleic acid sequence," or "exogenous nucleic acid sequence," as used herein, in relation to a specific virus can refer to a nucleic acid sequence that originates from a source other than the specified virus.

The term "mutation," as used herein, can refer to a deletion, an insertion of a heterologous nucleic acid, an inversion or a substitution, including an open reading frame ablating mutations as commonly understood in the art.

The term "gene," as used herein, can refer to a segment of nucleic acid that encodes an individual protein or RNA (also referred to as a "coding sequence" or "coding region"), optionally together with associated regulatory regions such as promoters, operators, terminators and the like, which may be located upstream or downstream of the coding sequence.

The terms "mutant virus" and "modified virus," as used interchangeably herein, can refer to a virus comprising one or more mutations in its genome, including but not limited to deletions, insertions of heterologous nucleic acids, inversions, substitutions or combinations thereof.

The term "naturally-occurring," as used herein with reference to a virus, can indicate that the virus can be found in nature, i.e., it can be isolated from a source in nature and has not been intentionally modified.

The terms "inhibiting," "reducing" or "prevention," or any variation of these terms, referred to herein, can include any measurable decrease or complete inhibition to achieve a desired result.

A "promoter," as used herein, can be a control sequence that is a region of a nucleic acid sequence at which initiation and rate of transcription are controlled. In certain embodiments, a promoter may contain genetic elements at which regulatory proteins and molecules may bind such as RNA polymerase and other transcription factors. The terms "operatively positioned," "operatively linked," "under control" and "under transcriptional control" can mean that a promoter is in a correct functional location and/or orientation in relation to a nucleic acid sequence to control transcriptional initiation and/or expression of that sequence. In certain embodiments, a promoter may or may not be used in conjunction with an "enhancer," which refers to a cis-acting regulatory sequence involved in the transcriptional activation of a nucleic acid sequence.

The term "homology," as used herein, may be to calculations of "homology" or "percent homology" between two or more nucleotide or amino acid sequences that can be determined by aligning the sequences for optimal comparison purposes (e.g., gaps can be introduced in the sequence of a first sequence). The nucleotides at corresponding positions may then be compared, and the percent identity between the two sequences may be a function of the number of identical positions shared by the sequences (i.e., % homology=# of identical positions/total # of positions×100). For example, a position in the first sequence may be occupied by the same nucleotide as the corresponding position in the second sequence, then the molecules are identical at that position. The percent homology between the two sequences may be a function of the number of identical positions shared by the sequences, taking into account the number of gaps, and the length of each gap, which need to be introduced for optimal alignment of the two sequences. In some embodiments, the length of a sequence aligned for comparison purposes may be at least about: 30%, 40%, 50%, 60%, 65%, 70%, 75%, 80%, 85%, 90%, 91%, 92%, 93%, 94%, 95%, 96%, 97%, 98%, or 95%, of the length of the reference sequence. A BLAST® search may determine homology between two sequences. The homology can be between the entire lengths of two sequences or between fractions of the entire lengths of two sequences. The two sequences can be genes, nucleotides sequences, protein sequences, peptide sequences, amino acid sequences, or fragments thereof. The actual comparison of the two sequences can be accomplished by well-known methods, for example, using a mathematical algorithm. A non-limiting example of such a mathematical algorithm may be described in Karlin, S. and Altschul, S., Proc. Natl. Acad. Sci. USA, 90-5873-5877 (1993). Such an algorithm may be incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In another embodiment, the percent identity between two amino acid sequences can be accomplished using, for example, the GAP program in the GCG software package (Accelrys, Cambridge, UK).

The term "subject" can refer to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" can be meant to include alleviating or abrogating a disorder, disease, or condition; or one or more of the symptoms associated with the disorder, disease, or condition; or alleviating or eradicating the cause(s) of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The term "therapeutically effective amount" can refer to the amount of a compound that, when administered, can be sufficient to prevent development of, or alleviate to some extent, one or more of the symptoms of the disorder, disease, or condition being treated. The term "therapeutically effective amount" can also refer to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" can refer to a pharmaceutically-acceptable material, composition, or vehicle, such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds.; Gower Publishing Company: 2007; *Pharmaceutical Preformulation and Formulation,* Gibson Ed., CRC Press LLC: Boca Raton, Fla., 2004).

The term "pharmaceutical composition" can refer to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

An "anti-cancer agent," as used herein, can refer to an agent or therapy that is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Non-limiting examples of anti-cancer agents can include biological agents (biotherapy), chemotherapy agents, and radiotherapy agents.

The term "oncolytic," as used herein, can refer to killing of cancer or tumor cells by an agent, such as an oncolytic vaccinia virus, e.g., through the direct lysis of said cells, by stimulating immune response towards said cells, apoptosis, expression of toxic proteins, autophagy and shut-down of protein synthesis, induction of anti-tumoral immunity, or any combinations thereof. The direct lysis of the cancer or tumor cells infected by the agent, such as an oncolytic vaccinia virus, can be a result of replication of the virus within said cells. In certain examples, the term "oncolytic," refers to killing of cancer or tumor cells without lysis of said cells.

Modified Viruses

In some embodiments are provided modified viruses, e.g., oncolytic vaccinia viruses that can contain an exogenous nucleic acid sequence that can code for a variant HMGB1 protein. Any other oncolytic virus can also be modified by inserting any of the exogenous nucleic acid sequences disclosed herein, to express a variant HMGB1, alone or in combination with additional exogenous nucleic acid sequences, further deletions of viral genes, e.g., virulence genes, or any combinations thereof. Examples of viruses included, but are not limited to, Herpes Simplex Virus (HSV), Adenovirus, Polio virus, VSV, Coxsackievirus, reovirus, lentivirus, adeno-associated virus (AAV), Measles virus, Maraba virus, Newcastle disease (NDV), Seneca valley virus, Reovirus, Mengovirus, and Myxomavir.

Viruses described herein comprise one or more exogenous nucleic acid sequences, alternatively referred to as transgenes, which can generate mRNAs coding for a variant HMGB1 protein (also referred to herein an HMGB1mut). Structurally, the HMGB1 protein is approximately 25 kDa with a highly and can comprise a structure composed of multiple domains, such as a box A domain, a box B domain, a C-terminal acidic tail, and a domain formed by the region between box B and the C-terminal acidic tail. Within the box A, the HMGB1 protein can comprise a first nuclear localization signal (NLS1) and within the domain formed by the region between box B and the C-terminal acidic tail, the HMGB1 protein can comprise a second nuclear localization signal (NLS2). FIG. 1(a) shows an exemplary structural arrangement for the HMGB1 protein. In certain embodiments of this disclosure is described, a virus, e.g., an oncolytic vaccinia virus, that can comprise an exogenous nucleic acid sequence that can code for a variant HMGB1, wherein said variant HMGB1 comprises a mutation in at least one of NLS1 and NLS2. The exogenous nucleic acid can comprise a further mutation in at least one of the domains described above as box A, box B, or the domain formed by the region between box B and the C-terminal acidic tail, or any combinations thereof. In some examples, one or more mutations in box A can be associated with a cytoplasmic relocation of the variant HMGB1. In some cases, the exogenous nucleic acid may not comprise the C-terminal acidic tail domain.

The cytoplasmic relocation can be attributed to one or more mutations in the NLS1 within box A, or one or more mutations in the NLS2 located in the domain formed by the region between the box B and the C-terminal acidic tail, or one or more mutations in both the NLS1 within box A and the NLS2 located in the domain formed by the region between the box B and the C-terminal acidic tail. A variant HMGB1 that relocates to the cytoplasm can be advantageous in inducing a cytotoxic immune response in tumor cells that have been infected with an oncolytic vaccinia virus that can comprise an exogenous nucleic acid sequence that can code for the variant HMGB1, as well as cells that are in the vicinity of the infected tumor cell but may not be directly infected by the vaccinia virus. Thus, the oncolytic vaccinia virus of this disclosure, comprising an exogenous nucleic acid that codes for a variant HMGB1 can be more efficacious as an inducer of cytotoxic immune response in a tumor microenvironment, generates enhanced cytotoxic immune response in uninfected cells by a bystander effect, compared to an otherwise identical vaccinia virus that does not comprise the exogenous nucleic acid coding for a variant HMGB1.

In some examples, the mutations present in a variant HMGB1 as described herein, e.g., one or more mutations in at least one of the following domains: box A box B, the domain formed by the region between box B and the acidic C-terminal tail; NLS1 within box A, NLS2 within the domain formed by the region between box B and the acidic C-terminal tail, or any combinations thereof, can be associated with an enhanced synergistic effect, when the virus, e.g., an oncolytic vaccinia virus comprising the exogenous nucleic acid that codes for the variant HMGB1 is administered in combination with a chemotherapy; said synergistic effect is not seen upon administration of an otherwise identical vaccinia virus that lacks the exogenous nucleic acid sequence coding for the variant HMGB1 that can comprise a mutation in at least one of the following domains: box A, box B, the domain formed by the region between box B and the acidic C-terminal tail; NLS1 within box A, NLS2 within the domain formed by the region between box B and the acidic C-terminal tail, or any combinations thereof. The synergistic effect of a combination with chemotherapy can be mediated by an immune effect and can be, in some cases, attributed to enhanced binding of the variant HMGB1 to at least one of TLR4 and RAGE.

In some examples, the mutations present in a variant HMGB1 as described herein, e.g., one or more mutations in at least one of the following domains: box A box B, the domain formed by the region between box B and the acidic C-terminal tail; NLS1 within box A, NLS2 within the domain formed by the region between box B and the acidic C-terminal tail, or any combinations thereof, can be associated with increased tumor selective replication of a virus, e.g., an oncolytic vaccinia virus, that can comprise the exogenous nucleic acid that can code for the variant HMGB1; said increase in tumor selective replication is not seen upon administration of an otherwise identical vaccinia virus that lacks the exogenous nucleic acid sequence coding for the variant HMGB1 that can comprise a mutation in at least one of the following domains: box A, box B, the domain formed by the region between box B and the acidic C-terminal tail; NLS1 within box A, NLS2 within the domain formed by the region between box B and the acidic C-terminal tail, or any combinations thereof. The increased tumor specific viral replication, in some examples, can be mediated by the effect of the variant HMGB1 on autophagy, and in some cases, attributed to certain cysteine residues within the variant HMGB1 protein.

In some examples, the mutations present in a variant HMGB1 as described herein, e.g., one or more mutations in at least one of the following domains: box A box B, the domain formed by the region between box B and the acidic C-terminal tail; NLS1 within box A, NLS2 within the domain formed by the region between box B and the acidic C-terminal tail, or any combinations thereof, can be associated with reduction in tumor growth by administering a, e.g., an oncolytic vaccinia virus, that can comprise the exogenous nucleic acid that can code for the variant HMGB, which lowers tumor interstitial fluid pressure (TIFP); said reduction in tumor growth by lowering of TIFP is not seen upon administration of an otherwise identical vaccinia virus that lacks the exogenous nucleic acid sequence coding for the variant HMGB1 that can comprise a mutation in at least one of the following domains: box A, box B, the domain formed by the region between box B and the acidic C-terminal tail, NLS1 within box A, NLS2 within the domain formed by the region between box B and the acidic C-terminal tail, or any combinations thereof.

The variant HMGB1, in some embodiments, can comprise an amino acid sequence that is less than about or equal to 80%, less than about or equal to 81%, less than about or equal to 82%, less than about or equal to 83%, less than about or equal to 84%, less than about or equal to 85%, less than about or equal to 86%, less than about or equal to 87%, less than about or equal to 88%, less than about or equal to 89%, less than about or equal to 90%, less than about or equal to 91%, less than about or equal to 92%, less than about or equal to 93%, less than about or equal to 94%, less than about or equal to 95%, less than about or equal to 96%, less than about or equal to 97%, less than about or equal to 98%, or less than about or equal to 99%, homologous to SEQ ID NO: 16, which corresponds to human wild type HMGB1 (also referred to herein as HMGB1wt).

Within the amino acid sequence set forth as SEQ ID NO: 16, various domains of HMGB1wt can be delineated as follows: box A can comprises residues 1-85; box B can comprise residues 88-162, C-terminal acidic tail can comprise residues 186-215; the domain formed between box B and the C-terminal acidic tail can comprise residues 162-185; NLS1 can comprise residues 28-54; and NLS2 can comprise residues 179-185. Some examples of the virus can comprise an exogenous nucleic acid sequence that can code for a variant HMGB1, which variant HMGB1 can be less than about or equal to 95% homologous to SEQ ID NO: 16, and can comprises at least one of residues 1-85, 89-108, and 150-183, wherein said at least one of residues 1-85, 89-108, and 150-183 can comprise at least one mutation compared to the amino acid sequence of SEQ ID NO: 16. For example, the virus, e.g., an oncolytic vaccinia virus, can comprise an exogenous nucleic acid sequence that can comprise residues 1-85 of SEQ ID NO: 16, wherein one or more serine residue within the stretch can be mutated, for example, to alanine. Furthermore, in some examples, the virus, e.g., an oncolytic vaccinia virus, can comprise an exogenous nucleic acid sequence that can comprise residues 89-108 of SEQ ID NO: 16, wherein one or more phenyl alanine residue within the stretch can be mutated, for example, to glutamic acid. In yet other examples, the virus, e.g., an oncolytic vaccinia virus, can comprise an exogenous nucleic acid sequence that can comprise residues 150-183 of SEQ ID NO: 16, wherein a serine residue within the stretch can be mutated, for example, to alanine. In certain instances, the virus, e.g., an oncolytic vaccinia virus, can comprise an exogenous nucleic acid sequence that can comprise mutations at one or more of positions 35, 42, 89, 181, 189, and 202 of SEQ ID NO: 16. In other instances, the virus, e.g., an oncolytic vaccinia virus, can comprise an exogenous nucleic acid sequence that can comprise mutations at all of positions 35, 42, 89, 181, 189, and 202 of SEQ ID NO: 16.

One embodiment provides a virus, e.g., an oncolytic vaccinia virus, that can comprise an exogenous nucleic acid sequence that can code for a variant HMGB1 that is less than about or equal to 95% homologous to SEQ ID NO: 16 and can comprises at least one of residues 23, 45, 23-45, 89-108, and 150-183 of SEQ ID NO: 16. In case of such viruses, the amino acid at positions 23 and 45 are both cysteines. Regarding the stretches covered by residues 89-108 and 150-183, the exogenous nucleic acid coding for variant HMGB1, as described herein, can comprise at least one mutation in those stretches compared to the amino acid SEQ ID NO: 16. For example, the virus, e.g., an oncolytic vaccinia virus, can comprise an exogenous nucleic acid sequence that can comprise residues 89-108 of SEQ ID NO: 16, wherein one or more phenyl alanine residue within the stretch can be mutated, for example, to glutamic acid. In yet other examples, the virus, e.g., an oncolytic vaccinia virus, can comprise an exogenous nucleic acid sequence that can comprise residues 150-183 of SEQ ID NO: 16, wherein a serine residue within the stretch can be mutated, for example, to alanine. In certain instances, the virus, e.g., an oncolytic vaccinia virus, can comprise an exogenous nucleic acid sequence that can comprise mutations at one or more of positions 35, 42, 89, 181, 189, and 202 of SEQ ID NO: 16. In other instances, the virus, e.g., an oncolytic vaccinia virus can comprise an exogenous nucleic acid sequence that can comprise mutations at all of positions 35, 42, 89, 181, 189, and 202 of SEQ ID NO: 16. In some instances, the exogenous nucleic acid comprises residues 23-54 of SEQ ID NO: 16, wherein amino acids at positions 23 and 45 can be cysteines and one or more of the serine residue in that stretch can be mutated to, e.g., to alanine.

A further embodiment provides a virus, e.g., an oncolytic vaccinia virus, that can comprise an exogenous nucleic acid sequence that can code for a variant HMGB1 that can be at least about 85%, at least about 90%, at least about 95%, at least about 96%, at least about 97%, at least about 98%, at least about 99%, or 100% homologous to SEQ ID NO: 15, or a fragment thereof. The virus, as described above, can comprise at least one of residues 21-74, 109-128, and 170-203 of SEQ ID NO: 15. In some cases, the virus can comprise at least one of residues 21-105, 109-128, and 170-203 of SEQ ID NO: 15. The stretch covered by residues 109-128 and 170-183 can play a role in binding of the HMGB1 variant to TLR4 and RAGE, respectively. Binding of the variant HMGB1 to at least one of TLR4 and RAGE can be correlated with an immune effect which can lead to, when the virus, e.g., an oncolytic vaccinia virus, comprising the exogenous nucleic acid that codes for the variant HMGB1 is administered in combination with chemotherapy. The amino acids in positions 43 and 65 of SEQ ID NO: 15 can be cysteines. In certain examples, the variant HMGB1, in its mature form, may not comprise residues 1-20 of SEQ ID NO: 15. A "fragment" of a nucleic acid or an amino acid described herein can refer to a portion comprising about 1%, about 2%, about 3%, about 4%, about 5%, about 10%, about 20%, about 30%, about 40%, about 50%, about 60%, about 70%, about 80%, about 90% of the entire length of the nucleic acid of amino acid sequence of which it is a fragment.

A further embodiment provides a virus, e.g., an oncolytic vaccinia virus, that can comprise an exogenous nucleic acid sequence that can code for a variant HMGB1 that can be at least about 85%, at least about 90%, at least about 95%, at least about 96%, at least about 97%, at least about 98%, at least about 99%, or 100% homologous to SEQ ID NO: 17, or a fragment thereof. The virus, as described above, can comprise at least one of residues 21-74, 109-128, and 170-203 of SEQ ID NO: 15. In some cases, the virus can comprise at least one of residues 21-105, 109-128, and 170-203 of SEQ ID NO: 17. The stretch covered by residues 109-128 and 170-183 can play a role in binding of the HMGB1 variant to TLR4 and RAGE, respectively. Binding of the variant HMGB1 to at least one of TLR4 and RAGE can be correlated with an immune effect which can mediate an enhanced synergistic effect, when the virus, e.g., an oncolytic vaccinia virus, comprising the exogenous nucleic acid that codes for the variant HMGB1 is administered in combination with chemotherapy. The amino acids in positions 43 and 65 of SEQ ID NO: 17 can be cysteines. The amino acids in positions 43 and 65 of SEQ ID NO: 15 can be cysteines. In certain examples, the variant HMGB1, in its mature form, may not comprise residues 1-20 of SEQ ID NO: 17.

A further embodiment provides a virus, e.g., an oncolytic vaccinia virus, that can comprise an exogenous nucleic acid sequence that can code for a variant HMGB1 that can be at least about 85%, at least about 90%, at least about 95%, at least about 96%, at least about 97%, at least about 98%, at least about 99%, or 100% homologous to SEQ ID NO: 4, or a fragment thereof. The virus, as described above, can comprise at least one of residues 21-74, 109-128, and 170-203 of SEQ ID NO: 4. In some cases, the virus can comprise at least one of residues 21-105, 109-128, and 170-203 of SEQ ID NO: 4. The stretch covered by residues 109-128 and 170-183 can play a role in binding of the HMGB1 variant to TLR4 and RAGE, respectively. Binding of the variant HMGB1 to at least one of TLR4 and RAGE can be correlated with an immune effect which can mediate an enhanced synergistic effect, when the virus, e.g., an oncolytic vaccinia virus, comprising the exogenous nucleic acid that codes for the variant HMGB1 is administered in combination with chemotherapy. The amino acids in positions 43 and 65 of SEQ ID NO: 4 can be cysteines. The amino acids in positions 43 and 65 of SEQ ID NO: 4 can be cysteines. In certain examples, the variant HMGB1, in its mature form, may not comprise residues 1-20 of SEQ ID NO: 4.

A further embodiment provides a virus, e.g., an oncolytic vaccinia virus, that can comprise an exogenous nucleic acid sequence that can code for a variant HMGB1 that can be at least about 85%, at least about 90%, at least about 95%, at least about 96%, at least about 97%, at least about 98%, at least about 99%, or 100% homologous to any one of SEQ ID NOs: 5, 6, 22-23, or a fragment thereof. In some cases, the coding sequence for a variant HMGB1 can be fused, upstream, to a coding sequence for an IgE leader sequence. The resulting protein can comprise an IgE leader sequence followed by a variant HMGB1 sequence, as exemplified in SEQ ID NOs: 24 and 25.

Within the amino acid sequences set forth as SEQ ID NOs: 4, 15, and 17, various domains of HMGB1 can be delineated as follows: box A can comprises residues 21-105; box B can comprise residues 108-182, C-terminal acidic tail can comprise residues 206-235; the domain formed between box B and the C-terminal acidic tail can comprise residues 183-205; NLS1 can comprise residues 47-74; and NLS2 can comprise residues 199-205.

A further embodiment provides a virus, e.g., an oncolytic vaccinia virus, that can comprise an exogenous nucleic acid sequence that can code for a variant HMGB1 that can be at least about 85%, at least about 90%, at least about 95%, at least about 96%, at least about 97%, at least about 98%, at least about 99%, or 100% homologous to any one of SEQ ID NOs: 24-25, or a fragment thereof.

Within the amino acid sequences set forth as SEQ ID NOs: 22 and 23, various domains of HMGB1 can be delineated as follows: box A can comprises residues 1-85; box B can comprise residues 88-162, C-terminal acidic tail can comprise residues 186-215; the domain formed between box B and the C-terminal acidic tail can comprise residues 162-185; NLS1 can comprise residues 28-54; and NLS2 can comprise residues 179-185.

Within the amino acid sequences set forth as SEQ ID NOs: 24 and 25, various domains of HMGB1 can be delineated as follows: box A can comprises residues 19-103; box B can comprise residues 106-180, C-terminal acidic tail can comprise residues 204-233; the domain formed between box B and the C-terminal acidic tail can comprise residues 181-203; NLS1 can comprise residues 45-72; and NLS2 can comprise residues 197-203.

Presence of cysteine residues in positions 23 and 45 of an exogenous nucleic acid which is less than about or equal to 95% homologous to SEQ ID NO: 16, and positions 43 and 65 of an exogenous nucleic acid which is at least about 80% homologous any one of SEQ ID NOs: 4, 15, and 17, can, in some cases, be correlated to increase in tumor specific replication of viruses, e.g., oncolytic vaccinia viruses, which may contain one of said exogenous nucleic acid sequences that codes for a variant HMGB1. The increased tumor specific replication of oncolytic vaccinia viruses expressing the variant HMGB1 proteins can be mediated by the effect of the HMGB1 protein on autophagy, and the cysteine residues identified above may play a role in the same.

The exogenous nucleic acid coding for the variant HMGB1 can comprise a nucleotide sequence that is at least about 85%, at least about 90%, at least about 95%, at least about 96%, at least about 97%, at least about 98%, at least about 99%, or 100% homologous to any one of SEQ ID NO: 13, SEQ ID NO: 13, 2, 3, 7, 9, 14, and 19. In some examples, the exogenous nucleic acid comprises a nucleic acid sequence that is at least about 85%, at least about 90%, at least about 95%, at least about 96%, at least about 97%, at least about 98%, at least about 99%, or 100% homologous to any one of SEQ ID NO: 13 and wherein said nucleic acid codes for a variant HMGB1 that is at least about 85%, at least about 90%, at least about 95%, at least about 96%, at least about 97%, at least about 98%, at least about 99%, or 100% homologous to any one of SEQ ID NO: 15.

One embodiment describes a virus, e.g., an oncolytic virus that can further express a hyaluronidase in addition to the variant HMGB1. The hyaluronidase can be coded by a further exogenous nucleic acid sequence within the oncolytic vaccinia virus; said further exogenous nucleic acid sequence can have a nucleotide sequence set forth in SEQ ID NO: 11, and the hyaluronidase expressed from the oncolytic vaccinia virus can have an amino acid sequence as set forth in SEQ ID NO: 12. Any hyaluronidase can be expressed from the virus, including, but not limited to, HYAL1, HYAL2, and HYAL3, HYAL4, PH-20, SPAM1 (sperm adhesion molecule 1), and HYALP1.

One embodiment describes a virus, e.g., an oncolytic virus that can further express a protein that stabilizes the virus in circulation, in addition to the variant HMGB1. Examples of such protein can include IgE, an Fc domain protein. In some cases, the IgE can be coded by a further exogenous nucleic acid sequence within the oncolytic vaccinia virus; said IgE expressed from the oncolytic vaccinia virus can have an amino acid sequence as set forth in SEQ ID NO: 18.

The exogenous nucleic acid sequence coding for a hyaluronidase, and the sequence coding for IgE can be operably linked to the exogenous nucleic acid sequence coding for a variant HMGB1 as described herein. In some examples, the IgE is fused upstream to both variant HMGB1 coding gene and the hyaluronidase coding gene. Other arrangements of the IgE, hyaluronidase, and variant HMGB1 coding gene are also contemplated.

Additional modifications to the virus, e.g., to an oncolytic vaccinia virus can include, but are not limited to, deletions of virulence genes, such as B8R (codes for IFN-g binding protein), B18R (codes for type I IFN binding protein), B13R (codes for serpin SPI-1 which has anti-apoptotic activity, B22R (codes for serpin SPI-2 which has anti-apoptotic activity), B15R (codes for IL-1b binding protein), VGF (codes for Vaccinia Growth Factor), E3L (codes for dsRNA binding), K3L (codes for PKR binding).

The modified virus can further express a chemotherapy sensitizer, such as hyaluronic acid; an apoptosis enhancer, such as TRAIL or caspase. In some cases, the modified virus can further express an efflux pump blockers, such as a multi drug transporter inhibitor.

In certain embodiments, exogenous nucleic acid sequences for insertion into the viral genome, e.g., in the thymidine kinase locus or in place of other deletions within the genome of an oncolytic vaccinia virus, can be codon optimized. Further, the variant HMGB1 expressed by such exogenous nucleic acid sequences, as well as the hyaluronidase and stabilizing protein sequences can have variants such that the resulting protein maintains their respective functions as described herein. In certain embodiments, such changes are referred to as conservative substitutions. As used herein, the terms "conservative substitutions" and "conservative modifications" refer to amino acid modifications that do not significantly affect or alter the binding characteristics of the presently disclosed variant HMGB1 proteins comprising the amino acid sequence. Such conservative modifications include amino acid substitutions, additions and deletions. Modifications can be introduced into the HMGB1 proteins of this disclosure by standard techniques known in the art, such as site-directed mutagenesis and PCR-mediated mutagenesis. Amino acids can be classified into groups according to their physicochemical properties such as charge and polarity.

Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within the variant HMGB1 protein can be replaced with other amino acid residues from the same group and the altered variant HMGB1 protein can be tested for retained function using the functional assays described herein. In certain embodiments, no more than one, no more than two, no more than three, no more than four, no more than five residues within a specified sequence are altered. Exemplary conservative amino acid substitutions are shown in Table I.

TABLE I

| Original Residue | Exemplary Conservative Amino Acid Substitutions |
| --- | --- |
| Ala (A) | Val; Leu; Ile |
| Arg (R) | Lys; Gin; Asn |
| Asn (N) | Gln; His; Asp, Lys; Arg |
| Asp (D) | Giu; Asn |
| Cys (C) | Ser; Ala |
| Gin (Q) | Asn; Glu |
| Glu (E) | Asp; Gin |
| Gly (G) | Ala |
| His (H) | Asn; Gin; Lys; Arg |
| Ile (I) | Leu; Val; Met; Ala; Phe |
| Leu (L) | Ile; Val; Met; Ala; Phe |
| Lys (K) | Arg; Gin; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Cancer Targets

In an embodiment of this disclosure, a method of treatment for a hyperproliferative disease, such as a cancer or a tumor, by the delivery of a modified virus, such as an oncolytic vaccinia virus as described herein, is contemplated. Cancers that can be treated by a modified virus, e.g., an oncolytic vaccinia virus that can comprise an exogenous nucleic acid coding for a variant HMGB1 protein, as described herein can include, but are not limited to, melanoma, hepatocellular carcinoma, breast cancer, lung cancer, peritoneal cancer, prostate cancer, bladder cancer, ovarian cancer, leukemia, lymphoma, renal carcinoma, pancreatic cancer, epithelial carcinoma, gastric cancer, colon carcinoma, duodenal cancer, pancreatic adenocarcinoma, mesotheliorna, glioblastoma multiforrne, astrocytoma, multiple myeloma, prostate carcinoma, hepatocellular carcinoma, cholangiosarcoma, pancreatic adenocarcinoma, head and neck squamous cell carcinoma, colorectal cancer, intestinal-type gastric adenocarcinoma, cervical squamous-cell carcinoma, osteosarcoma, epithelial ovarian carcinoma, acute lymphoblastic lymphoma, myeloproliferative neoplasms, and sarcoma.

Cancer cells that can be treated by the methods of this disclosure include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant;

synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In various examples, the variant HMGB for use in a modified virus of this disclosure, such as an oncolytic vaccinia virus, that can be used to treat cancer targets disclosed herein, can be a variant HMGB1 comprising the sequence set forth as SEQ ID NO: 4, 15, 17, 22, 23, 24, or 25.

This disclosure also contemplates methods for inhibiting or preventing local invasiveness or metastasis, or both, of any type of primary cancer. For example, the primary cancer can be melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder. In certain embodiments, the primary cancer can be lung cancer. For example, the lung cancer can be non-small cell lung carcinoma. Moreover, this disclosure can be used to prevent cancer or to treat pre-cancers or premalignant cells, including metaplasias, dysplasias, and hyperplasias. It can also be used to inhibit undesirable but benign cells, such as squamous metaplasia, dysplasia, benign prostate hyperplasia cells, hyperplastic lesions, and the like. In some embodiments, the progression to cancer or to a more severe form of cancer can be halted, disrupted, or delayed by methods of this disclosure involving variant HMGB1 proteins that can be encoded by a modified virus, such as an oncolytic vaccinia virus, as discussed herein. In various examples, the variant HMGB1 for use in a modified virus of this disclosure, such as an oncolytic vaccinia virus, that can be used for inhibiting or preventing local invasiveness or metastasis, or both, of any type of primary cancer, can be a variant HMGB1 comprising the sequence set forth as SEQ ID NO: 4, 15, 17, 22, 23, 24, or 25.

In some cases, the modified virus, such as an oncolytic vaccinia virus comprising an exogenous nucleic acid sequence that codes for a variant HMGB1 can be administered for treatment of a peritoneal cancer. Peritoneal cancer can refer to cancer of the peritoneum. The peritoneum can be defined as tissue that lines the abdominal wall and covers abdominal organs. Primary peritoneal cancer can refer to cancer that originated in the peritoneum and did not spread to the peritoneum from another part of the body.

Furthermore, the modified virus, such as an oncolytic vaccinia virus comprising an exogenous nucleic acid sequence that codes for a variant HMGB1 can be administered for treatment of tumors with high bioavailability of free fatty acids in the tumor microenvironment. In some instances, free fatty acids released by adipocytes in tumors in obese patients can feed and enhance the replication of the modified virus within the tumor. The advantage can also be realized in non-obese patients, especially patients who have peritoneal cancer. For example, several peritoneal cancers can be targets for therapy using the modified viruses of this disclosure as these tend to grow in omentum wall and can be fed by adipocytes, and as mentioned above free fatty acids released by adipocytes in tumors can feed and enhance the replication of the modified virus within the tumor. The modified virus, such as an oncolytic vaccinia virus comprising an exogenous nucleic acid sequence that codes for a variant HMGB1, can form an increased titer of extracellular enveloped virus (EEV) in tumors with high bioavailability of free fatty acids.

Exemplary cancer patient populations that can benefit from the modified virus of this disclosure, such as an oncolytic vaccinia virus that expresses a variant HMGB1, optionally with a hyaluronidase, e.g., PH-20, include, but are not limited to, patients who are obese, patients who are on ketogenic diet or short term fasting, patients who have peritoneal cancer, patients who have primary peritoneal cancer, patients who have peritoneal cancer affecting the uterus, bladder, and rectum. Further, patients that have previously failed immunotherapy can be identified as a target population for treatment using the modified viruses described herein, according to the methods disclosed herein. Such patients may not benefit from a further round of immunotherapy and can move on to a treatment with a modified virus, such as an oncolytic vaccinia virus of this disclosure, alone or in combination with chemotherapy. Thus, therapy using the modified viruses of this disclosure can be a key alternative in case of patients who have failed immunotherapy.

The term "obese" or "obesity," can refer to a condition wherein an individual has a BMI equal to or greater than 30 kg/m2. According to a World Health Organization (WHO) definition, obesity can be categorized as follows: the term "class I obesity" can be a condition wherein the BMI is equal to or greater than 30 kg/m2 but lower than 35 kg/m2; the term "class II obesity" can be a condition wherein the BMI is equal to or greater than 35 kg/m2 but lower than 40 kg/m2; the term "class III obesity" can be a condition wherein the BMI is equal to or greater than 40 kg/m2. A BMI of 18.5 to 24.9 kg/m2 can be classified as normal, and a BMI of 25.0 to 29.9 kg/m2 can be classified as overweight. The term "body mass index" or "BMI" can be defined as weight in kilograms divided by height in meters squared, such that BMI has units of kg/m2. BMI can be a measure for defining obesity.

Methods of Treatment and Assaying the Efficacy and Pharmacokinetics

This disclosure provides methods for treating a subject by administration of one or more modified viruses, as disclosed herein. An "individual" or "subject," as used interchangeably herein, refers to a human or a non-human subject. Non-limiting examples of non-human subjects include non-human primates, dogs, cats, mice, rats, guinea pigs, rabbits, pigs, fowl, horses, cows, goats, sheep, cetaceans, etc. In some embodiments, the subject is human.

Provided is a method of producing a toxic effect in a cancer cell comprising administering, to the cancer cell, a therapeutically effective amount of a modified virus, such as an oncolytic vaccinia virus, as described above, or a pharmaceutical composition containing the same. This disclosure further provides a method of inhibiting at least one of growth and proliferation of a second cancer cell comprising administering, to a first cancer cell, a modified virus as described above such that the first cancer cell is infected with said virus. Thus, in some embodiments of the methods disclosed here, it is contemplated that not every cancer or tumor cell is infected upon administering a therapeutically effective amount of an oncolytic vaccinia virus, as described herein, or a pharmaceutical composition containing the same, and growth of non-infected cells can be inhibited without direct infection.

In some examples, to induce oncolysis, kill cells, inhibit growth, inhibit metastases, decrease tumor size and otherwise reverse or reduce the malignant phenotype of tumor cells, using the methods and compositions of the present disclosure, a cancer cell or a tumor can be contacted with a therapeutically effective dose of an exemplary oncolytic vaccinia virus as described herein or a pharmaceutical composition containing the same. In certain embodiments, an effective amount of a modified virus of the present disclosure, such as an oncolytic vaccinia virus as described herein or a pharmaceutical composition thereof, can include an amount sufficient to induce oncolysis, the disruption or lysis of a cancer cell or the inhibition or reduction in the growth or size of a cancer cell. Reducing the growth of a cancer cell may be manifested, for example, by cell death or a slower replication rate or reduced growth rate of a tumor comprising the cell or a prolonged survival of a subject containing the cancer cell.

Provided, in some embodiments, is a method of treating a subject having a cancer or a tumor comprising administering, to the subject, an effective amount of a modified virus, as described above. An effective amount in such method can include an amount that reduces growth rate or spread of the cancer or that prolongs survival in the subject. This disclosure provides a method of reducing the growth of a tumor, which method can comprise administering, to the tumor, an effective amount of a modified virus as described above. In certain embodiments, an effective amount of a modified virus, or a pharmaceutical composition thereof, can include an amount sufficient to induce the slowing, inhibition or reduction in the growth or size of a tumor and can include the eradication of the tumor. Reducing the growth of a tumor may be manifested, for example, by reduced growth rate or a prolonged survival of a subject containing the tumor.

This disclosure also provides a method of determining the infectivity or antitumor activity, or amount of tumor specific viral replication of an oncolytic vaccinia virus as described herein, which method can comprise; (i) administering to a subject a therapeutically effective amount of an oncolytic vaccinia virus or a pharmaceutical composition according to the present disclosure, which further expresses a luciferase reporter gene, alone or in combination with a further therapy; (ii) collecting a first biological sample from the subject immediately after administering the virus and determining the level of the luciferase reporter in the first biological sample (iii) collecting a second biological sample from the subject following the administration in step (ii) and (iii) detecting the level of the luciferase reporter in the second biological sample, wherein the oncolytic vaccinia virus is determined to be infective, demonstrate antitumor activity, exhibit tumor specific viral replication if the level of luciferase is higher in step (iii) than in step (ii). The second biological sample is collected about 30 mins, about 1 hour, about 2 hours, about 3 hours, about 4 hours, about 5 hours, about 6 hours, about 7 hours, about 8 hours, about 9 hours, about 10 hours, about 12 hours, about 15 hours, about 24 hours, about 36 hours, about 48 hours, about 72 hours, about 4 days, about 5 days, about 6 days, about 7 days, about 8 days, about 9 days, about 10 days, about 11 days, about 12 days, about 13 days, about 14 days, about 15 days, about 1 month, to about 2 months after the administration in step (i). In some embodiments, the method of mentioned above can further comprise, detecting in steps (i) and (iii), the level of one or more assaying cytokine levels, e.g., IL-2, IL-7, IL-8, IL-10, IFN-γ, GM-CSF, TNF-α, IL-6, IL-4, IL-5, and IL-13, in plasma samples collected from a subject after administering to said subject a therapeutically effective amount of a modified virus of the present disclosure, such as an oncolytic vaccinia virus as described herein or a pharmaceutical composition comprising the same. In some embodiments of this disclosure, the increase in luciferase bioluminescence between steps (ii) and (iv) mentioned above is higher for a modified virus of this disclosure, e.g., an oncolytic vaccinia virus containing the exogenous nucleic acid that codes for a variant HMGB1 as described herein, compared to that in an otherwise identical virus that does not contain the exogenous nucleic acid sequence coding for the variant HMGB1. Other exemplary techniques for detecting and monitoring viral load after administration of the modified viruses include real-time quantitative PCR.

Further provided is a method of monitoring the pharmacokinetics following administration of a therapeutically effective amount of modified viruses according to the present disclosure, such as oncolytic vaccinia virus or a pharmaceutical composition containing the vaccinia virus, as described herein. An exemplary method for monitoring the pharmacokinetics can comprise the following steps: (i) administering to the subject a therapeutically effective amount of an oncolytic vaccinia virus or a pharmaceutical composition comprising the same, alone or in combination with a further therapy; (ii) collecting biological samples from the subject at one or more time points selected from about 15 minutes, about 30 minutes, about 45 mins, about 60 mins, about 75 mins, about 90 mins, about 120 mins, about 180 mins, and about 240 mins, about 5 hours, about 6 hours, about 7 hours, about 8 hours, about 9 hours, about 10 hours, about 12 hours, about 15 hours, about 24 hours, about 36 hours, about 48 hours, about 72 hours, about 4 days, about 5 days, about 6 days, about 7 days, about 8 days, about 9 days, about 10 days, about 11 days, about 12 days, about 13 days, about 14 days, about 15 days, about 1 month, to about 2 months after the administration in step (i) and (iii) detecting the quantity of the viral genome (or a reporter gene inserted within the viral genome, such as luciferase) in the biological samples collected at the above mentioned time points. In some instances, viral genome copies/mL can be highest in the sample collected at the 15 mins time point and further the sample collected at the 240 mins time point may not contain a detectable quantity of the viral genome. Therefore, in some instances, a viral peak can be observed at about 15 mins following administration and majority of the viruses can be cleared from the subject's system after about 240 mins (or 4 hours). In some instances, a first viral peak can be observed after about 15 mins following administration and a second viral peak can be observed in the biological samples collected in the subsequent time points, e.g., at about 30 mins, about 45 mins, about 60 mins, or about 90 mins. The biological sample can be, in exemplar embodiments, blood, and the quantity of viral genome/mL can be determined by quantitative PCR or other appropriate techniques. In some examples, a first viral peak can be observed after about 15 mins following administration and a second viral peak can be observed after about 30 mins, about 1 hour, about 2 hours, about 3 hours, about 4 hours, about 5 hours, about 6 hours, about 7 hours, about 8 hours, about 9 hours, about 10 hours, about 12 hours, about 15 hours, about 24 hours, about 36 hours, about 48 hours, about 72 hours, about 4 days, about 5 days, about 6 days, about 7 days, about 8 days, about 9 days, about 10 days, about 11 days, about 12 days, about 13 days, about 14 days, about 15 days, about 1 month, to about 2 months following administration of a modified virus of the present disclosure, such as an oncolytic vaccinia virus as described herein.

In some instances, tumor-selective replication of a modified virus, such as an oncolytic vaccinia virus can be measured through use of a reporter gene, such as a luciferase gene. In some embodiments, the luciferase gene can be inserted into the genome of a virus, and a tumor cell can be infected with the virus. Bioluminescence in infected tumor cells can be measured to monitor tumor-selective replication. Some examples show an increase in luciferase reporter bioluminescence in a modified virus of this disclosure, such as an oncolytic vaccinia virus comprising an exogenous nucleic acid sequence that codes for a variant HMGB1, compared to that in an otherwise identical oncolytic vaccinia virus that does not contain the exogenous nucleic acid sequence that codes for the variant HMGB1.

The hyaluronidase PH-20 can function in extracellular matrix degradation, which can improve viral spread. Viral spread can also be measured through use of a reporter gene, such as a luciferase gene. The luciferase gene can be inserted into the genome of a virus, and a tumor cell can be infected with the virus. Bioluminescence in infected tumor cells can be measured to evaluate viral spread. Some examples show an increase in luciferase reporter bioluminescence in a modified virus of this disclosure, such as an oncolytic vaccinia virus comprising an exogenous nucleic acid sequence that codes for a variant HMGB1 in combination with the PH-20, compared to that in an otherwise identical oncolytic vaccinia virus that does not contain the exogenous nucleic acid sequence that codes for the variant HMGB1 in combination with the PH-20. Thus, in certain instances, the modified virus of this disclosure, such as an as an oncolytic vaccinia virus comprising an exogenous nucleic acid sequence that codes for a variant HMGB1 alone, or in combination with PH-20, demonstrate increased tumor specific viral replication and improved viral spread compared to viruses which do not have the exogenous genes as mentioned above.

Delivery of Modified Viruses

In some embodiments, amount of a modified virus of this disclosure, such as an oncolytic vaccinia virus, administered to a subject can be between about $10^3$ and $10^{12}$ infectious viral particles or plaque forming units (PFU), or between about $10^5$ and $10^{10}$ PFU, or between about $10^5$ and $10^8$ PFU, or between about $10^8$ and $10^{10}$ PFU. In some embodiments, the amount of a modified virus of this disclosure, such as an oncolytic vaccinia virus administered to a subject can be between about $10^3$ and $10^{12}$ viral particles or plaque forming units (PFU), or between about $10^5$ and $10^{10}$ PFU, or between about $10^5$ and $10^8$ PFU, or between about $10^8$ and $10^{10}$ PFU. In some embodiments, a modified virus of this disclosure, such as an oncolytic vaccinia virus, can be administered at a dose that can comprise about $10^3$ PFU/dose to about $10^4$ PFU/dose, about $10^4$ PFU/dose to about $10^5$ PFU/dose, about $10^5$ PFU/dose to about $10^6$ PFU/dose, about $10^7$ PFU/dose to about $10^8$ PFU/dose, about $10^9$ PFU/dose to about $10^{10}$ PFU/dose, about $10^{11}$ PFU/dose to about $10^{11}$ PFU/dose, about $10^{11}$ PFU/dose to about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. In some embodiments, a modified virus of this disclosure, such as an oncolytic vaccinia virus, can be administered at a dose that can comprise about $2\times10^3$ PFU/dose, $3\times10^3$ PFU/dose, $4\times10^3$ PFU/dose, $5\times10^3$ PFU/dose, $6\times10^3$ PFU/dose, $7\times10^3$ PFU/dose, $8\times10^3$ PFU/dose, $9\times10^3$ PFU/dose, about $10^4$ PFU/dose, about $2\times10^4$ PFU/dose, about $3\times10^4$ PFU/dose, about $4\times10^4$ PFU/dose, about $5\times10^4$ PFU/dose, about $6\times10^4$ PFU/dose, about $7\times10^4$ PFU/dose, about $8\times10^4$ PFU/dose, about $9\times10^4$ PFU/dose, about $10^5$ PFU/dose, $2\times10^5$ PFU/dose, $3\times10^5$ PFU/dose, $4\times10^5$ PFU/dose, $5\times10^5$ PFU/dose, $6\times10^5$ PFU/dose, $7\times10^5$ PFU/dose, $8\times10^5$ PFU/dose, $9\times10^5$ PFU/dose, about $10^6$ PFU/dose, about $2\times10^6$ PFU/dose, about $3\times10^6$ PFU/dose, about $4\times10^6$ PFU/dose, about $5\times10^6$ PFU/dose, about $6\times10^6$ PFU/dose, about $7\times10^6$ PFU/dose, about $8\times10^6$ PFU/dose, about $9\times10^6$ PFU/dose, about $10^7$ PFU/dose, about $2\times10^7$ PFU/dose, about $3\times10^7$ PFU/dose, about $4\times10^7$ PFU/dose, about $5\times10^7$ PFU/dose, about $6\times10^7$ PFU/dose, about $7\times10^7$ PFU/dose, about $8\times10^7$ PFU/dose, about $9\times10^7$ PFU/dose, about 108 PFU/dose, about $2\times10^8$ PFU/dose, about $3\times10^8$ PFU/dose, about $4\times10^8$ PFU/dose, about $5\times10^8$ PFU/dose, about $6\times10^8$ PFU/dose, about $7\times10^8$ PFU/dose, about $8\times10^8$ PFU/dose, about $9\times10^9$ PFU/dose, about $10^9$ PFU/dose, about $2\times10^9$ PFU/dose, about $3\times10^9$ PFU/dose, about $4\times10^9$ PFU/dose, about $5\times10^9$ PFU/dose, about $6\times10^9$ PFU/dose, about $7\times10^9$ PFU/dose, about $8\times10^9$ PFU/dose, about $9\times10^9$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about $7\times10^{10}$ PFU/dose, about $8\times10^{10}$ PFU/dose, about $9\times10^{10}$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about $7\times10^{10}$ PFU/dose, about $8\times10^{10}$ PFU/dose, about $9\times10^{10}$ PFU/dose, about $10^{11}$ PFU/dose, about $2\times10^{11}$ PFU/dose, about $3\times10^{11}$ PFU/dose, about $4\times10^{11}$ PFU/dose, about $5\times10^{11}$ PFU/dose, about $6\times10^{11}$ PFU/dose, about $7\times10^{11}$ PFU/dose, about $8\times10^{11}$ PFU/dose, about $9\times10^{11}$ PFU/dose, or about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose.

In some embodiments, a modified virus of this disclosure, such as an oncolytic vaccinia virus, can be administered at a dose that can comprise $5\times10^9$ PFU/dose. In some embodiments, a modified virus of this disclosure, such as an oncolytic vaccinia virus, can be administered at a dose that can comprise up to $5\times10^9$ PFU/dose.

In some embodiments, a modified virus of this disclosure, such as an oncolytic vaccinia virus, can be administered at a dose that can comprise about $10^3$ viral particles/dose to about 104 viral particles/dose, about 104 viral particles/dose to about $10^5$ viral particles/dose, about $10^5$ viral particles/dose to about $10^6$ viral particles/dose, about $10^7$ viral particles/dose to about $10^8$ viral particles/dose, about $10^9$ viral particles/dose to about $10^{10}$ viral particles/dose, about $10^{10}$ viral particles/dose to about $10^{11}$ viral particles/dose, about $10^{11}$ viral particles/dose to about $10^{12}$ viral particles/dose, about $10^{12}$ viral particles/dose to about $10^{13}$ viral particles/ dose, about $10^{13}$ viral particles/dose to about $10^{14}$ viral particles/dose, or about $10^{14}$ viral particles/dose to about $10^{15}$ viral particles/dose.

In some embodiments, a modified virus of this disclosure can be administered at a dose that can comprise about $10^3$ PFU/kg to about $10^4$ PFU/kg, about $10^4$ PFU/kg to about $10^5$ PFU/kg, about 10' PFU/kg to about $10^6$ PFU/kg, about $10^7$ PFU/kg to about $10^8$ PFU/kg, about $10^9$ PFU/kg to about $10^{10}$ PFU/kg, about $10^{10}$ PFU/kg to about $10^{11}$ PFU/kg, about $10^{11}$ PFU/kg to about $10^{12}$ PFU/kg, about $10^{12}$ PFU/kg to about $10^{13}$ PFU/kg, about $10^{13}$ PFU/kg to about $10^{14}$ PFU/kg, or about $10^{14}$ PFU/kg to about $10^{15}$ PFU/kg. In some embodiments, a modified virus of this disclosure, such as an oncolytic vaccinia virus, can be administered at a dose that can comprise about $2\times10^3$ PFU/kg, $3\times10^3$ PFU/kg, $4\times10^3$ PFU/kg, $5\times10^3$ PFU/kg, $6\times10^3$ PFU/kg, $7\times10^3$ PFU/kg, $8\times10^3$ PFU/kg, $9\times10^3$ PFU/kg, about 104 PFU/kg, about $2\times10^4$ PFU/kg, about $3\times10^4$ PFU/kg, about $4\times10^4$ PFU/kg, about $5\times10^4$ PFU/kg, about $6\times10^4$ PFU/kg, about $7\times10^4$ PFU/kg, about $8\times10^4$ PFU/kg, about $9\times10^4$ PFU/kg, about $10^5$ PFU/kg, $2\times10^5$ PFU/kg, $3\times10^5$ PFU/kg, $4\times10^5$ PFU/kg, $5\times10^5$ PFU/kg, $6\times10^5$ PFU/kg, $7\times10^5$ PFU/kg, $8\times10^5$ PFU/kg, $9\times10^5$ PFU/kg, about $10^6$ PFU/kg, about $2\times10^6$ PFU/kg, about $3\times10^6$ PFU/kg, about $4\times10^6$ PFU/kg, about $5\times10^6$ PFU/kg, about $6\times10^6$ PFU/kg, about $7\times10^6$ PFU/kg, about $8\times10^6$ PFU/kg, about $9\times10^6$ PFU/kg, about $10^7$ PFU/kg, about $2\times10^7$ PFU/kg, about $3\times10^7$ PFU/kg, about $4\times10^7$ PFU/kg, about $5\times10^7$ PFU/kg, about $6\times10^7$ PFU/kg, about $7\times10^7$ PFU/kg, about $8\times10^7$ PFU/kg, about $9\times10^7$ PFU/kg, about $10^8$ PFU/kg, about $2\times10^8$ PFU/kg, about $3\times10^8$ PFU/kg, about $4\times10^8$ PFU/kg, about $5\times10^8$ PFU/kg, about $6\times10^8$ PFU/kg, about $7\times10^8$ PFU/kg, about $8\times10^8$ PFU/kg, about $9\times10^8$ PFU/kg, about $10^9$ PFU/kg, about $2\times10^9$ PFU/kg, about $3\times10^9$ PFU/kg, about $4\times10^9$ PFU/kg, about $5\times10^9$ PFU/kg, about $6\times10^9$ PFU/kg, about $7\times10^9$ PFU/kg, about $8\times10^9$ PFU/kg, about $9\times10^9$ PFU/kg, about 100 PFU/kg, about $2\times10^{10}$ PFU/kg, about $3\times10^{10}$ PFU/kg, about $4\times10^{10}$ PFU/kg, about $5\times10^{10}$ PFU/kg, about $6\times10^{10}$ PFU/kg, about $7\times10^{10}$ PFU/kg, about $8\times10^{10}$ PFU/kg, about $9\times10^{10}$ PFU/kg, about $10^{10}$ PFU/kg, about $2\times10^{10}$ PFU/kg, about $3\times10^{10}$ PFU/kg, about $4\times10^{10}$ PFU/kg, about $5\times10^{10}$ PFU/kg, about $6\times10^{10}$ PFU/kg, about $7\times10^{10}$ PFU/kg, about $8\times10^{10}$ PFU/kg, about $9\times10^{10}$ PFU/kg, about $10^{11}$ PFU/kg, about $2\times10^{11}$ PFU/kg, about $3\times10^{11}$ PFU/kg, about $4\times10^{11}$ PFU/kg, about $5\times10^{11}$ PFU/kg, about $6\times10^{11}$ PFU/kg, about $7\times10^{11}$ PFU/kg, about $8\times10^{11}$ PFU/kg, about $9\times10^{11}$ PFU/kg, or about $10^{12}$ PFU/kg, about $10^{12}$ PFU/kg to about $10^{13}$ PFU/kg, about $10^{13}$ PFU/kg to about $10^{14}$ PFU/kg, or about $10^{14}$ PFU/kg to about $10^{15}$ PFU/kg. In some embodiments, a modified virus of this disclosure, such as an oncolytic vaccinia virus, can be administered at a dose that can comprise $5\times10^9$ PFU/kg. In some embodiments, a modified virus of this disclosure, such as an oncolytic vaccinia virus, can be administered at a dose that can comprise up to $5\times10^9$ PFU/kg.

In some embodiments, a modified virus of this disclosure can be administered at a dose that can comprise about $10^3$ viral particles/kg to about $10^4$ viral particles/kg, about $10^4$ viral particles/kg to about $10^5$ viral particles/kg, about $10^5$ viral particles/kg to about $10^6$ viral particles/kg, about $10^7$ viral particles/kg to about $10^8$ viral particles/kg, about $10^9$ viral particles/kg to about $10^{10}$ viral particles/kg, about $10^{10}$ viral particles/kg to about $10^{11}$ viral particles/kg, about $10^{11}$ viral particles/kg to about $10^{12}$ viral particles/kg, about $10^{12}$ viral particles/kg to about $10^{13}$ viral particles/kg, about $10^{13}$ viral particles/kg to about $10^{14}$ viral particles/kg, or about $10^{14}$ viral particles/kg to about $10^{15}$ viral particles/kg.

A liquid dosage form of an oncolytic vaccinia virus as described herein can comprise, in certain embodiments, a viral dose of about $10^3$ PFU/mL to about $10^4$ PFU/mL, about $10^4$ PFU/mL to about $10^5$ PFU/mL, about $10^6$ PFU/mL to about $10^6$ PFU/mL, about $10^7$ PFU/mL to about $10^8$ PFU/mL, about $10^9$ PFU/mL to about $10^{10}$ PFU/mL, about $10^{10}$ PFU/mL to about $10^{11}$ PFU/mL, about $10^{11}$ PFU/mL to about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In some embodiments, a modified virus of this disclosure, such as an oncolytic vaccinia virus, can be administered at a dose that can comprise about $2\times10^3$ PFU/mL, $3\times10^3$ PFU/mL, $4\times10^3$ PFU/mL, $5\times10^3$ PFU/mL, $6\times10^3$ PFU/mL, $7\times10^3$ PFU/mL, $8\times10^3$ PFU/mL, $9\times10^3$ PFU/mL, about $10^4$ PFU/mL, about $2\times10^4$ PFU/mL, about $3\times10^4$ PFU/mL, about $4\times10^4$ PFU/mL, about $5\times10^4$ PFU/mL, about $6\times10^4$ PFU/mL, about $7\times10^4$ PFU/mL, about $8\times10^4$ PFU/mL, about $9\times10^4$ PFU/mL, about $10^5$ PFU/mL, $2\times10^5$ PFU/mL, $3\times10^5$ PFU/mL, $4\times10^5$ PFU/mL, $5\times10^5$ PFU/mL, $6\times10^5$ PFU/mL, $7\times10^5$ PFU/mL, $8\times10^5$ PFU/mL, $9\times10^5$ PFU/mL, about $10^6$ PFU/mL, about $2\times10^6$ PFU/mL, about $3\times10^6$ PFU/mL, about $4\times10^6$ PFU/mL, about $5\times10^6$ PFU/mL, about $6\times10^6$ PFU/mL, about $7\times10^6$ PFU/mL, about $8\times10^6$ PFU/mL, about $9\times10^6$ PFU/mL, about $10^7$ PFU/mL, about $2\times10^7$ PFU/mL, about $3\times10^7$ PFU/mL, about $4\times10^7$ PFU/mL, about $5\times10^7$ PFU/mL, about $6\times10^7$ PFU/mL, about $7\times10^7$ PFU/mL, about $8\times10^7$ PFU/mL, about $9\times10^7$ PFU/mL, about $10^8$ PFU/mL, about $2\times10^8$ PFU/mL, about $3\times10^8$ PFU/mL, about $4\times10^8$ PFU/mL, about $5\times10^8$ PFU/mL, about $6\times10^8$ PFU/mL, about $7\times10^8$ PFU/mL, about $8\times10^8$ PFU/mL, about $9\times10^8$ PFU/mL, about $10^9$ PFU/mL, about $2\times10^9$ PFU/mL, about $3\times10^9$ PFU/mL, about $4\times10^9$ PFU/mL, about $5\times10^9$ PFU/mL, about $6\times10^9$ PFU/mL, about $7\times10^9$ PFU/mL, about $8\times10^9$ PFU/mL, about $9\times10^9$ PFU/mL, about $10^8$ PFU/mL, about $2\times10^1$ PFU/mL, about $3\times10^{10}$ PFU/mL, about $4\times10^{10}$ PFU/mL, about $5\times10^{10}$ PFU/mL, about $6\times10^{10}$ PFU/mL, about $7\times10^{10}$ PFU/mL, about $8\times10^{10}$ PFU/mL, about $9\times10^{10}$ PFU/mL, about $10^{10}$ PFU/mL, about $2\times10^{10}$ PFU/mL, about $3\times10^{10}$ PFU/mL, about $4\times10^{10}$ PFU/mL, about $5\times10^{10}$ PFU/mL, about $6\times10^{10}$ PFU/mL, about $7\times10^{10}$ PFU/mL, about $8\times10^{10}$ PFU/mL, about $9\times10^{10}$ PFU/mL, about $10^{11}$ PFU/mL, about $2\times10^{11}$ PFU/mL, about $3\times10^{11}$ PFU/mL, about $4\times10^{11}$ PFU/mL, about $5\times10^{11}$ PFU/mL, about $6\times10^{11}$ PFU/mL, about $7\times10^{11}$ PFU/mL, about $8\times10^{11}$ PFU/mL, about $9\times10^{11}$ PFU/mL, or about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In some embodiments, a modified virus of this disclosure, such as an oncolytic vaccinia virus, can be administered at a dose that can comprise $5\times10^9$ PFU/mL. In some embodiments, a modified virus of this disclosure, such as an oncolytic vaccinia virus, can be administered at a dose that can comprise up to $5\times10^9$ PFU/mL.

In some instances, where the modified virus is administered by an injection, the dosage can comprise about $10^3$ viral particles per injection, $10^4$ viral particles per injection, $10^5$ viral particles per injection, $10^6$ viral particles per injection, $10^7$ viral particles per injection, $10^8$ viral particles per injection, $10^9$ viral particles per injection, $10^{10}$ viral particles per injection, $10^{11}$ viral particles per injection, $10^{12}$ viral particles per injection, $2\times10^{12}$ viral particles per injection, $10^{13}$ viral particles per injection, $10^{14}$ viral particles per injection, or $10^{15}$ viral particles per injection. In further instances, where the modified virus is administered by an injection, the dosage can comprise about $10^3$ infectious viral particles per injection, $10^4$ infectious viral particles per injection, $10^5$ infectious viral particles per injection, $10^6$ infectious viral particles per injection, $10^7$ infectious viral particles per injection, $10^8$ infectious viral particles per injection, $10^9$ infectious viral particles per injection, $10^{10}$ infectious viral particles per injection, $10^{11}$ infectious viral particles per injection, $10^{12}$ infectious viral particles per injection, $2\times10^{12}$ infectious viral particles per injection, $10^{13}$ infectious viral particles per injection, $10^{14}$ infectious viral particles per injection, or $10^{15}$ infectious viral particles per injection. In additional embodiments, a modified virus of this disclosure can be administered at a dose that can be about $10^3$ Tissue Culture Inhibitor Dose 50% ($TCID_{50}$)/kg, 10 $TCID_{50}$/kg, 104 $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $3\times10^8$ $TCID_{50}$/kg, $4\times10^8$ $TCID_{50}$/kg, $5\times10^8$ $TCID_{50}$/kg, $3\times10^9$ $TCID_{50}$/kg, $4\times10^9$ $TCID_{50}$/kg, $5\times10^9$ $TCID_{50}$/kg, $3\times10^{10}$ $TCID_{50}$/kg, $4\times10^{10}$ $TCID_{50}$/kg, or $4\times10^{10}$ $TCID_{50}$/kg. Note that herein 10× is alternatively expressed as 1 eX. In certain embodiments, the modified virus can be administered in one or more doses. In certain embodiments, the virus can be administered in an amount sufficient to induce oncolysis in at least about 20% of cells in a tumor, in at least about 30% of cells in a tumor, in at least about 40% of cells in a tumor, in at least about 50% of cells in a tumor, in at least about 60% of cells in a tumor, in at least about 70% of cells in a tumor, in at least about 80% of cells in a tumor, or in at least about 90% of cells in a tumor. In certain embodiments, a single dose of virus can refer to the amount administered to a subject or a tumor over a 1, 2, 5, 10, 15, 20 or 24 hour period. In certain embodiments, the dose can be spread over time or by separate injection. In certain embodiments, multiple doses (e.g., 2, 3, 4, 5, 6 or more doses) of the vaccinia virus can be administered to the subject, for example, where a second treatment can occur within 1, 2, 3, 4, 5, 6, 7 days or weeks of a first treatment. In certain embodiments, multiple doses of the modified virus can be administered to the subject over a period of 1, 2, 3, 4, 5, 6, 7 or more days or weeks. In certain embodiments, the oncolytic vaccinia virus or the pharmaceutical composition as described herein can be administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the oncolytic vaccinia virus or the pharmaceutical composition as described herein can be, in certain instances, once daily, twice daily, once every week, once every three weeks, once every four weeks (or once a month), once every 8 weeks (or once every 2, months), once every 12 weeks (or once every 3 months), or once every 24 weeks (once every 6 months). In some embodiments of the methods disclosed herein, the oncolytic vaccinia virus or the pharmaceutical composition can be administered, independently, in an initial dose for a first period of time, an intermediate dose for a second period of time, and a high dose for a third period of time. In some embodiments, the initial dose is lower than the intermediate dose and the intermediate dose is lower than the high dose. In some embodiments, the first, second, and third periods of time are, independently, about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer.

In some examples, the subject can be put on a reduced carbohydrate diet, e.g., a ketogenic diet prior to, concurrent with, and following administration of the modified viruses, such as the oncolytic vaccina viruses or the pharmaceutical composition comprising the same, as described herein, according to any of the methods of treatment described herein. In certain embodiments, the subject is put on a diet that can comprise consuming less than 500 grams of carbohydrates per day, less than 450 grams of carbohydrates per day, less than 450 grams of carbohydrates per day, less than 400 grams of carbohydrates per day, less than 350 grams of carbohydrates per day, less than 300 grams of carbohydrates per day, less than 250 grams of carbohydrates per day, less than 200 grams of carbohydrates per day, less than 150 grams of carbohydrates per day, less than 100 grams of carbohydrates per day, less than 90 grams of carbohydrates per day, less than 80 grams of carbohydrates per day, less than 70 grams of carbohydrates per day, less than 60 grams of carbohydrates per day, less than 50 grams of carbohydrates per day, less than 40 grams of carbohydrates per day, less than 30 grams of carbohydrates per day, less than 20 grams of carbohydrates per day, less or than 10 grams of carbohydrates per day.

An exemplary method for the delivery of a modified virus of the present disclosure, such as an oncolytic vaccinia virus as described herein or a pharmaceutical composition comprising the same, to cancer or tumor cells can be via intratumoral injection. However, alternate methods of administration can also be used, e.g, intravenous, via infusion, parenteral, intravenous, intradermal, intramuscular, transdermal, rectal, intraurethral, intravaginal, intranasal, intrathecal, or intraperitoneal. The routes of administration can vary with the location and nature of the tumor. In certain embodiments, the route of administration can be intradental, transdermal, parenteral, intravenous, intramuscular, intranasal, subcutaneous, regional (e.g., in the proximity of a tumor, particularly with the vasculature or adjacent vasculature of a tumor), percutaneous, intrathecal, intratracheal, intraperitoneal, intraarterial, intravesical, intratumoral, inhalation, perfusion, by lavage or orally. An injectable dose of the oncolytic virus can be administered as a bolus injection or as a slow infusion. In certain embodiments, the modified virus can be administered to the patient from a source implanted in the patient. In certain embodiments, administration of the modified virus can occur by continuous infusion over a selected period of time. In some instances, an oncolytic vaccinia virus as described herein, or a pharmaceutical composition containing the same can be administered at a therapeutically effective dose by infusion over a period of about 15 mins, about 30 mins, about 45 mins, about 50 mins, about 55 mins, about 60 minutes, about 75 mins, about 90 mins, about 100 mins, or about 120 mins or longer. The oncolytic vaccina virus or the pharmaceutical composition of the present disclosure can be administered as a liquid dosage, wherein the total volume of administration is about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350 mL to about 400 mL, about 400 mL to about 450 mL, about 450 mL to 500 mL, about 500 mL to 750 mL, or about 750 mL to 1000 mL.

Pharmaceutical Compositions

Pharmaceutical compositions containing a modified virus, such as an oncolytic vaccinia virus, as described herein, can be prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof. In some embodiments, a pharmaceutical composition as described herein can comprise a solubilizer, such as sterile water, Tris-buffer. In some embodiments, a pharmaceutical composition as described herein can comprise an excipient. An excipient can be an excipient described in the Handbook of Pharmaceutical Excipients, American Pharmaceutical Association (1986). Non-limiting examples of suitable excipients can include a buffering agent, a preservative, a stabilizer, a binder, a compaction agent, a lubricant, a chelator, a dispersion enhancer, a disintegration agent, a flavoring agent, a sweetener, a coloring agent.

In some embodiments an excipient can be a buffering agent. Non-limiting examples of suitable buffering agents can include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof can be used in a pharmaceutical formulation.

In some embodiments an excipient can comprise a preservative. Non-limiting examples of suitable preservatives can include antioxidants, such as alpha-tocopherol and ascorbate, and antimicrobials, such as parabens, chlorobutanol, and phenol. Antioxidants can further include but not limited to EDTA, citric acid, ascorbic acid, butylated hydroxytoluene (BHT), butylated hydroxy anisole (BHA), sodium sulfite, p-amino benzoic acid, glutathione, propyl gallate, cysteine, methionine, ethanol and N-acetyl cysteine. In some instances a preservatives can include validamycin A, TL-3, sodium ortho vanadate, sodium fluoride, N-a-tosyl-Phe-chloromethylketone, N-a-tosyl-Lys-chloromethyl ketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In some embodiments a pharmaceutical composition as described herein can comprise a binder as an excipient. Non-limiting examples of suitable binders can include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof. The binders that can be used in a pharmaceutical formulation can be selected from starches such as potato starch, corn starch, wheat starch; sugars such as sucrose, glucose, dextrose, lactose, maltodextrin; natural and synthetic gums; gelatine; cellulose derivatives such as microcrystalline cellulose, hydroxypropyl cellulose, hydroxyethyl cellulose, hydroxypropyl methyl cellulose, carboxymethyl cellulose, methyl cellulose, ethyl cellulose; polyvinylpyrrolidone (povidone); polyethylene glycol (PEG); waxes; calcium carbonate; calcium phosphate; alcohols such as sorbitol, xylitol, mannitol and water or a combination thereof.

In some embodiments a pharmaceutical composition as described herein can comprise a lubricant as an excipient. Non-limiting examples of suitable lubricants can include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricants that can be used in a pharmaceutical formulation can be selected from metallic stearates (such as magnesium stearate, calcium stearate, aluminium stearate), fatty acid esters (such as sodium stearyl fumarate), fatty acids (such as stearic acid), fatty alcohols, glyceryl behenate, mineral oil, paraffins, hydrogenated vegetable oils, leucine, polyethylene glycols (PEG), metallic lauryl sulphates (such as sodium lauryl sulphate, magnesium lauryl sulphate), sodium chloride, sodium benzoate, sodium acetate and talc or a combination thereof.

In some embodiments a pharmaceutical formulation can comprise a dispersion enhancer as an excipient. Non-limiting examples of suitable dispersants can include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments a pharmaceutical composition as described herein can comprise a disintegrant as an excipient. In some embodiments a disintegrant can be a non-effervescent disintegrant. Non-limiting examples of suitable non-effervescent disintegrants can include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In some embodiments a disintegrant can be an effervescent disintegrant. Non-limiting examples of suitable effervescent disintegrants can include sodium bicarbonate in combination with citric acid, and sodium bicarbonate in combination with tartaric acid.

In some embodiments an excipient can comprise a flavoring agent. Flavoring agents incorporated into an outer layer can be chosen from synthetic flavor oils and flavoring aromatics; natural oils; extracts from plants, leaves, flowers, and fruits; and combinations thereof. In some embodiments a flavoring agent can be selected from the group consisting of cinnamon oils; oil of wintergreen; peppermint oils; clover oil; hay oil; anise oil; *eucalyptus*; vanilla; citrus oil such as lemon oil, orange oil, grape and grapefruit oil; and fruit essences including apple, peach, pear, strawberry, raspberry, cherry, plum, pineapple, and apricot.

In some embodiments an excipient can comprise a sweetener. Non-limiting examples of suitable sweeteners can include glucose (corn syrup), dextrose, invert sugar, fructose, and mixtures thereof (when not used as a carrier); saccharin and its various salts such as a sodium salt; dipeptide sweeteners such as aspartame; dihydrochalcone compounds, glycyrrhizin; *Stevia rebaudiana* (Stevioside); chloro derivatives of sucrose such as sucralose; and sugar alcohols such as sorbitol, mannitol, sylitol, and the like.

In some instances, a pharmaceutical composition as described herein can comprise a coloring agent. Non-limiting examples of suitable color agents can include food, drug and cosmetic colors (FD&C), drug and cosmetic colors (D&C), and external drug and cosmetic colors (Ext. D&C). A coloring agents can be used as dyes or their corresponding lakes.

In some instances, a pharmaceutical composition as described herein can comprise a chelator. In some cases, a chelator can be a fungicidal chelator. Examples can include, but are not limited to: ethylenediamine-N,N,N',N'-tetraacetic acid (EDTA); a disodium, trisodium, tetrasodium, dipotassium, tripotassium, dilithium and diammonium salt of EDTA; a barium, calcium, cobalt, copper, dysprosium, europium, iron, indium, lanthanum, magnesium, manganese, nickel, samarium, strontium, or zinc chelate of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenedi amine-N,N'-dipropionic acid dihydrochloride; ethylenediamine-N,N'-bis(methylenephosphonic acid) hemihydrate; N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11]pentatriacontane hexahydrobromide; or triethylenetetramine-N,N,N',N'',N''',N'''-hexaacetic acid.

Also contemplated are combination products that include one or more modified viruses disclosed herein and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that a peptide can be combined with topical antifungal agents such as ciclopirox olamine, haloprogin, tolnaftate, undecylenate, topical nysatin, amorolfine, butenafine, naftifine, terbinafine, and other topical agents. In some instances, a pharmaceutical composition can comprise an additional agent. In some cases, an additional agent can be present in a therapeutically effective amount in a pharmaceutical composition.

Under ordinary conditions of storage and use, the pharmaceutical compositions as described herein can comprise a preservative to prevent the growth of microorganisms. In certain examples, the pharmaceutical compositions as described herein may not comprise a preservative. The pharmaceutical forms suitable for injectable use can include sterile aqueous solutions or dispersions and sterile powders for the extemporaneous preparation of sterile injectable solutions or dispersions. The pharmaceutical compositions can comprise a carrier which is a solvent or a dispersion medium containing, for example, water, ethanol, polyol (e.g., glycerol, propylene glycol, and liquid polyethylene glycol, and the like), and/or vegetable oils, or any combinations thereof. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For-parenteral administration in an aqueous solution, for example, the liquid dosage form can be suitably buffered if necessary and the liquid diluent rendered isotonic with sufficient saline or glucose. The liquid dosage forms are especially suitable for intravenous, intramuscular, subcutaneous, intratumoral, and intraperitoneal administration. In this connection, sterile aqueous media that can be employed will be known to those of skill in the art in light of the present disclosure. For example, one dosage may be dissolved in 1 mL to 20 mL of isotonic NaCl solution and either added to 100 mL to 1000 mL of a fluid, e.g., sodium-bicarbonate buffered saline, or injected at the proposed site of infusion.

In certain embodiments, sterile injectable solutions can be prepared by incorporating a modified virus according to the present disclosure, such as oncolytic vaccinia viruses as described herein or a pharmaceutical composition containing the same, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, the pharmaceutical compositions can be administered in a manner compatible with the dosage formulation and in such amount as is therapeutically effective.

In certain embodiments, a pharmaceutical composition of this disclosure can comprise an effective amount of a modified virus, disclosed herein, combined with a pharmaceutically acceptable carrier. "Pharmaceutically acceptable," as used herein, includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically compatible carriers can include gels, bioadsorbable matrix materials, implantation elements containing the modified virus or any other suitable vehicle, delivery or dispensing means or material. Such carriers can be formulated by conventional methods and can be administered to the subject at an effective amount.

Methods of Production

The modified viruses of this disclosure can be produced by methods known to one of skill in the art. In certain embodiments, the modified virus can be propagated in suitable host cells, e.g., HeLa cells, 293 cells, or Vero cells, isolated from host cells and stored in conditions that promote stability and integrity of the virus, such that loss of infectivity over time is minimized. In certain exemplary methods, the modified viruses are propagated in host cells using cell stacks, roller bottles, or perfusion bioreactors. In some examples, downstream methods for purification of the modified viruses can comprise filtration (e.g., depth filtration, tangential flow filtration, or a combination thereof), ultracentrifugation, or chromatographic capture. The modified virus can be stored, e.g., by freezing or drying, such as by lyophilization. In certain embodiments, prior to administration, the stored modified virus can be reconstituted (if dried for storage) and diluted in a pharmaceutically acceptable carrier for administration.

Some embodiments provide that the modified virus as described herein, such as an oncolytic vaccinia virus comprising an exogenous nucleic acid coding for variant HMGB1 exhibit a higher titer in HeLa cells and 293 cells compared to an otherwise identical virus that does not contain the exogenous nucleic acid coding for the variant HMGB1. In certain instances, a higher titer in HeLa cells and 293 cells is seen in modified vaccinia viruses expressing a variant HMGB1 and a hyaluronidase, such as PH-20.

Combination Therapies

In certain embodiments, the methods of this disclosure comprise administering a modified virus as disclosed herein or a pharmaceutical composition containing the same, followed by, and preceded by or in combination with one or more further therapy. Examples of the further therapy can include, but are not limited to, chemotherapy, radiation, oncolytic viral therapy with an additional virus, treatment with immunomodulatory proteins, an anti-cancer agent, or any combinations thereof. The further therapy can be administered concurrently or sequentially with respect to administration of the modified virus, such as oncolytic vaccinia virus. In certain embodiments, the methods of this disclosure can comprise administering a modified virus as disclosed herein, followed by, preceded by, or in combination with one or more anti-cancer agents or cancer therapies. Anti-cancer agents can include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies can include chemotherapy, biological therapy, radiotherapy, immunotherapy, hormone therapy, anti-vascular therapy, cryotherapy, toxin therapy and/or surgery or combinations thereof. In certain embodiments, the methods of this disclosure can include administering a modified virus, disclosed herein, followed by, preceded by or in combination with an modified virus of this disclosure, such as an oncolytic vaccinia virus comprising an exogenous nucleic acid sequence that codes for a variant HMGB1 as described herein, alone or in combination with PH-20. Combination of the oncolytic vaccinia virus with chemotherapy achieves a synergistic effect which is not seen in modified viruses that do not contain the variant HMGB1 coding nucleic acid sequence. The synergistic effect of the above combination can be advantageously used to lower the dose of chemotherapy, such as Taxol®. Thus, the treatment method disclosed here, with the modified virus, can reduced toxicities associated with chemotherapy, e.g., patients who respond to chemotherapy but suffer side effects at therapeutic doses. The synergistic effect, can, in certain cases, results in a decrease in tumor growth compared to chemotherapy alone or oncolytic vaccinia virus alone. Exemplary decrease in tumor growth can be from about 2% to about 50%, such as about 5%, about 10%, about 20%, about 25%, about 35%, about 45% or about 50%.

In certain embodiments, treatment using a modified virus can be used alone or in combination with one or immunomodulatory agents. An immunomodulatory agent can include any compound, molecule or substance capable of suppressing antiviral immunity associated with a tumor or cancer. In certain-embodiments, the immunomodulatory agent can be capable of suppressing innate immunity or adaptive immunity to the modified virus. Non-limiting examples of immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2, IFN3 and 1FNy, and chemokines, such as MIP-1, MCP-1 and 11-8. In certain embodiments, the immunomodulatory agent includes immune checkpoint inhibitors such as, but not limited to, anti-CTLA4, anti-PD-1, anti-PDL1 and TLR agonists (e.g., Poly 1:C).

In certain examples, where the further therapy is radiation exemplary doses can be 5,000 Rads (50 Gy) to 100,000 Rads (1000 Gy), or 50,000 Rads (500 Gy), or other appropriate doses within the recited ranges. Alternatively, the radiation dose can be about 30 to 60 Gy, about 40 to about 50 Gy, about 40 to 48 Gy, or about 44 Gy, or other appropriate doses within the recited ranges, with the dose determined, example, by means of a dosimetry study as described above. "Gy" as used herein can refer to a unit for a specific absorbed dose of radiation equal to 100 Rads. Gy is the abbreviation for "Gray."

In certain examples, where the further therapy is chemotherapy, exemplary chemotherapeutic agents can include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids). Exemplary chemotherapeutic agents can include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), Ibrutinib, idelalisib, and brentuximab vedotin.

Exemplary alkylating agents can include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines can include, without limitation, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids can include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors can, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoac etamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1 S)-2-[(2R)-2-methyl-2-oxiranyl]-2-oxo-1-(phenylmethyl)ethyl]-L-serinamide (ONX-0912).

"In combination with," as used herein, means that the modified virus, such as an oncolytic vaccinia virus as described herein or a pharmaceutical composition comprising the same, and the further therapy, such as a further therapy comprising one or more agents are administered to a subject as part of a treatment regimen or plan. In certain embodiments, being used in combination does not require that the modified virus and the one or more agents are physically combined prior to administration or that they be administered over the same time frame. For example, and not by way of limitation, the modified virus and the one or more agents can be administered concurrently to the subject being treated, or can be administered at the same time or sequentially in any order or at different points in time.

The further therapy can be administered, in various embodiments, in a liquid dosage form, a solid dosage form, a suppository, an inhalable dosage form, an intranasal dosage form, in a liposomal formulation, a dosage form comprising nanoparticles, a dosage form comprising microparticles, a polymeric dosage form, or any combinations thereof. In certain embodiments, the further therapy is administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the further therapy can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In certain embodiments, a method of treating a subject having a cancer can include administering, to the subject, an effective amount of a modified virus, e.g., vaccinia virus, expressing one or more nucleic acids that encode variant HMGB1 protein comprising an amino acid sequence that is at least about 85%, about 90%, about 95%, about 96%, about 97%, about 98%, about 99% or 100% homologous to an amino acid sequence selected from the group consisting of SEQ ID NOs: 4, 15, 17, 19, 5, 6, 8, 10, and 22-25 and conservative substitutions thereof. For example, and not by way of limitation, a modified virus of this disclosure can comprise a nucleic acid that can comprise a nucleotide sequence that is at least about 85%, about 90%, about 95%, about 96%, about 97%, about 98%, about 99% or 100% homologous to a nucleic acid sequence selected from the group consisting of SEQ ID NOs: 8-10. In certain embodiments, the methods of this disclosure can further include administering to the subject an effective amount of one or more agents. For example, and not by way of limitation, the agent can be an anti-cancer agent, an immunomodulatory agent, or any combinations thereof, as described above.

Kits

In embodiments, this disclosure provides for a kit for administering a modified virus as described herein. In certain embodiments, a kit of this disclosure can include a modified virus or a pharmaceutical composition comprising a modified virus as described above. In certain embodiments, a kit of this disclosure can further include one or more components such as instructions for use, devices and additional reagents, and components, such as tubes, containers and syringes for performing the methods disclosed above. In certain embodiments, a kit of this disclosure can further include one or more agents, e.g., at least one of an anti-cancer agent, an immunomodulatory agent, or any combination thereof, that can be administered in combination with a modified virus.

In certain embodiments, a kit of this disclosure can comprise one or more containers containing a modified virus, disclosed herein. For example, and not by way of limitation, a kit of this disclosure can comprise one or more containers that contain a modified vaccinia virus expressing a variant HMGB1, with or without at least one of PH20 and IgE, or any combinations thereof. In certain embodiments, the variant HMGB1 can be conjugated to a cell penetrating peptide.

In certain embodiments, a kit of this disclosure can include an effective amount of a modified vaccinia virus comprising one or more nucleic acids that encode a variant HMGB1 that can comprise an amino acid sequence that can be at least about 85%, at least about 90%, at least about 95%, at least about 96%, at least about 97%, at least about 98%, at least about 99% or 100% homologous to an amino acid sequence selected from the group consisting of SEQ ID NOs: 4, 15, 17, and 22-25, and conservative substitutions thereof. In certain embodiments, a kit of this disclosure can include an effective amount of a modified vaccinia virus comprising one or more nucleic acids that encode a variant HMGB1 that can comprise an amino acid sequence that can be less than about or equal to 85%, less than about or equal to 90%, less than about or equal to 95%, less than about or equal to 96%, less than about or equal to 97%, or less than about or equal to 98%, or less than about or equal to 99% homologous to SEQ ID NO: 16, and conservative substitutions thereof.

In certain embodiments, a kit of this disclosure can include instructions for use, a device for administering the modified virus to a subject, or a device for administering an additional agent or compound to a subject. For example, and not by way of limitation, the instructions can include a description of the modified virus and, optionally, other components included in the kit, and methods for administration, including methods for determining the proper state of the subject, the proper dosage amount and the proper administration method for administering the modified virus. Instructions can also include guidance for monitoring the subject over duration of the treatment time.

In certain embodiments, a kit of this disclosure can include a device for administering the modified virus to a subject. Any of a variety of devices known in the art for administering medications and pharmaceutical compositions can be included in the kits provided herein. For example, and not by way of limitation, such devices include, a hypodermic needle, an intravenous needle, a catheter, a needle-less injection device, an inhaler and a liquid dispenser, such as an eyedropper. In certain embodiments, a modified virus to be delivered systemically, for example, by intravenous injection, an intratumoral injection, an intraperitoneal injection, can be included in a kit with a hypodermic needle and syringe.

Examples

The examples below further illustrate the described embodiments without limiting the scope of this disclosure.

Example 1: Design and Expression of an Exemplary Variant HMGB1

One example of a variant HMGB1 (also referred to herein as "HMGB1mut") that provided unexpected therapeutic advantage is shown in FIG. 1a. This diagram shows that the two nuclear localization signals (NLSs) in HMGB1 were mutated, and an IgE sequence was fused to the N-terminus of the transgene to stabilize the protein in the extracellular environment. This increased the variant HMGB1's immune-activating functions to allow greater bystander effect, with uptake in surrounding, uninfected cells leading to enhanced autophagy.

This transgene was inserted into the viral thymidine kinase locus under control of the viral p7.5 promoter (FIG. 1b). Loss of thymidine kinase function is a well-characterized approach to creating a tumor-selective VACV vector. In addition, luciferase was inserted into the same locus under control of the pSE/L promoter and used as a reporter gene to track viral gene expression in vitro and in vivo. Expression of HMGB1mut was confirmed by Western Blot (FIG. 1c) and ELISA (FIG. 1d) in the media from two mouse tumor cell lines (Renca and 4T1) after infection with different viruses.

Example 2: Viral Expression of the Exemplary Variant HMGB1 Enhances Therapeutic Effects in Cancer Cell Lines and Murine Tumor Models The aim of this study was to explore the effects of an exemplary modified oncolytic vaccinia virus according to this disclosure, where the thymidine kinase gene was deleted and an exogenous nucleic acid encoding a variant HMGB1 was added (referred to herein as TK-HMGB1mut), in cancer cell lines and murine models, in comparison with an oncolytic vaccinia virus that did not contain the nucleic acid expressing HMGB mut (referred to herein as TK-).

In initial in vivo experiments, a single intravenous dose of virus (TK- or TK-HMGB1mut) was used to treat immuno-competent mice with pre-established subcutaneous tumors (FIG. 2). It was seen that in the normally resistant Renca tumor model, HMGB1mut expression resulted in significantly enhanced therapeutic activity. In the more sensitive MC38 model, HMGB1mut expression provided an additional and significant therapeutic benefit; however, this was less dramatic.

The effects of HMGB1mut expression was examined across a range of mouse tumor and normal cell lines to better define the mechanisms driving the enhanced therapeutic activity. It was initially noted that phosphorylated IKKb levels were significantly increased with HMGB1mut expression (FIG. 3a). This would be expected to result in NF-kB activation, which in turn could sensitize cells to apoptosis and/or enhance release of a variety of cytokines. However, the expression levels of a variety of cytokines and chemokines involved in both innate and adaptive immunity were either unchanged or reduced after infection with virus expressing HMGB1mut (relative to infection with TK-virus) (FIG. 3b-e). Furthermore, after naïve BALB/c mice were inoculated with either TK- or TK-HMGB1mut, there was no significant change in the level of anti-viral CTL response induced; in fact, there was a trend towards a reduction in the CTL response with HMGB1mut expression, although this was not significant (FIG. 3f). Finally, when SCID mice bearing Renca tumors were treated with TK- or TK-HMGB1 mut, the HMGB1mut expression maintained a therapeutic advantage (FIG. 3g). Therefore, there is a non-immune component to the therapeutic advantage provided by the transgene.

HMGB1 typically is associated with cell survival. Thus, reduced viral replication or no increase in viral replication was expected when using the HMGB1mut. However, one unexpected finding when using the HMGB1mut was an increase in viral replication that was seen across multiple tumor cell lines in culture (FIG. 4a). This unexpected, increased replication was observed despite insignificant differences in cell killing (FIGS. 4b and 4d). HMGB1mut expression resulted in a small increase in cell killing, which combined with the increased activation of IKKb (FIG. 3a) would indicate that the enhanced replication is not due to a block in cellular apoptosis.

The increased viral replication was also seen in tumors in vivo with significantly increased viral luciferase gene expression detected in both Renca (FIG. 4c) and MC38 (FIG. 4e) tumors. The increase was more significant in the Renca tumor model that also showed the greater increase in therapeutic benefit (FIG. 2). It is notable that the increased replication (viral gene expression) seen in vivo was confined to the tumor (FIG. 4f), even in SCID mice where the enhanced replication in the tumor (FIG. 4g) is sustained continuously. This is notable as viral modifications that create tumor-targeting OV strains typically involve attenuating viral replication in normal tissues, rather than selectively enhancing replication in the tumor.

The effects of HMGB1mut expression on autophagy markers were examined. It was seen that expression of the transgene resulted in an increase in LC3 (FIG. 5a) and that inhibitors of maturation of autophagic vacuoles (the vacuolar H+ATPase inhibitor, Bafilomycin A1) and PI3K (LY294002; PI3K/AKT/mTOR pathway is known to modulate autophagy) both resulted in loss of the increased viral gene expression originally seen with HMGB1mut expression (FIG. 5b). This implies that HMGB1 effects on autophagy may drive the enhanced viral replication.

HCT 116 cells were transfected with siRNA targeting Atg5, a key mediator of the autophagy pathway. It was seen that loss of autophagic potential negatively affected viral replication (FIG. 6a). This finding contradicts a previous study that indicated autophagy did not affect vaccinia replication.

The potential role of fatty acid synthase was examined for vaccinia replication. It was seen that the fatty acid synthase inhibitor cerulenin also significantly reduced vaccinia replication in tumor cells in vitro (FIG. 6b).

The replication of TK-HMGB1mut benefited further from infection of tumors in models of obesity. The replication of both TK- and TK-HMGB1mut increased in the context of mice fed a high-fat diet (FIGS. 6c and 6d).

HMGB1mut synergizes with chemotherapies, including taxols and platinum-based drugs such as cisplatin. Media taken from cells infected with TK-HMGB1mut, filtered to remove any viral particles, and then placed on a fresh tumor cell layer sensitized these cells to subsequent exposure to chemotherapies, including cisplatin and taxol (FIG. 7a). This effect was unexpectedly pronounced for viruses expressing HMGB1 mut.

The effects were even more unexpectedly pronounced in vivo (FIG. 7b). BALB/c mice bearing Renca tumors were treated with a single intravenous injection of viruses (TK- or TK-HMGB1mut) alone or in combination with paclitaxel (Taxol®). It was seen that TK-HMGB1mut plus Taxol® produced a significantly greater therapeutic effect than any other treatment.

The effects of vaccinia strain expression alone or in combination with matrix metalloproteinase-8 (MMP8) expression or expression of the hyaluronidase PH-20 on viral spread were evaluated in mice. Bioluminescent imaging of tumors in mice treated with a vaccinia strain only (WR TK-only), vaccinia strain and MMP8 expression (WR TK-mmp8), or vaccinia strain and PH20 expression (WR TK-ph20) revealed significantly increased viral spread in tumors with vaccinia strain and PH20 expression relative to the other conditions (FIGS. 8a and 8b).

Figure 9:
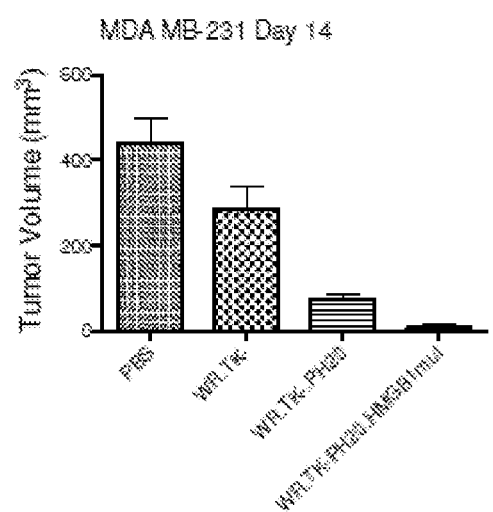
FIG. 9 shows the effect of treatment with vaccinia virus containing the exemplary variant HMGB1 (HMGB1mut) alone or in combination with PH20 expression on tumor volume. Athymic nu/nu mice bearing subcutaneous MDA-MB-231 tumors (50-100 mm$^3$) were treated with the viruses indicated via a single intravenous treatment using 1E7 plaque-forming units (PFU). Tumor volume shown was measured at 14 days post treatment.

In vivo experiments further demonstrated the enhanced therapeutic effect of a combination of HMGB1mut and PH20 expression. Immunocompromised (athymic nu/nu) mice bearing pre-established subcutaneous MDA-MB-231 tumors (50-100 mm$^3$) were treated with a single intravenous dose of PBS (control) or virus (WR.TK-, WR.TK-PH20, or WR.TK-PH20.HMGB1mut), and tumor volume was measured. Treatment with WR.TK-PH20.HMGB1mut most significantly reduced tumor volume as measured 14 days post-treatment (FIG. 9).

Figure 10:
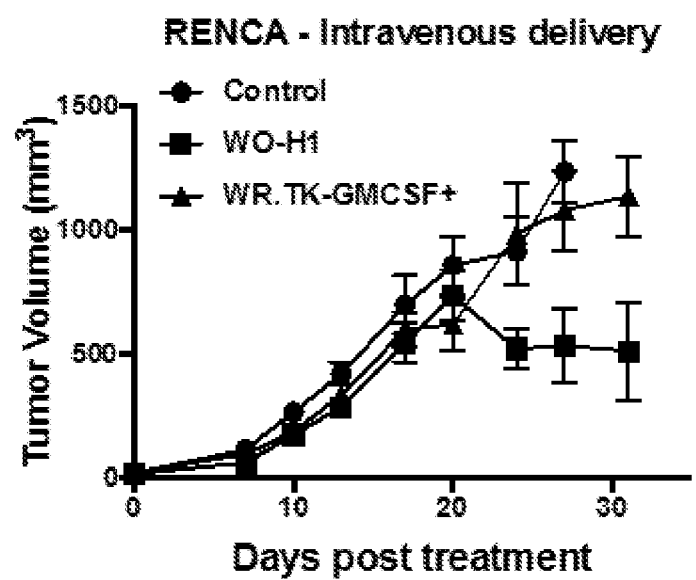
FIG. 10 shows the effect of virus expressing HMGB1mut and PH20 on tumor volume. Mice (BALB/c) bearing subcutaneous Renca tumors (50-100 mm$^3$) were treated (n=10/group) at day 0 with a single intravenous injection of vehicle as a control, 1E8 PFU of virus expressing HMGB1mut and PH20 (WO-H1), or 1E8 PFU of a mimetic of the best in class clinical virus Pexa-Vec, also known as JX-594 (WR.TK-GMCSF+). Tumor volume was measured as a function of days post treatment.

The therapeutic effect of the combination of HMGB1mut and PH20 expression was compared to a mimetic of the best in class clinical virus Pexa-Vec, also known as JX-594 (WR.TK-GMCSF+; FIG. 10). BALB/c mice bearing subcutaneous Renca tumors (50-100 mm$^3$) were treated (n=10/group) at day 0 with a single intravenous injection of vehicle as a control, 1E8 PFU of virus expressing HMGB1mut and PH20 (WO-H1), or 1E8 PFU of virus expressing WR.TK-GMCSF+. Tumor volume was measured as a function of days post treatment. Treatment with HMGB1mut and PH20 resulted in reduced tumor volume relative to treatment with the Pexa-Vec mimetic (FIG. 10).

Figure 11:
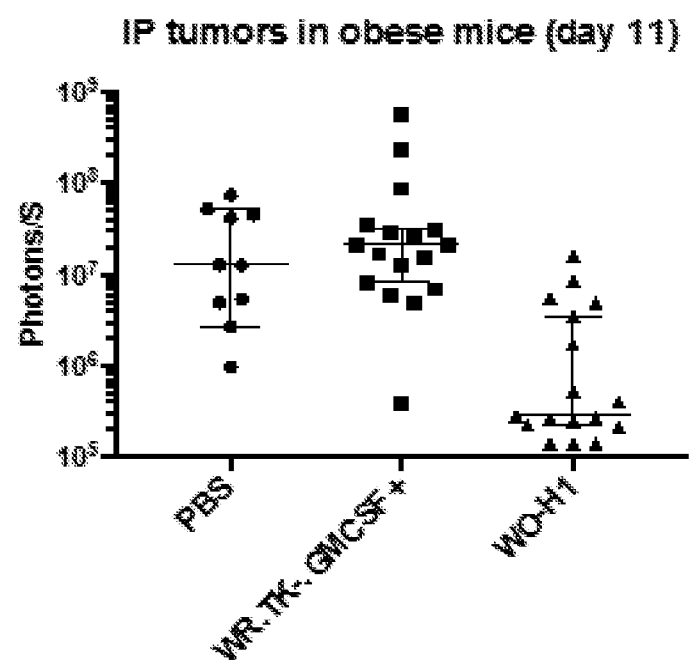
FIG. 11 shows the effect of virus expressing HMGB1mut and PH20 on tumor volume in a model of peritoneal cancer in obese mice. Mice (C57/BL6) were fed a high fat diet until body weight increased >10% over control mice fed a normal diet. Mice were then implanted with MC-38 colorectal cancer cells expressing luciferase into the peritoneal cavity. Tumor growth was followed by bioluminescence imaging. Once tumors were established, mice were treated with a single, low dose intraperitoneal injection of PBS (control), 5E6 PFU of virus expressing HMGB1mut and PH20 (WO-H1), or 5E6 PFU of a mimetic of the best in class clinical virus Pexa-Vec, also known as JX-594 (WR.TK-GMCSF+).

The therapeutic effect of the combination of HMGB1mut and PH20 expression was also compared to the Pexa-Vec mimetic in a model of peritoneal cancer in obese mice. C57/BL6 mice were fed a high-fat diet until body weight increased >10% over control mice fed a normal diet. Mice were then implanted with MC-38 colorectal cancer cells expressing luciferase into the peritoneal cavity. Tumor growth was followed by bioluminescence imaging. Once tumors were established (after 5 days), mice were treated with a single, low dose intraperitoneal injection of PBS (control), 0.5E6 PFU of virus expressing HMGB1 mut and PH20, or 5E6 PFU of virus expressing the Pexa-Vec mimetic. Of note, the Pexa-Vec mimetic (WR.TK-.GMCSF+) actually resulted in slightly increased tumor growth, whereas the HMGB1mut and PH20 expressing virus (WO-H1) displayed significantly decreased tumor burden relative to PBS controls (FIG. 11).

Figure 12:
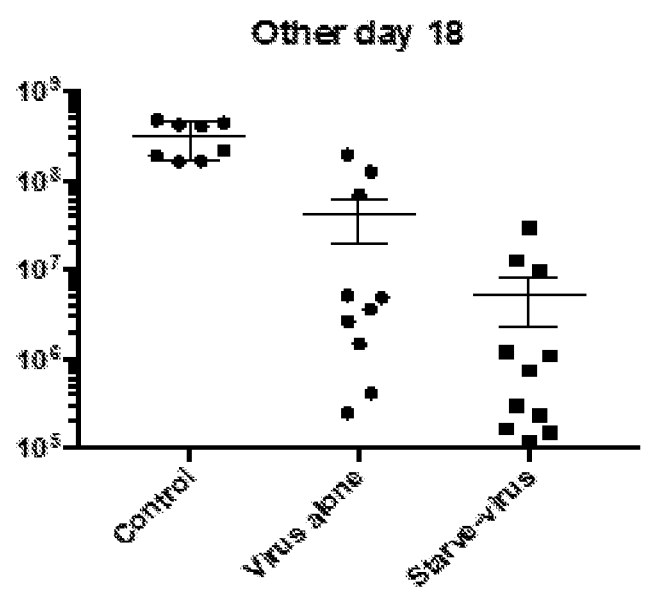
FIG. 12 shows the effect of virus expressing HMGB1mut and PH20 on tumor volume in mice fed a ketogenic diet. Mice (C57/BL6) were implanted with MC-38 colorectal cancer cells expressing luciferase into the peritoneal cavity. Tumor growth was followed by bioluminescence imaging. Once tumors were established, mice were treated with a period of 24 h starvation followed by low dose (5E6 PFU intraperitoneal) virus treatment with WO-H1 (Starve-virus), or virus alone.

The therapeutic activity of the combination of HMGB1mut and PH20 expression was evaluated in the context of prior short term starvation. C57/BL6 mice were implanted with MC-38 colorectal cancer cells expressing luciferase into the peritoneal cavity. Tumor growth was followed by bioluminescence imaging. Once tumors were established (after 5 days), mice were treated with virus alone or with a period of 24 h starvation followed by low dose (5E6 PFU intraperitoneal) HMGB1mut and PH20 expressing (WO-H1) virus (FIG. 12). It was determined that, although WO-H1 displayed therapeutic activity in this model, this effect was enhanced through prior short term starvation, which was a pre-treatment designed to mimic a ketogenic diet and expected to increase autophagy in the tumor.

Example 3: Expression of an Exemplary Variant HMGB1 from a Modified Adeno Associated Virus Enhances Therapeutic Effects in Cancer Cell Lines and Murine Tumor Models The aim of this study is to explore the effects of an exemplary modified oncolytic adeno associated virus, according to this disclosure, where an exogenous nucleic acid encoding a variant HMGB1 is inserted into the viral genome, alone or in combination with a further exogenous gene that codes for PH-20, in cancer cell lines and murine models, in comparison with an adeno associated virus that does not contain the nucleic acid expressing the variant HMGB1. It is observed that administration of the modified adeno associated virus of this disclosure, in combination with chemotherapy, results in a synergistic effect, compared to the control adeno associated virus. Significantly reduced tumor burdens are observed in case of the test modified adeno associated viruses compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 4: Expression of an Exemplary Variant HMGB1 from a Modified Herpes Simplex Virus (HSV) Enhances Therapeutic Effects in Cancer Cell Lines and Murine Tumor Models The aim of this study is to explore the effects of an exemplary modified oncolytic HSV, according to this disclosure, where an exogenous nucleic acid encoding a variant HMGB1 is inserted into the viral genome, alone or in combination with a further exogenous gene that codes for PH-20, in cancer cell lines and murine models, in comparison with a HSV that does not contain the nucleic acid expressing the variant HMGB1. It is observed that administration of the modified HSV of this disclosure, in combination with chemotherapy, results in a synergistic effect, compared to the control HSV. Significantly reduced tumor burdens are observed in case of the test modified HSV compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 5: Expression of an Exemplary Variant HMGB1 from a Modified Adenovirus Enhances Therapeutic Effects in Cancer Cell Lines and Murine Tumor Models The aim of this study is to explore the effects of an exemplary modified oncolytic adenovirus, according to this disclosure, where an exogenous nucleic acid encoding a variant HMGB1 is inserted into the viral genome, alone or in combination with a further exogenous gene that codes for PH-20, in cancer cell lines and murine models, in comparison with an adenovirus that does not contain the nucleic acid expressing the variant HMGB1. It is observed that administration of the modified adenovirus of this disclosure, in combination with chemotherapy, results in a synergistic effect, compared to the control adenovirus. Significantly reduced tumor burdens are observed in case of the test modified adenovirus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 6: Expression of an Exemplary Variant HMGB1 from a Modified Vesicular Stomatitis Virus (VSV) Enhances Therapeutic Effects in Cancer Cell Lines and Murine Tumor Models The aim of this study is to explore the effects of an exemplary modified oncolytic VSV, according to this disclosure, where an exogenous nucleic acid encoding a variant HMGB1 is inserted into the viral genome, alone or in combination with a further exogenous gene that codes for PH-20, in cancer cell lines and murine models, in comparison with a VSV that does not contain the nucleic acid expressing the variant HMGB1. It is observed that administration of the modified VSV of this disclosure, in combination with chemotherapy, results in a synergistic effect, compared to the control VSV. Significantly reduced tumor burdens are observed in case of the test modified VSV compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 6: Expression of an Exemplary Variant HMGB1 from a Modified Poliovirus Enhances Therapeutic Effects in Cancer Cell Lines and Murine Tumor Models The aim of this study is to explore the effects of an exemplary modified oncolytic poliovirus, according to this disclosure, where an exogenous nucleic acid encoding a variant HMGB1 is inserted into the viral genome, alone or in combination with a further exogenous gene that codes for PH-20, in cancer cell lines and murine models, in comparison with a poliovirus that does not contain the nucleic acid expressing the variant HMGB1. It is observed that administration of the modified poliovirus of this disclosure, in combination with chemotherapy, results in a synergistic effect, compared to the control poliovirus. Significantly reduced tumor burdens are observed in case of the test modified poliovirus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 7: Expression of an Exemplary Variant HMGB1 from a Modified Newcastle Disease Virus (NDV) Enhances Therapeutic Effects in Cancer Cell Lines and Murine Tumor Models The aim of this study is to explore the effects of an exemplary modified oncolytic NDV, according to this disclosure, where an exogenous nucleic acid encoding a variant HMGB1 is inserted into the viral genome, alone or in combination with a further exogenous gene that codes for PH-20, in cancer cell lines and murine models, in comparison with a NDV that does not contain the nucleic acid expressing the variant HMGB1. It is observed that administration of the modified NDV of this disclosure, in combination with chemotherapy, results in a synergistic effect, compared to the control NDV. Significantly reduced tumor burdens are observed in case of the test modified NDV compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 8: Expression of an Exemplary Variant HMGB1 from a Modified Seneca Valley Virus (SVV) Enhances Therapeutic Effects in Cancer Cell Lines and Murine Tumor Models The aim of this study is to explore the effects of an exemplary modified oncolytic SVV, according to this disclosure, where an exogenous nucleic acid encoding a variant HMGB1 is inserted into the viral genome, alone or in combination with a further exogenous gene that codes for PH-20, in cancer cell lines and murine models, in comparison with a SVV that does not contain the nucleic acid expressing the variant HMGB1. It is observed that administration of the modified SVV of this disclosure, in combination with chemotherapy, results in a synergistic effect, compared to the control SVV. Significantly reduced tumor burdens are observed in case of the test modified SVV compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 9: Expression of an Exemplary Variant HMGB1 from a Modified Coxsackievirus Enhances Therapeutic Effects in Cancer Cell Lines and Murine Tumor Models The aim of this study is to explore the effects of an exemplary modified oncolytic coxsackievirus, according to this disclosure, where an exogenous nucleic acid encoding a variant HMGB1 is inserted into the viral genome, alone or in combination with a further exogenous gene that codes for PH-20, in cancer cell lines and murine models, in comparison with a coxsackievirus that does not contain the nucleic acid expressing the variant HMGB1. It is observed that administration of the modified coxsackievirus of this disclosure, in combination with chemotherapy, results in a synergistic effect, compared to the control coxsackievirus. Significantly reduced tumor burdens are observed in case of the test modified coxsackievirus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 10: Expression of an Exemplary Variant HMGB1 from a Modified Reovirus Enhances Therapeutic Effects in Cancer Cell Lines and Murine Tumor Models The aim of this study is to explore the effects of an exemplary modified oncolytic reovirus, according to this disclosure, where an exogenous nucleic acid encoding a variant HMGB1 is inserted into the viral genome, alone or in combination with a further exogenous gene that codes for PH-20, in cancer cell lines and murine models, in comparison with a reovirus that does not contain the nucleic acid expressing the variant HMGB1. It is observed that administration of the modified reovirus of this disclosure, in combination with chemotherapy, results in a synergistic effect, compared to the control reovirus. Significantly reduced tumor burdens are observed in case of the test modified reovirus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 11: Expression of an Exemplary Variant HMGB1 from a Modified Lentivirus Enhances Therapeutic Effects in Cancer Cell Lines and Murine Tumor Models The aim of this study is to explore the effects of an exemplary modified oncolytic lentivirus, according to this disclosure, where an exogenous nucleic acid encoding a variant HMGB1 is inserted into the viral genome, alone or in combination with a further exogenous gene that codes for PH-20, in cancer cell lines and murine models, in comparison with a lentivirus that does not contain the nucleic acid expressing the variant HMGB1. It is observed that administration of the modified lentivirus of this disclosure, in combination with chemotherapy, results in a synergistic effect, compared to the control lentivirus. Significantly reduced tumor burdens are observed in case of the test modified lentivirus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 12: Expression of an Exemplary Variant HMGB1 from a Modified Measles Virus Enhances Therapeutic Effects in Cancer Cell Lines and Murine Tumor Models The aim of this study is to explore the effects of an exemplary modified oncolytic measles virus, according to this disclosure, where an exogenous nucleic acid encoding a variant HMGB1 is inserted into the viral genome, alone or in combination with a further exogenous gene that codes for PH-20, in cancer cell lines and murine models, in comparison with a measles virus that does not contain the nucleic acid expressing the variant HMGB1. It is observed that administration of the modified measles virus of this disclosure, in combination with chemotherapy, results in a synergistic effect, compared to the control measles virus. Significantly reduced tumor burdens are observed in case of the test modified measles virus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 13: Expression of an Exemplary Variant HMGB1 from a Modified Maraba Virus Enhances Therapeutic Effects in Cancer Cell Lines and Murine Tumor Models The aim of this study is to explore the effects of an exemplary modified oncolytic maraba virus, according to this disclosure, where an exogenous nucleic acid encoding a variant HMGB1 is inserted into the viral genome, alone or in combination with a further exogenous gene that codes for PH-20, in cancer cell lines and murine models, in comparison with a maraba virus that does not contain the nucleic acid expressing the variant HMGB1. It is observed that administration of the modified maraba virus of this disclosure, in combination with chemotherapy, results in a synergistic effect, compared to the control maraba virus. Significantly reduced tumor burdens are observed in case of the test modified maraba virus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 14: Expression of an Exemplary Variant HMGB1 from a Modified Myxomavir Virus Enhances Therapeutic Effects in Cancer Cell Lines and Murine Tumor Models The aim of this study is to explore the effects of an exemplary modified oncolytic myxomavir virus, according to this disclosure, where an exogenous nucleic acid encoding a variant HMGB1 is inserted into the viral genome, alone or in combination with a further exogenous gene that codes for PH-20, in cancer cell lines and murine models, in comparison with a myxomavir virus that does not contain the nucleic acid expressing the variant HMGB1. It is observed that administration of the modified myxomavir virus of this disclosure, in combination with chemotherapy, results in a synergistic effect, compared to the control myxomavir virus. Significantly reduced tumor burdens are observed in case of the test modified myxomavir virus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 15: Expression of an Exemplary Variant HMGB1 from a Modified Mengovirus Enhances Therapeutic Effects in Cancer Cell Lines and Murine Tumor Models The aim of this study is to explore the effects of an exemplary modified oncolytic mengovirus, according to this disclosure, where an exogenous nucleic acid encoding a variant HMGB1 is inserted into the viral genome, alone or in combination with a further exogenous gene that codes for PH-20, in cancer cell lines and murine models, in comparison with a mengovirus that does not contain the nucleic acid expressing the variant HMGB1. It is observed that administration of the modified mengovirus of this disclosure, in combination with chemotherapy, results in a synergistic effect, compared to the control mengovirus. Significantly reduced tumor burdens are observed in case of the test modified mengovirus compared to the control virus, upon administration to mice that are fed a high-fat diet until body weight increases >10% over control mice fed a normal diet and are subsequently implanted MC-38 colorectal cancer cells expressing luciferase into the peritoneal cavity.

Example 16: Expression of an Exemplary Variant HMGB1, in Combination with a Further Viral Gene Modification, from A Modified Vaccinia Virus Enhances Therapeutic Effects in Cancer Cell Lines and Murine Tumor Models The aim of this study is to explore the effects of an exemplary modified oncolytic vaccinia virus, according to this disclosure, where an exogenous nucleic acid encoding a variant HMGB1 is inserted into the viral genome, in combination with a further exogenous gene that codes for PH-20, and a B8R gene deletion, in cancer cell lines and murine models, in comparison with an oncolytic vaccinia virus that does not contain the nucleic acids expressing the variant HMGB1 and PH-20, and B8R gene deletion. It is observed that administration of the modified oncolytic vaccinia virus of this disclosure, in combination with chemotherapy, results in a synergistic effect, compared to the control oncolytic vaccinia virus. Significantly reduced tumor burdens are observed in case of the test modified oncolytic vaccinia virus compared to the control virus, upon administration to mice that are fed a high-fat diet until body weight increases >10% over control mice fed a normal diet and are subsequently implanted MC-38 colorectal cancer cells expressing luciferase into the peritoneal cavity.

---

What is claimed is:

1. An oncolytic vaccinia virus comprising an exogenous nucleic acid that codes for a variant High Mobility Group Box 1 (HMGB1) comprising a sequence that comprises a mutation in one or a combination of the following amino acid positions of SEQ ID NO: 16 (wild-type HMGB1): 35, 42, 89, 181, 189, and 202.

2. The oncolytic vaccinia virus of claim 1, wherein the variant HMGB1 comprises an amino acid sequence with at least 90% homology to an amino acid sequence selected from the group consisting of: SEQ ID NO: 4, SEQ ID NO: 15, SEQ ID NO: 17, SEQ ID NO: 22, SEQ ID NO: 23, SEQ ID NO: 24, and SEQ ID NO: 25.

3. The oncolytic vaccinia virus of claim 1, wherein the exogenous nucleic acid that codes for the variant HMGB1 comprises a nucleotide sequence with at least 90% homology to a sequence selected from the group consisting of: SEQ ID NO: 13, SEQ ID NO: 14, and SEQ ID NO: 19.

4. The oncolytic vaccinia virus of claim 1, further comprising an exogenous nucleic acid that codes for an antigen binding protein operably linked to the exogenous nucleic acid that codes for the variant HMGB1.

5. The oncolytic vaccinia virus of claim 1, further comprising an exogenous nucleic acid that codes for a hyaluronidase operably linked to the exogenous nucleic acid that codes for the variant HMGB1.

6. The oncolytic vaccinia virus of claim 5, wherein the hyaluronidase increases the spread of the oncolytic vaccinia virus, compared to the spread of an otherwise identical oncolytic vaccinia virus that does not comprise the exogenous nucleic acid that codes for the hyaluronidase operably linked to the exogenous nucleic acid that codes for the variant HMGB 1 wherein the increase in spread is measured by a bioluminescence assay using a reporter gene demonstrating viral gene expression.

7. The oncolytic vaccinia virus of claim 1, wherein the oncolytic vaccinia virus comprises a deletion of a viral gene.

8. The oncolytic vaccinia virus of claim 7, wherein the viral gene is a virulence gene.

9. The oncolytic vaccinia virus of claim 1, further comprising an exogenous nucleic acid sequence that codes for an IgE or a domain thereof, fused upstream to the exogenous nucleic acid that codes for the variant HMGB1.

10. The oncolytic vaccinia virus of claim 1, wherein the virus further encodes a chemotherapy sensitizer or comprises an exogenous nucleic acid that codes for at least one of: an apoptosis inhibitor or an efflux pump blocker.

11. The oncolytic vaccinia virus of claim 1, wherein the virus is an extracellular enveloped virus.

12. An isolated polynucleotide that comprises a sequence with at least 90% homology to SEQ ID NO: 13 and codes for a variant HMGB1 comprising a sequence that comprises a mutation in one or a combination of the following amino acid positions of SEQ ID NO: 16 (wild-type HMGB1): 35, 42, 89, 181, 189, and 202.

13. A method of treatment comprising administering to a subject a composition comprising an isolated polynucleotide according to claim 12.

14. An oncolytic vaccinia virus comprising an exogenous nucleic acid that codes for a variant HMGB1 comprising an amino acid sequence with at least 90% homology to an amino acid sequence selected from the group consisting of: SEQ ID NO: 4, SEQ ID NO: 15, SEQ ID NO: 17, SEQ ID NO: 22, SEQ ID NO: 23, SEQ ID NO: 24, and SEQ ID NO: 25.

15. The oncolytic vaccinia virus of claim 14, wherein the variant HMGB1 or the domain thereof comprises an amino acid sequence with at least 95% homology to an amino acid sequence selected from the group consisting of: SEQ ID NO: 4, SEQ ID NO: 15, SEQ ID NO: 17, SEQ ID NO: 22, SEQ ID NO: 23, SEQ ID NO: 24, and SEQ ID NO: 25.

16. The oncolytic vaccinia virus of claim 14, wherein the variant HMGB1 comprises an amino acid sequence with at least 98% homology to an amino acid sequence selected from the group consisting of: SEQ ID NO: 4, SEQ ID NO: 15, SEQ ID NO: 17, SEQ ID NO: 22, SEQ ID NO: 23, SEQ ID NO: 24, and SEQ ID NO: 25.

17. The oncolytic vaccinia virus of claim 14, further comprising an exogenous nucleic acid that codes for an antigen binding protein operably linked to the exogenous nucleic acid that codes for the variant HMGB 1.

18. The oncolytic vaccinia virus of claim 14, further comprising an exogenous nucleic acid that codes for a hyaluronidase operably linked to the exogenous nucleic acid that codes for the variant HMGB 1.

19. The oncolytic vaccinia virus of claim 14, wherein the vaccinia virus comprises a deletion of a viral gene.

20. The oncolytic vaccinia virus of claim 19, wherein the viral gene is a virulence gene.

21. The oncolytic vaccinia virus of claim 14, further comprising an exogenous nucleic acid sequence that codes for an IgE or a domain thereof, fused upstream to the exogenous nucleic acid that codes for the variant HMGB1.

22. The oncolytic vaccinia virus of claim 14, wherein the virus further encodes a chemotherapy sensitizer or comprises an exogenous nucleic acid that codes for at least one of: an apoptosis inhibitor or an efflux pump blocker.

23. The oncolytic vaccinia virus of claim 14, wherein the virus is an extracellular enveloped virus.

* * * * *